United States Patent
Huck et al.

(10) Patent No.: US 9,139,568 B2
(45) Date of Patent: Sep. 22, 2015

(54) HETEROCYCLIC CARBOXAMIDES AS MODULATORS OF KINASE ACTIVITY

(71) Applicant: Merck Patent GmbH, Darmstadt (DE)

(72) Inventors: Bayard R. Huck, Sudbury, MA (US); Xiaoling Chen, Chestnut Hill, MA (US); Yufang Xiao, Lexington, MA (US); Ruoxi Lan, Waltham, MA (US); Lizbeth Celeste De Selm, Melrose, MA (US); Constantin Neagu, Belmont, MA (US); Justin Potnick, Acton, MA (US); Srinivasa R. Karra, Pembroke, MA (US); Theresa L. Johnson, Salem, MA (US)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 14/359,937

(22) PCT Filed: Dec. 17, 2012

(86) PCT No.: PCT/US2012/070085
§ 371 (c)(1),
(2) Date: May 22, 2014

(87) PCT Pub. No.: WO2013/096194
PCT Pub. Date: Jun. 27, 2013

(65) Prior Publication Data
US 2014/0309245 A1    Oct. 16, 2014

Related U.S. Application Data

(60) Provisional application No. 61/579,377, filed on Dec. 22, 2011.

(51) Int. Cl.
| | |
|---|---|
| *C07D 401/12* | (2006.01) |
| *C07D 403/12* | (2006.01) |
| *A61K 31/517* | (2006.01) |
| *C07D 401/14* | (2006.01) |
| *C07D 215/48* | (2006.01) |
| *C07D 401/04* | (2006.01) |
| *C07D 403/04* | (2006.01) |
| *C07D 239/74* | (2006.01) |

(52) U.S. Cl.
CPC ............ *C07D 403/12* (2013.01); *C07D 215/48* (2013.01); *C07D 239/74* (2013.01); *C07D 401/04* (2013.01); *C07D 401/12* (2013.01); *C07D 401/14* (2013.01); *C07D 403/04* (2013.01)

(58) Field of Classification Search
CPC ........................ C07D 401/12; C07D 403/12
See application file for complete search history.

(56) References Cited

FOREIGN PATENT DOCUMENTS

| EP | 0308897 A1 | 3/1989 |
| WO | 2010/093419 A1 | 8/2010 |

OTHER PUBLICATIONS

Barlund et al., Multiple Genes at 17q23 Undergo Amplification and Overexpression in Breast Cancer, Cancer Res., 2000, 60:5340-5346.
Couch et al., Localization of PS6K to Chromosomal Region 17q23 and Determination of Its Amplification in Breast Cancer, Cancer Res., 1999, 59:1408-11.
Garcia-Bustos J. et al., PIK1, an essential phosphatidylinositol 4-kinase associated with the yeast nucleus, EMBO J., 1994, 13(10):2352-2361.
Hanks, S.K. And Hunter T., The eukaryotic protein kinase superfamily: Kinase (catalytic) domain structure and classification, Faseb J., 1995, 9:576-596.
Hardie and Hanks, the Protein Kinase Facts Book. I and II, 1995, Academic Press, San Diego, CA.
Hiles I. et al., Phosphatidylinositol 3-Kinase: Structure and Expression of the 110 kd Catalytic Subunit, Cell, 1992, 70:419-429.
Knighton D. et al., Crystal Structure of the Catalytic Subunit of Cyclic Adenosine Monophosphate-Dependent Protein Kinase, Science, 1991, 253:407-414.
Kunz J. et al., Target of Rapamycin in Yeast, TOR2, Is an Essential Phosphatidylinositol Kinase Homolog Required for G1 Progression, Cell, 1993, 73:585-596.
Wu et al., 17q23 Amplifications in Breast Cancer Involve the PAT1, RAD51C, PS6K, and SIGMA1B Genes, Cancer Res. (2000): 60:5371-5375.
International Search Report, dated 11 Feb. 2013, pp. 1-4.

*Primary Examiner* — Brian McDowell
(74) *Attorney, Agent, or Firm* — Dwight D. Kim; EMD Serono Research and Development Institute

(57) ABSTRACT

The invention provides novel heterocyclic carboxamide compounds according to Formula (I),

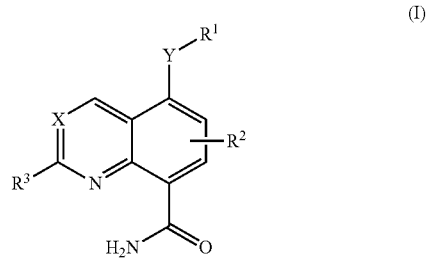

their manufacture, and use for the treatment of hyperproliferative diseases, such as cancer.

13 Claims, No Drawings

HETEROCYCLIC CARBOXAMIDES AS MODULATORS OF KINASE ACTIVITY

RELATED APPLICATIONS

This application is a U.S. national stage application of PCT international application no. PCT/US12/70085, filed on Dec. 17, 2012, which claims the benefit of U.S. provisional Application no. 61/579,377, filed on Dec. 22, 2011. The entire contents of the aforementioned applications are hereby incorporated by reference.

FIELD OF THE INVENTION

The invention relates to a series of heterocyclic carboxamide compounds that are useful in the treatment of hyperproliferative diseases, such as cancer, in mammals. Also encompassed by the present invention is the use of such compounds in the treatment of hyperproliferative diseases in mammals, especially humans, and pharmaceutical compositions containing such compounds.

SUMMARY OF THE RELATED ART

Protein kinases constitute a large family of structurally related enzymes that are responsible for the control of a wide variety of signal transduction processes within the cell (Hardie, G. and Hanks, S. (1995) The Protein Kinase Facts Book. I and II, Academic Press, San Diego, Calif.). The kinases may be categorized into families by the substrates they phosphorylate (e.g., protein-tyrosine, protein-serine/threonine, lipids, etc.). Sequence motifs have been identified that generally correspond to each of these kinase families (e.g., Hanks, S. K., Hunter, T., FASEB J., 9:576-596 (1995); Knighton, et al., Science, 253:407-414 (1991); Hiles, et al., Cell, 70:419-429 (1992); Kunz, et al., Cell, 73:585-596 (1993); Garcia-Bustos, et al., EMBO J., 13:2352-2361 (1994)). Protein kinases may be characterized by their regulation mechanisms. These mechanisms include, for example, autophosphorylation, transphosphorylation by other kinases, protein-protein interactions, protein-lipid interactions, and protein-polynucleotide interactions. An individual protein kinase may be regulated by more than one mechanism.

Kinases regulate many different cell processes including, but not limited to, proliferation, differentiation, apoptosis, motility, transcription, translation and other signalling processes, by adding phosphate groups to target proteins. These phosphorylation events act as molecular on/off switches that can modulate or regulate the target protein biological function. Phosphorylation of target proteins occurs in response to a variety of extracellular signals (hormones, neurotransmitters, growth and differentiation factors, etc.), cell cycle events, environmental or nutritional stresses, etc. The appropriate protein kinase functions in signalling pathways to activate or inactivate (either directly or indirectly), for example, a metabolic enzyme, regulatory protein, receptor, cytoskeletal protein, ion channel or pump, or transcription factor. Uncontrolled signalling due to defective control of protein phosphorylation has been implicated in a number of diseases, including, for example, inflammation, cancer, allergy/asthma, diseases and conditions of the immune system, diseases and conditions of the central nervous system, and angiogenesis.

Protein kinase 70S6K, the 70 kDa ribosomal protein kinase p70S6K (also known as SK6, p70/p85 S6 kinase, p70/p85 ribosomal S6 kinase and p70S6K), is a member of the AGC subfamily of protein kinases. p70S6K is a serine-threonine kinase that is a component of the phosphatidylinositol 3 kinase (PI3K)/AKT pathway. p70S6K is downstream of PI3K, and activation occurs through phosphorylation at a number of sites in response to numerous mitogens, hormones and growth factors. p70S6K activity is also under the control of a mTOR-containing complex (TORC1) since rapamycin acts to inhibit p70S6K activity. p70S6K is regulated by PI3K downstream targets AKT and PKC□. AKT directly phosphorylates and inactivates TSC2, thereby activating mTOR. In addition, studies with mutant alleles of p70S6K that inhibited by Wortmannin but not by rapamycin suggest that the PI3K pathway can exhibit effects on p70S6K independent of the regulation of mTOR activity.

The enzyme p70S6K modulates protein synthesis by phosphorylation of the S6 ribosomal protein. S6 phosphorylation correlates with increased translation of mRNAs encoding components of the translational apparatus, including ribosomal proteins and translational elongation factors whose increased expression is essential for cell growth and proliferation. These mRNAs contain an oligopyrimidime tract at their 5' transcriptional start (termed 5'TOP), which has been shown to be essential for their regulation at the translational level.

In addition to its involvement in translation, p70S6K activation has also been implicated in cell cycle control, neuronal cell differentiation, regulation of cell motility and a cellular response that is important in tumor metastases, the immune response and tissue repair. Antibodies to p70S6K abolish the mitogenic response driven entry of rat fibroblasts into S phase, indication that p70S6K function is essential for the progression from G1 to S phase in the cell cycle. Furthermore, inhibition of cell cycle proliferation at the G1 to S phase of the cell cycle by rapamycin has been identified as a consequence of inhibition of the production of the hyperphosphorylated, activated form of p70S6K.

A role for p70S6K in tumor cell proliferation and protection of cells from apoptosis is supported based on it participation in growth factor receptor signal transduction, overexpression and activation in tumor tissues. For example, Northern and Western analyses revealed that amplification of the PS6K gene was accompanied by corresponding increases in mRNA and protein expression, respectively (Cancer Res. (1999) 59: 1408-11-Localization of PS6K to Chromosomal Region 17q23 and Determination of Its Amplification in Breast Cancer).

Chromosome 17q23 is amplified in up to 20% of primary breast tumors, in 87% of breast tumors containing BRCA2 mutations and in 50% of tumors containing BRCA1 mutations, as well as other cancer types such as pancreatic, bladder and neuroblastoma (see M. Barlund, O. Monni, J. Kononen, R. Cornelison, J. Torhorst, G. Sauter, O.-P. Kallioniemi and Kallioniemi A., Cancer Res., 2000, 60:5340-5346). It has been shown that 17q23 amplifications in breast cancer involve the PAT1, RAD51C, PS6K, and SIGMA1B genes (Cancer Res. (2000): 60, pp. 5371-5375).

The p70S6K gene has been identified as a target of amplification and overexpression in this region, and statistically significant association between amplification and poor prognosis has been observed. Clinical inhibition of p70S6K activation was observed in renal carcinoma patients treated with CCI-779 (rapamycin ester), an inhibitor of the upstream kinase mTOR. A significant linear association between disease progression and inhibition of p70S6K activity was reported. In response to energy stress, the tumor suppressor LKB1 activates AMPK which phosphorylates the TSC1/2 complex and enables it to inactivate the mTOR/p70S6K pathway. Mutations in LKB1 cause Peutz-Jeghers syndrome (PJS), where patients with PJS are 15 times more likely to develop cancer than the general population. In addition, ⅓ of lung adenocarcinomas harbor inactivating LKB1 mutations. P70S6K has been implicated in metabolic diseases and disorders. It was reported that the absence of p70S6K protects against age- and diet-induced obesity while enhancing insulin sensitivity. A role for p70S6K in metabolic and disorders such as obesity, diabetes, metabolic syndrome, insulin resistance, hyperglycemia, hyperaminoacidemia, and hyperlipidmia is supported based upon the findings.

Compounds described as suitable for p70S6K inhibition are disclosed in, i.a. WO 03/064397, WO 04/092154, WO 05/054237, WO 05/056014, WO 05/033086, WO 05/117909, WO 05/039506, WO 06/120573, WO 06/136821, WO 06/071819, WO 06/131835, WO 08/140947 and PCT/US10/000313.

DESCRIPTION OF THE INVENTION

It is the object of the present invention to provide novel compounds that modulate kinase activity. This protein kinase modulation includes, but is not limited to, p70S6K inhibition and AKT inhibition useful in the treatment of hyperproliferative diseases, especially those related to the hyperactivity of the above mentioned protein kinases, such as cancer in mammals, with superior pharmacological properties both with respect to their activities as well as their solubility, metabolic clearance and bioavailability characteristics.

As a result, this invention provides novel, heterocyclic carboxamides and pharmaceutically acceptable salts, solvates or prodrugs thereof, that are kinase inhibitors and useful in the treatment of the above mentioned diseases.

The compounds are defined by Formula (I) and pharmaceutically acceptable salts, solvates, solvates of salts, or prodrugs thereof, wherein:

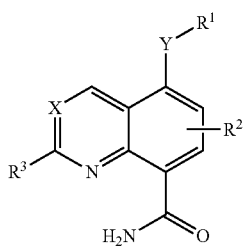

(I)

X is N, or C—$R^4$;
Y is N—$R^5$, O, or absent;
$R^1$ is $L^1$-$R^6$, $L^1$-$R^6$-$L^2$-$R^7$;
$R^2$ is H, Hal, OH, OA, CN, $NH_2$, or NHA;
$R^3$ is H, $CH_3$, or C(Hal)$_3$;
$R^4$ is H, Hal, OH, COOH, $NH_2$, or CN;
$R^5$ is H, LA or monocyclic alkyl having 3, 4, 5, 6, or 7 ring atoms, in which one or two $CH_2$ groups may be replaced by a —NH— group, or
$R^5$, $R^1$ together form monocyclic alkyl having 3, 4, 5, 6, or 7 ring atoms, in which one or two $CH_2$ groups may be replaced by an O atom and/or an —NH—, —NA-, —N($L^1$-$R^6$)—, —CHA-, —CA$_2$-, CH($L^1$-$R^6$)— or —CO— group, and which monocyclic alkyl may be substituted by $NH_2$;
$L^1$, $L^2$ are independently a single bond, or unbranched or branched alkyl having 1, 2, 3, 4 or 5 C atoms, which may be unsubstituted, or mono- or disubstituted with Hal, OH, $NH_2$, NH(LA), N(LA)$_2$, and wherein one or two $CH_2$ groups may be replaced by an O atom or by a —CO—, —NH—, -N(LA)-, —CONH—, —N(LA)COO— or —NHCO— group;
$R^6$ is Ar or monocyclic alkyl having 3, 4, 5, 6, or 7 ring atoms, in which one or two $CH_2$ groups may be replaced by an O atom and/or an —NH—, —NA-, —CHA-, —CO— or —CONHA- group;
Ar is a mono- or bicyclic aromatic homo- or heterocycle having 0, 1, 2, 3 or 4 N, O and/or S atoms and 5, 6, 8, 9, or 10 skeleton atoms, which may be unsubstituted or, independently of one another, mono-, di- or trisubstituted by Hal, A, OA, OH, $NH_2$, or NHA;
A is an unbranched or branched linear or cyclic alkyl having 1, 2, 3, 4, 5 or 6 C atoms, in which one or two $CH_2$ groups may be replaced by an O atom and/or an —NH—, —NHCOAr or —CONHAr group in which 1-3H atoms may be replaced by Hal, and in which one or two $CH_3$ groups may be replaced by $NH_2$, OH, NH(LA) or N(LA)$_2$ group;
LA is unbranched or branched, linear alkyl having 1, 2, 3, or 4 C atoms wherein 1, 2 or 3H atoms may be replaced by Hal (e.g., methyl, ethyl, and trifluoromethyl); and
Hal is F, Cl, Br or I.

In general, all residues which occur more than once may be identical or different, i.e. are independent of one another. Above and below, the residues and parameters have the meanings indicated for the Formula (I), unless expressly indicated otherwise.

Accordingly, the invention relates, in particular, to the compounds of the Formula (I) in which at least one of the said residues has one of the preferred meanings indicated below.

Hal denotes fluorine, chlorine, bromine or iodine, in particular fluorine or chlorine.

"A" denotes, for example, methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl.

"A" further denotes alkyl as defined above, in which one or two $CH_2$ groups may be replaced by O or S atoms and/or by NH, N(LA), CONH, NHCO or —CH=CH-groups and/or in addition 1-3H atoms may be replaced by F and/or Cl, such as, for example, trifluoromethyl, pentafluoroethyl, 1,1-difluoromethyl, 1,1,1-trifluoroethyl, methoxy, ethoxy, n-propoxy, isopropoxy, n-butoxy, isobutoxy, sec-butoxy or tert-butoxy. In other examples of "A", one or two $CH_3$ groups is replaced by OH, SH, $NH_2$, N(LA)H, N(LA)$_2$ or CN, such as, for example, N,N'-dimethylaminoalkyl, 2-aminoethyl, 3-aminopropyl, 4-aminobutyl, 5-aminopentyl, 3-aminomethylcyclobutyl or cyanoalkyl. Cyclic A preferably denotes cyclopropyl, cyclobutyl, cyclopentyl, cyclohexyl or cycloheptyl.

"LA" denotes unbranched or branched, linear alkyl having 1, 2, 3 or 4 C atoms, i.e. methyl, ethyl, propyl, isopropyl, butyl, isobutyl, sec-butyl or tert-butyl.

"Ar" denotes, for example, unsubstituted phenyl, naphthyl or biphenyl, furthermore preferably, for example, phenyl, naphthyl or biphenyl, each of which is mono-, di- or trisubstituted by A, fluorine, chlorine, bromine, iodine, hydroxyl, methoxy, ethoxy, propoxy, butoxy, pentyloxy, hexyloxy, nitro, cyano, formyl, acetyl, propionyl, trifluoromethyl, amino, methylamino, ethylamino, dimethylamino, diethylamino, benzyloxy, sulfonamido, methylsulfonamido, ethylsulfonamido, propylsulfonamido, butylsulfonamido, dimethylsulfonamido, phenylsulfonamido, carboxyl, methoxycarbonyl, ethoxycarbonyl, aminocarbonyl.

"Ar" furthermore denotes o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methylamino)-phenyl, o-, m- or p-(N-methylaminocarbonyl)phenyl, o-, m- or p-acetamidophenyl, o-, m- or p-methoxyphenyl, o-, m- or p-ethoxyphenyl, o-, m- or p-ethoxycarbonylphenyl, o-, m- or p-(N,N-dimethylamino)phenyl, o-, m- or p-(N,N-dimethylaminocarbonyl)phenyl, o-, m- or p-(N-ethylamino)phenyl, o-, m- or p-(N,N-diethylamino)phenyl, o-, m- or p-fluoro-phenyl, o-, m- or p-bromophenyl, o-, m- or p-chlorophenyl, o-, m- or p-(methylsulfonamido)phenyl, o-, m- or p-(methylsulfonyl)phenyl, further preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl, (4-methoxyphenyl)methyl, (3-methoxyphenyl)methyl, (4-methoxyphenyl)ethyl, (3-methoxyphenyl)ethyl.

"Ar" furthermore preferably denotes 2-, 3- or 4-phenyl, 2-, 3- or 4-phenylmethyl, 2-, 3- or 4-phenylethyl, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 3- or 4-pyridylmethyl, 2-, 3- or 4-pyridylethyl, 2-, 4-, 5- or 6-pyrimidinyl, 2-, 3-, 5-, or 6-pyrazin-1- or 4-yl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-oxadiazol-2-yl, 1,3,4-thiadiazol-2- or -5-yl, 1,2,4-thiadiazol-3- or -5-yl, 1,2,3-thiadiazol-4- or -5-yl, 3- or 4-pyridazinyl, 1-, 2-, 3-, 4-, 5-, 6- or 7-indolyl, 2-, 3-, 4- or 5-isoindolyl, 2-, 6, - or 8-purinyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 1-, 3-, 4-, 5-, 6-, 7- or 8-isoquinolinyl, 3-, 4-, 5-, 6-, 7- or 8-quinolinyl, 2-, 4-, 5-, 6-, 7- or 8-quinazolinyl, quinoxalin-2-, 3-, 4- or 5-yl, 4-, 5-, or 6-phthalazinyl, 2-, 3-, 5-, 6-, 7- or 8-2H-benzo-1,4-oxazinyl, further preferably 1,3-benzodioxol-2-, 4- or 5-yl, thiophen-2- or 3-yl, 1,4-benzodioxan-6-yl, 2,1,3-benzothiadiazol-4- or -5-yl or 2,1,3-benzoxadiazol-5-yl, furan-2- or 3-yl, 2,3-dihydro-benzofuran-2-, 3-, 4- or 5-yl, each of which is unsubstituted or may be mono-, di- or trisubstituted, for example, by carbonyl oxygen, F, Cl, Br, methyl, ethyl, propyl, phenyl, benzyl, —CH$_2$-cyclohexyl, hydroxyl, methoxy, ethoxy, amino, methylamino, dimethylamino, nitro, cyano, carboxyl, methoxycarbonyl, aminocarbonyl, methylaminocarbonyl, dimethylaminocarbonyl, acetamino, ureido, methylsulfonylamino, formyl, acetyl, aminosulfonyl and/or methylsulfonyl.

Particularly preferred are compounds of Subformulae 1 to 10 of Formula (I), and pharmaceutically acceptable salts, solvates or prodrugs thereof, wherein in Subformula 1
X is N,
Y is N—$R^5$,
in Subformula 2
X is N,
Y is N—$R^5$,
$R^5$, $R^1$ together form monocyclic alkyl having 3, 4, 5, 6, or 7 ring atoms, in which one or two CH$_2$ groups may be replaced by an —NH—, —NA-, —N($L^1$-$R^6$)—, —CHA-, —CA$_2$-, CH($L^1$-$R^6$)— or —CO— group, and which monocyclic alkyl may be substituted by NH$_2$,
in Subformula 3
X is N,
Y is N—$R^5$,
$R^5$, $R^1$ together form monocyclic alkyl having 4, 5 or 6 ring atoms, in which one CH$_2$ group is replaced by an —N($L^1$-$R^6$)— group, and which monocyclic alkyl may be substituted by NH$_2$,
in Subformula 4
X is N,
Y is N—$R^5$,
$R^5$, $R^1$ together form monocyclic alkyl having 4, 5 or 6 ring atoms, in which one CH$_2$ group is replaced by an —N($L^1$-$R^6$)— group, and which monocyclic alkyl may be substituted by NH$_2$,
$L^1$ is a bond, —CONH—, —NHCO—, —CONHCH$_2$—, CH$_2$CONH—,
in Subformula 5
X is N,
Y is N—$R^5$,
$R^5$, $R^1$ together form monocyclic alkyl having 4, 5 or 6 ring atoms, in which one CH$_2$ group is replaced by an —N($L^1$-$R^6$)— group, and which monocyclic alkyl may be substituted by NH$_2$,
$R^6$ is phenyl, which is unsubstituted, or independently mono-, di- or trisubstituted by Hal, C(Hal)$_3$, CH$_3$, C(Hal)$_3$O,
in Subformula 6
X is N,
Y is N—$R^5$,
X is N,
Y is N—$R^5$,
$R^5$, $R^1$ together form monocyclic alkyl having 4, 5 or 6 ring atoms, in which one CH$_2$ group is replaced by an —N($L^1$-$R^6$)— group, and which monocyclic alkyl may be substituted by NH$_2$,
$L^1$ is a bond, —CONH—, —NHCO—, —CONHCH$_2$—, CH$_2$CONH—,
$R^6$ is phenyl, which is unsubstituted, or independently mono-, di- or trisubstituted by Hal, C(Hal)$_3$, CH$_3$, CH$_3$O, C(Hal)$_3$O,
in Subformula 7
X is N,
Y is NH,
$R^1$ is $L^1$-$R^6$-$L^2$-$R^7$,
$L^1$, $L^2$ are a bond,
$R^6$ monocyclic alkyl having 4, 5 or 6 ring atoms, in which one CH$_2$ group is replaced by an —NH—, group,
$R^7$ is phenyl, which is unsubstituted, or independently mono-, di- or trisubstituted by Hal, C(Hal)$_3$, CH$_3$, CH$_3$O, C(Hal)$_3$O,
in Subformula 8
X is N,
Y is NH,
$R^1$ is $L^1$-$R^6$-$L^2$-$R^7$,
$L^1$, $L^2$ are a bond,
$R^6$ is piperidyl or pyrrolidinyl, $R^7$ is phenyl, which is mono- or disubstituted by Hal, $C(Hal)_3$, $CH_3$, $CH_3O$, $C(Hal)_3O$,
in Subformula 9
X is N,
Y is NH,
$R^1$ is $L^1$-$R^6$-$L^2$-$R^7$,
$L^1$, $L^2$ are a bond,
$R^6$ is

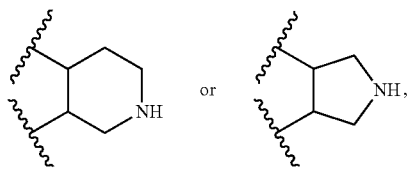 [SMILES: *C1CCNCC1* ; *C1CNCC1*]

$R^7$ is phenyl, which is mono- or disubstituted by Hal, $C(Hal)_3$, $CH_3$, $CH_3O$, $C(Hal)_3O$,
in Subformula 10
X is N,
Y is NH,
$R^1$ is $L^1$-$R^6$,
$R^6$ is phenyl, which is unsubstituted, or independently mono-, di- or trisubstituted by Hal, $C(Hal)_3$, $CH_3$, $CH_3O$, $C(Hal)_3O$,
and the remaining residues have the meaning as indicated for Formula (I) above.

The compounds of the present invention can be in the form of a prodrug compound. "Prodrug compound" means a derivative that is converted into a biologically active compound according to the present invention under physiological conditions in the living body, e.g., by oxidation, reduction, hydrolysis or the like, each of which is carried out enzymatically, or without enzyme involvement. Examples of prodrugs are compounds, wherein the amino group in a compound of the present invention is acylated, alkylated or phosphorylated, e.g., eicosanoylamino, alanylamino, pivaloyloxymethylamino or wherein the hydroxyl group is acylated, alkylated, phosphorylated or converted into the borate, e.g. acetyloxy, palmitoyloxy, pivaloyloxy, succinyloxy, fumaryloxy, alanyloxy or wherein the carboxyl group is esterified or amidated, or wherein a sulfhydryl group forms a disulfide bridge with a carrier molecule, e.g. a peptide, that delivers the drug selectively to a target and/or to the cytosol of a cell. These compounds can be produced from compounds of the present invention according to well-known methods. Other examples of prodrugs are compounds, wherein the carboxylate in a compound of the present invention is for example converted into an alkyl-, aryl-, choline-, amino, acyloxymethylester, linolenoyl-ester.

Metabolites of compounds of the present invention are also within the scope of the present invention.

Where tautomerism, e.g., keto-enol tautomerism, of compounds of the present invention or their prodrugs may occur, the individual forms, e.g., the keto or the enol form, are claimed separately and together as mixtures in any ratio. The same applies for stereoisomers, e.g., enantiomers, cis/trans isomers, conformers and the like. If desired, isomers can be separated by methods well known in the art, e.g. by liquid chromatography. The same applies for enantiomers, e.g., by using chiral stationary phases. Additionally, enantiomers may be isolated by converting them into diastereomers, i.e., coupling with an enantiomerically pure auxiliary compound, subsequent separation of the resulting diastereomers and cleavage of the auxiliary residue. Alternatively, any enantiomer of a compound of the present invention may be obtained from stereoselective synthesis using optically pure starting materials.

The compounds of the present invention can be in the form of a pharmaceutically acceptable salt or a solvate. The term "pharmaceutically acceptable salts" refers to salts prepared from pharmaceutically acceptable non-toxic bases or acids, including inorganic bases or acids and organic bases or acids. In cases where the compounds of the present invention contain one or more acidic or basic groups, the invention also comprises their corresponding pharmaceutically or toxicologically acceptable salts, in particular their pharmaceutically utilizable salts. Thus, the compounds of the present invention which contain acidic groups can be present in salt form, and can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Compounds of the present invention which contain one or more basic groups, i.e. groups which can be protonated, can be present in salt form, and can be used according to the invention in the form of their addition salts with inorganic or organic acids. Examples of suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the present invention simultaneously contain acidic and basic groups in the molecule, the invention also includes, in addition to the salt forms mentioned, inner salts or betaines (zwitterions). The respective salts can be obtained by customary methods which are known to a person skilled in the art, for example by contacting these with an organic or inorganic acid or base in a solvent or dispersant, or by anion exchange or cation exchange with other salts. The present invention also includes all salts of the compounds of the present invention which, owing to low physiological compatibility, are not directly suitable for use in pharmaceuticals but which can be used, for example, as intermediates for chemical reactions or for the preparation of pharmaceutically acceptable salts.

The term "substituted" preferably relates to the substitution by the above-mentioned substituents, where a plurality of different degrees of substitution are possible, unless indicated otherwise.

All physiologically acceptable salts, derivatives, solvates, solvates of salts, and stereoisomers of these compounds, including mixtures thereof in all ratios, are also in accordance with the invention.

The compounds of Formula (I) may have one or more centres of chirality. They may accordingly occur in various enantiomeric forms and be in racemic or optically active form. The invention therefore also relates to the optically active forms (stereoisomers), the enantiomers, the racemates, the diastereomers and hydrates and solvates of these compounds.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitably N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3. A method for the resolution of racemates containing ester groups (for example acetyl esters) is the use of enzymes, in particular esterases.

Furthermore, the present invention relates to pharmaceutical compositions comprising a compound of the present invention, or a prodrug compound thereof, or a pharmaceutically acceptable salt or solvate thereof as an active ingredient together with a pharmaceutically acceptable carrier.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

A pharmaceutical composition of the present invention may additionally comprise one or more other compounds as active ingredients, such as one or more additional compounds of the present invention, or a prodrug compound or other p70S6K inhibitors.

The pharmaceutical compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In one embodiment, said compounds and pharmaceutical composition are for the treatment of cancer such as brain, lung, colon, epidermoid, squamous cell, bladder, gastric, pancreatic, breast, head, neck, renal, kidney, liver, ovarian, prostate, colorectal, uterine, rectal, oesophageal, testicular, gynecological, thyroid cancer, melanoma, hematologic malignancies such as acute myelogenous leukemia, multiple myeloma, chronic myelogneous leukemia, myeloid cell leukemia, glioma, Kaposi's sarcoma, or any other type of solid or liquid tumors. Preferably, the cancer to be treated is chosen from breast, colorectal, lung, prostate or pancreatic cancer or glioblastoma.

The invention also relates to the use of compounds according to the invention for the preparation of a medicament for the treatment of hyperproliferative diseases related to the hyperactivity of p70S6K as well as diseases modulated by the p70S6K cascade in mammals, or disorders mediated by aberrant proliferation, such as cancer and inflammation.

The invention also relates to a compound or pharmaceutical composition for treating a disease related to vasculogenesis or angiogenesis in a mammal which comprises a therapeutically effective amount of a compound of the present invention, or a pharmaceutically acceptable salt, prodrug or hydrate thereof, and a pharmaceutically acceptable carrier.

In one embodiment, said compound or pharmaceutical composition is for treating a disease selected from the group consisting of tumor angiogenesis, chronic inflammatory disease such as rheumatoid arthritis, inflammatory bowel disease, atherosclerosis, skin diseases such as psoriasis, eczema, and sclerodema, diabetes, diabetic retinopathy, retinopathy of prematurity and age-related macular degeneration.

This invention also relates to a compound or pharmaceutical composition for inhibiting abnormal cell growth in a mammal which comprises an amount of a compound of the present invention, or a pharmaceutically acceptable salt or solvate or prodrug thereof, in combination with an amount of another anti-cancer therapeutic, wherein the amounts of the compound, salt, solvate, or prodrug, and of the chemotherapeutic are together effective in inhibiting abnormal cell growth. Many anti-cancer therapeutics are presently known in the art. In one embodiment, the anti-cancer therapeutic is a chemotherapeutic selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors such as cilengitide, vaccines such as BLP-25, and anti-androgens. In another embodiment the anti-cancer therapeutic is an antibody selected from the group consisting of bevacizumab, CD40-specific antibodies, chTNT-1/B, denosumab, zanolimumab, IGF1R-specific antibodies, lintuzumab, edrecolomab, WX G250, rituximab, ticilimumab, trastuzumab and cetuximab. In yet another embodiment the anti-cancer therapeutic is an inhibitor of another protein kinase, auch as Axl, Aurora A, Aurora B, dyrk2, epha2, fgfr3, igf1r, IKK2, JNK3, Vegfr1, Vegfr2, Vegfr3 (also known as Flt-4), KDR, MEK, MET, Plk1, RSK1, Src, TrkA, Zap70, cKit, bRaf, EGFR, Jak2, PI3K, NPM-Alk, c-Abl, BTK, FAK, PDGFR, TAK1, LimK, Flt-3, PDK1 and Erk.

This invention further relates to a method for inhibiting abnormal cell growth in a mammal or treating a hyperproliferative disorder that comprises administering to the mammal an amount of a compound of the present invention, or a pharmaceutically acceptable salt or solvate or prodrug thereof, in combination with surgery or radiation therapy, wherein the amounts of the compound, salt, solvate, or prodrug, is in combination with the radiation therapy effective in inhibiting abnormal cell growth or treating the hyperproliferative disorder in the mammal. Techniques for administering radiation therapy are known in the art, and these techniques can be used in the combination therapy described herein. The administration of a compound of the invention in this combination therapy can be determined as described herein. It is believed that the compounds of the present invention can render abnormal cells more sensitive to treatment with radiation for purposes of killing and/or inhibiting the growth of such cells.

Accordingly, this invention further relates to a method for sensitizing abnormal cells in a mammal to treatment with radiation which comprises administering to the mammal an amount of a compound of the present invention or pharmaceutically acceptable salt or solvate or prodrug thereof, which amount is effective is sensitizing abnormal cells to treatment with radiation. The amount of the compound, salt, or solvate in this method can be determined according to the means for ascertaining effective amounts of such compounds described herein. The invention also relates to a method for inhibiting abnormal cell growth in a mammal that comprises an amount of a compound of the present invention, or a pharmaceutically acceptable salt or solvate thereof, a prodrug thereof, or an isotopically-labeled derivative thereof, and an amount of one or more substances selected from anti-angiogenesis agents, signal transduction inhibitors, and antiproliferative agents.

In practical use, the compounds of the present invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like. In the case of oral liquid preparations, any of the usual pharmaceutical media may be employed, such as, for example, suspensions, elixirs and solutions; or carriers such as starches, sugars, microcrystalline cellulose, diluents, granulating agents, lubricants, binders, disintegrating agents and the like. In the case of oral solid preparations the composition may take forms such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of the present invention may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of the present invention are administered orally.

The effective dosage of active ingredient employed may vary depending on the particular compound employed, the mode of administration, the condition being treated and the severity of the condition being treated. Such dosage may be ascertained readily by a person skilled in the art.

When treating or preventing cancer, inflammation or other proliferative diseases for which compounds of the present invention are indicated, generally satisfactory results are obtained when the compounds of the present invention are administered at a daily dosage of from about 0.01 milligram to about 100 milligram per kilogram of animal body weight, preferably given as a single daily dose. For most large mammals, the total daily dosage is from about 0.1 milligrams to about 1000 milligrams, preferably from about 0.2 milligram to about 50 milligrams. In the case of a 70 kg adult human, the total daily dose will generally be from about 0.2 milligrams to about 200 milligrams. This dosage regimen may be adjusted to provide the optimal therapeutic response.

The invention also relates to a set (kit) consisting of separate packs of
a) an effective amount of a compound according to the invention or a physiologically acceptable salt, solvate or prodrug thereof, and
b) an effective amount of a further medicament active ingredient.

The set comprises suitable containers, such as boxes, individual bottles, bags or ampoules. The set may, for example, comprise separate ampoules, each containing an effective amount of a compound according to the invention and/or pharmaceutically usable derivatives, solvates and stereoisomers thereof, including mixtures thereof in all ratios, and an effective amount of a further medicament active ingredient in dissolved or lyophilised form.

Experimental Section

Some abbreviations that may appear in this application are as follows:
Abbreviations

| Designation | |
|---|---|
| ACN | acetonitrile |
| AcOH | Acetic acid |
| AIBN | Azobisisobutylonitrile |
| ATP | Adenosine triphosphate |
| b | Broad peak |
| Bop-Cl | Bis(2-oxo-3-oxazolidinyl)phosphinic chloride |

-continued

| Designation | |
|---|---|
| Conc. | concentrated |
| d | Doublet |
| DCM | Dichloromethane |
| DCE | dichloroethane |
| DMAP | dimethylaminopyridine |
| DMF | dimethylformamide |
| DMSO | dimethylsulfoxide |
| DIEA/DIPEA | N,N-Diisopropylethylamine |
| DTT | dithiothreitol |
| EDTA | Ethylenediaminetetraacetic acid |
| equiv./eq. | equivalents |
| Et | ethyl |
| h | hour |
| HEPES | 4-(2-hydroxyethyl)-1-piperazineethanesulfonic acid |
| HPLC | High pressure liquid chromatography |
| LC/MS | Liquid chromatography coupled to mass spectrometry |
| LiOH | Lithium hydroxide |
| m | multiplet |
| M | Molecular ion |
| m/z | Mass-to-charge ratio |
| Me | methyl |
| MeOH | methanol |
| min | minute |
| MS | Mass spectrometry |
| N | Normal (unit of concentration) |
| NaOH | Sodium hydroxide |
| NBS | N-bromosuccinimide |
| NMO | 4-methylmorpholine N-oxide |
| NMP | N-Methyl-2-pyrrolidone |
| NMR | Nuclear Magnetic Resonance |
| PG | Protecting group |
| psi | Pounds per square inch |
| q | Quartette (or quartet) |
| Rf | Retention factor |
| RT/rt | Room temperature |
| Rt. | Retention time |
| s | Singlet |
| T3P | Propylphosphonic anhydride |
| TBAF | Tetrabutylammonium fluoride |
| Tert | Tertiary |
| TEA | Triethylamine |
| TFA | Trifluoroacetic acid |
| THAB | Tetrahexylammonium bromide |
| THF | Tetrahydrofuran |
| UV | ultraviolet |
| VIS | visible |

The compounds of the present invention can be prepared according to the procedures of the following Schemes and Examples, using appropriate materials and are further exemplified by the following specific examples.

Moreover, by utilizing the procedures described herein, in conjunction with ordinary skills in the art, additional compounds of the present invention claimed herein can be readily prepared. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds.

The instant compounds are generally isolated in the form of their pharmaceutically acceptable salts, such as those described above. The amine-free bases corresponding to the isolated salts can be generated by neutralization with a suitable base, such as aqueous sodium hydrogencarbonate, sodium carbonate, sodium hydroxide and potassium hydroxide, and extraction of the liberated amine-free base into an organic solvent, followed by evaporation. The amine-free base, isolated in this manner, can be further converted into another pharmaceutically acceptable salt by dissolution in an organic solvent, followed by addition of the appropriate acid and subsequent evaporation, precipitation or crystallization.

The invention will be illustrated, but not limited, by reference to the specific embodiments described in the following schemes and examples. Unless otherwise indicated in the schemes, the variables have the same meaning as described above. Unless otherwise specified, all starting materials are obtained from commercially suppliers and used without further purifications. Unless otherwise specified, all temperatures are expressed in ° C. and all reactions are conducted at room temperature. Compounds were purified by either silica chromatography or preparative HPLC.

The present invention also relates to processes for manufacturing the compounds of Formula (I) according to the hereinafter described schemes and working examples.

Synthetic Schemes Describing Intermediate and End Product Compounds

Quinazoline bromide intermediate 1a is obtained from commercially available 2-Amino-3-methylbenzoic acid by an 8-step synthesis outlined in Scheme 1.

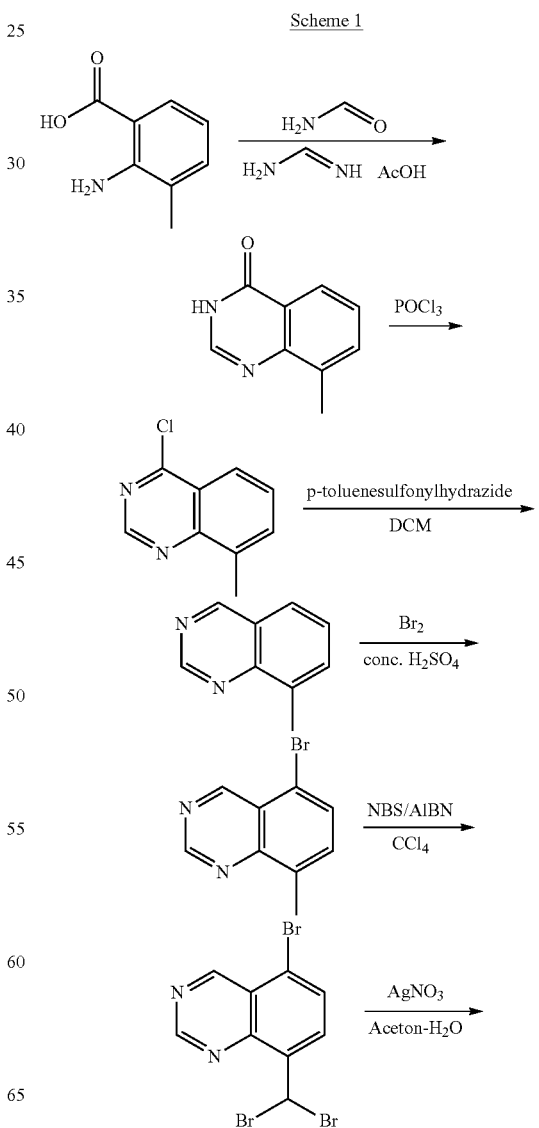

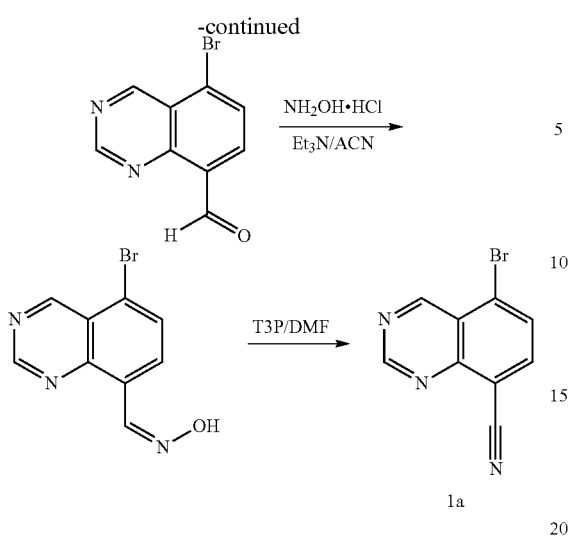

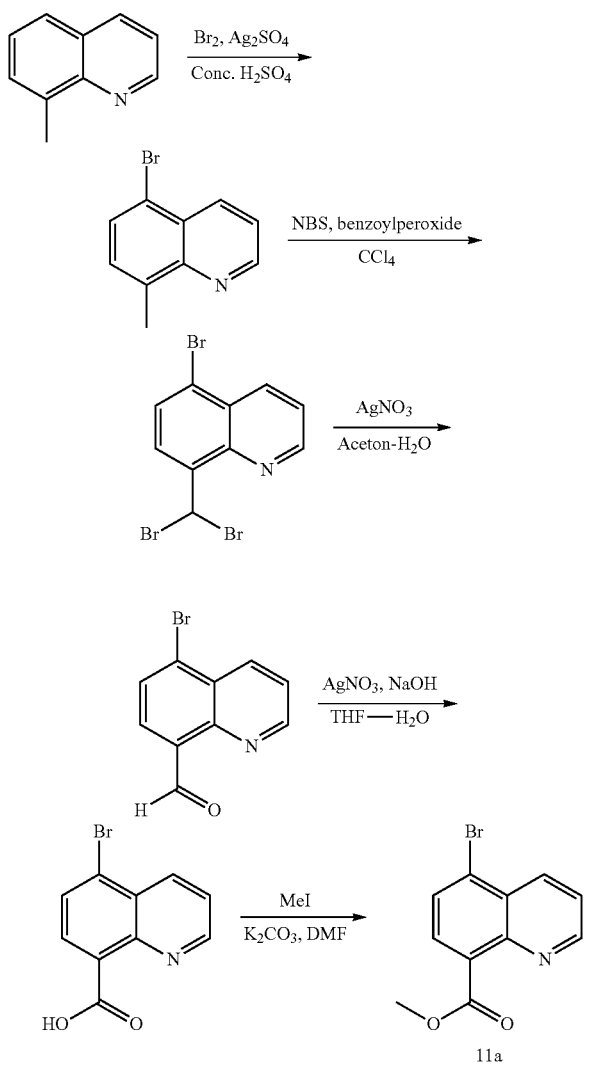

Quinoline intermediates 9a, 10a are commercially available and 11a is prepared according to the 5-step synthesis outlined in Scheme 2.

Amine intermediates are either commercially available or prepared by the following synthetic routes (Scheme 3, Scheme 4, Scheme 5 and Scheme 6).

Scheme 3

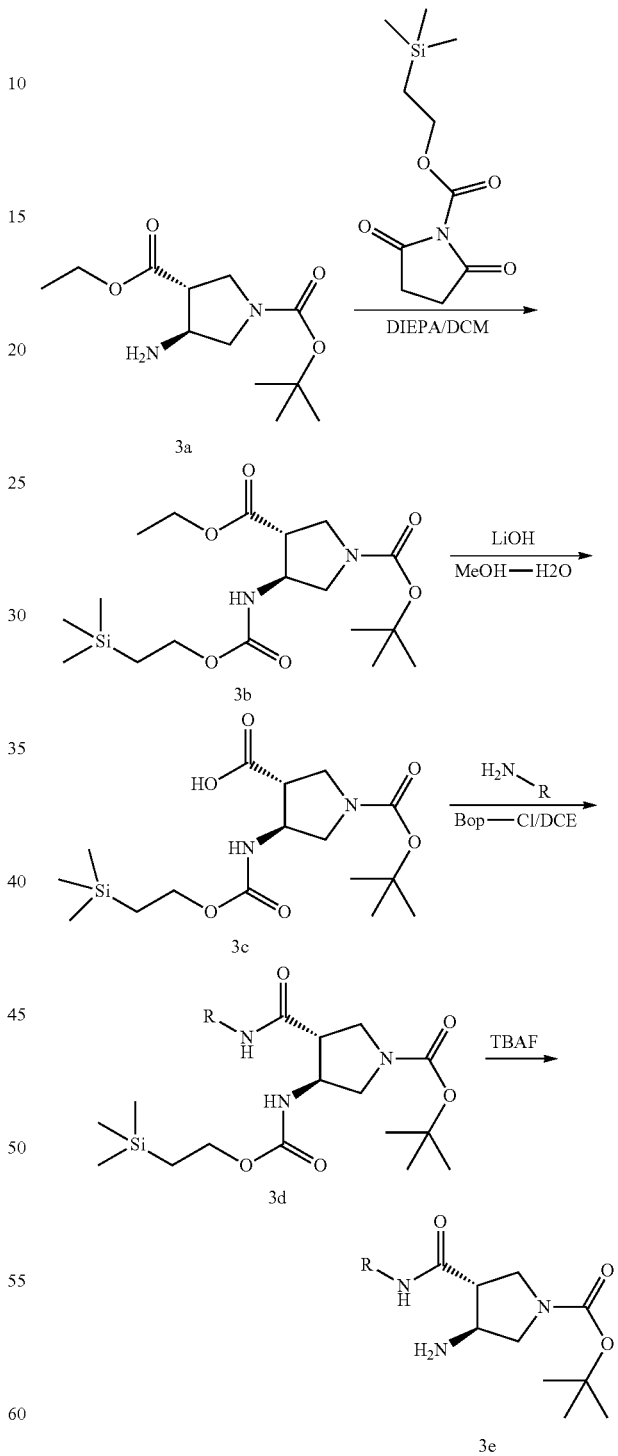

Protection of the amino group of compound 3a with Toc yields 3b. 3b was hydrolyzed to release carboxylic acid 3c. 3c is coupled with amine, followed by removing Toc protecting group to generate the amine intermediate e.

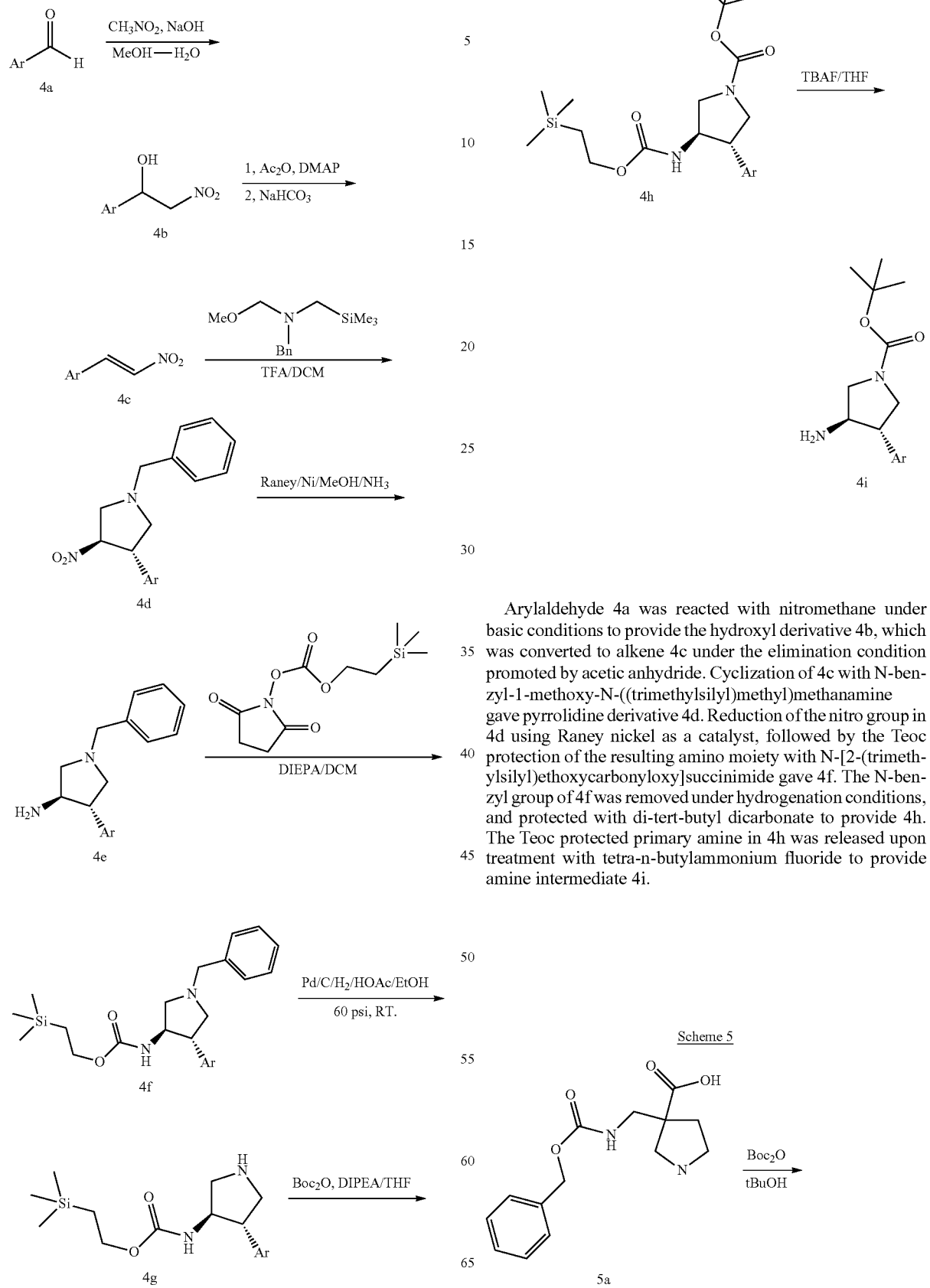

Arylaldehyde 4a was reacted with nitromethane under basic conditions to provide the hydroxyl derivative 4b, which was converted to alkene 4c under the elimination condition promoted by acetic anhydride. Cyclization of 4c with N-benzyl-1-methoxy-N-((trimethylsilyl)methyl)methanamine gave pyrrolidine derivative 4d. Reduction of the nitro group in 4d using Raney nickel as a catalyst, followed by the Teoc protection of the resulting amino moiety with N-[2-(trimethylsilyl)ethoxycarbonyloxy]succinimide gave 4f. The N-benzyl group of 4f was removed under hydrogenation conditions, and protected with di-tert-butyl dicarbonate to provide 4h. The Teoc protected primary amine in 4h was released upon treatment with tetra-n-butylammonium fluoride to provide amine intermediate 4i.

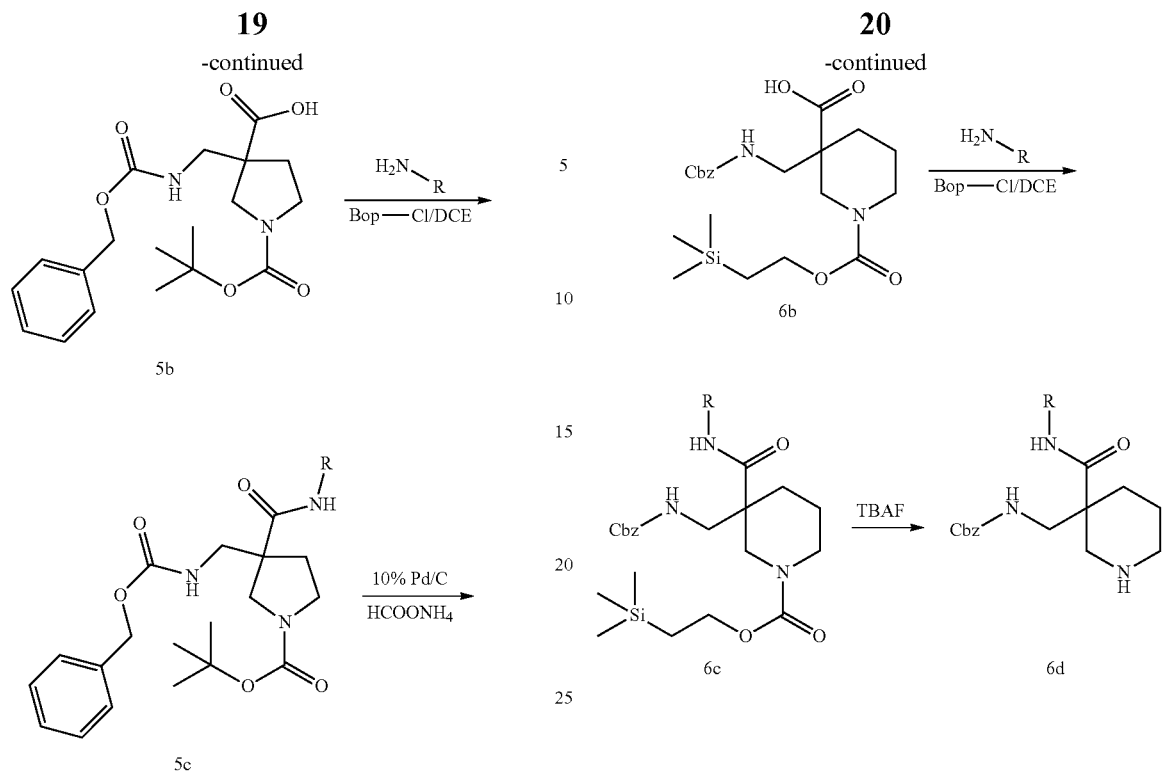

Amino group of amino acid 6a was selectively protected with Teoc, following the acid moiety coupling with amine gave amide 6c. Teoc was removed by TBAF to afford the amine intermediate 6d.

Scheme 7

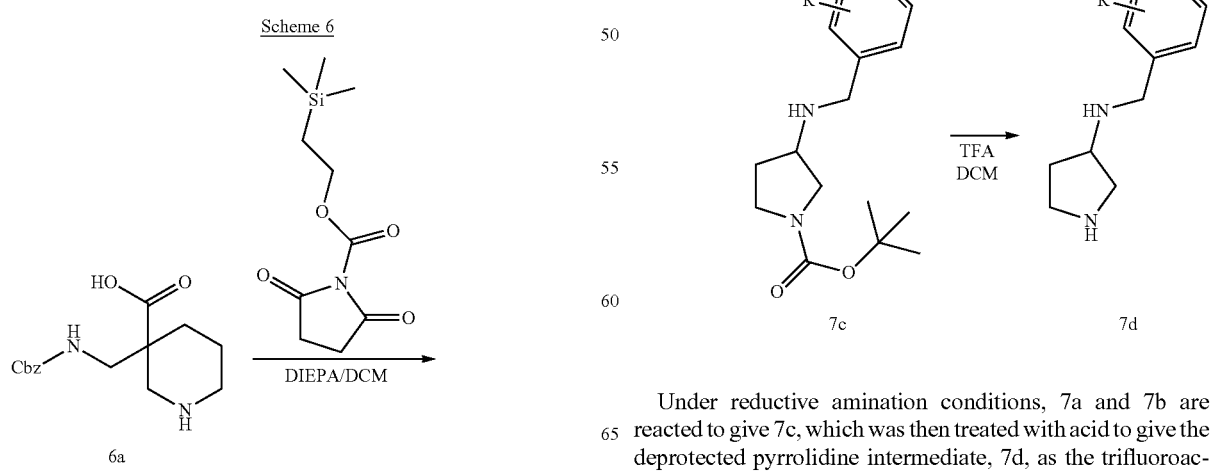

Amino acid 5a was protected with Boc to give 5b. 5b was then reacted with amine to give amide 5c. Cbz group was removed under hydrogenation condition to generate the desired amine intermediate 5d.

Scheme 6

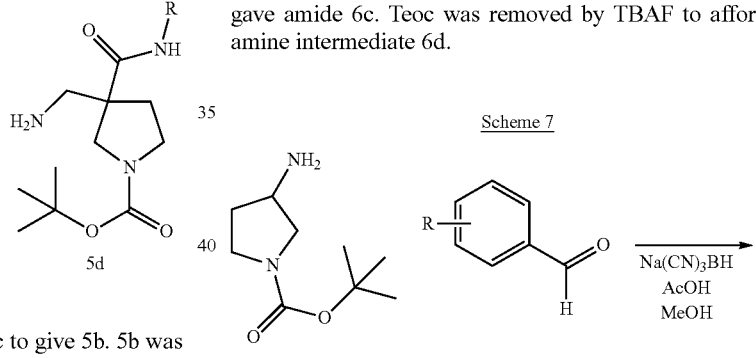

Under reductive amination conditions, 7a and 7b are reacted to give 7c, which was then treated with acid to give the deprotected pyrrolidine intermediate, 7d, as the trifluoroacetate salt.

Scheme 8

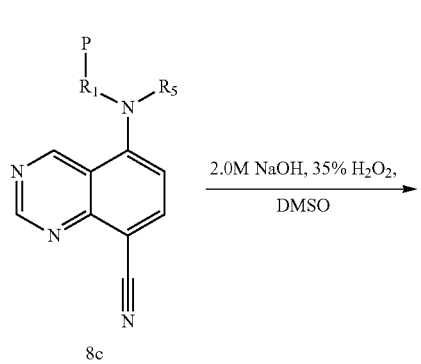

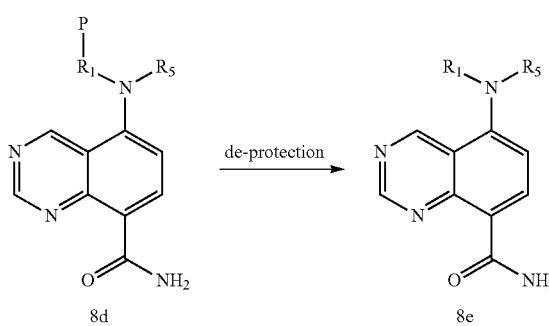

Bromide intermediate 1a is coupled with amine 8b, where P is a protecting group when it is needed, to yield 8c. Hydrolysis of nitrite intermediate 8c affords amide 8d under basic condition assistant by hydrogen peroxide, and followed by removing protecting group, gave the desired compound 8e.

Scheme 9

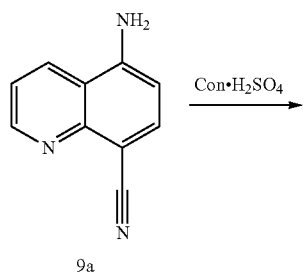

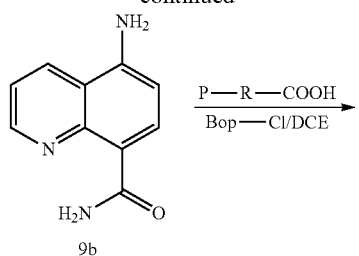

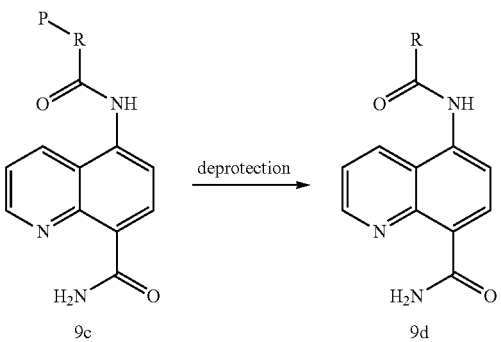

9a was oxidized hydrolysis with hot concentrated sulfuric acid to convert the nitrile to carboxylic amide 9b. 9b was coupled with carboxylic acid provided 9c. De-protection of 9c to afford 9d as the desired compound.

Scheme 10

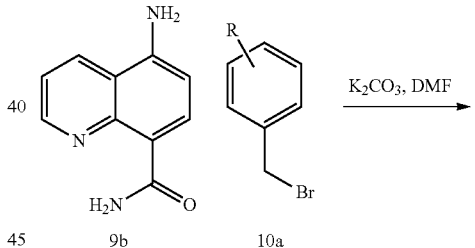

Benzyl bromides 10a were reacted with aniline 9b to yield the desired compounds 10b.

Scheme 11

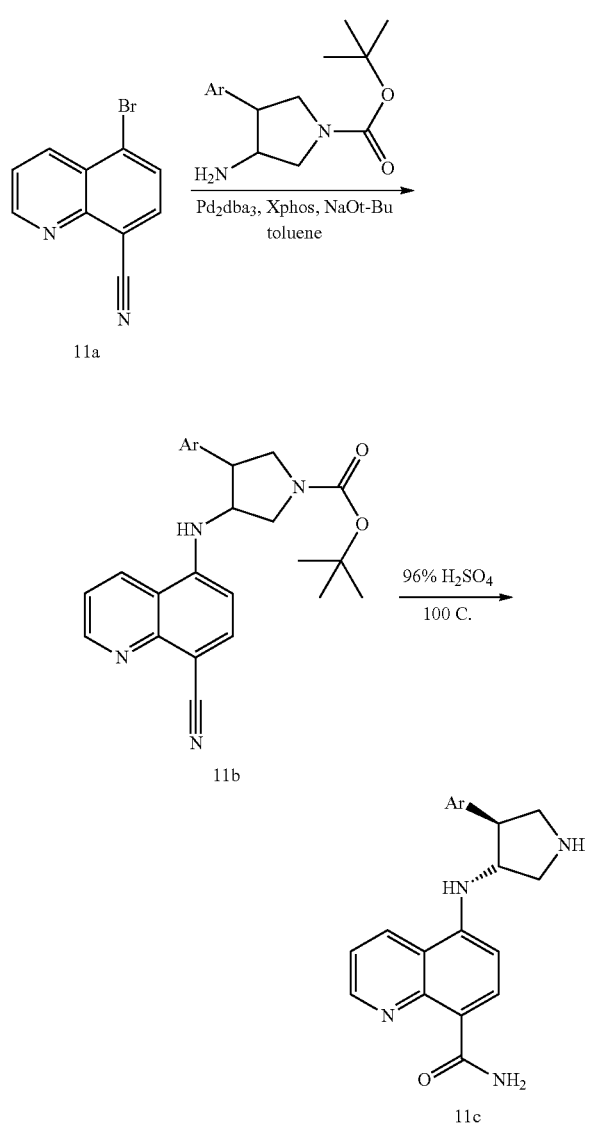

5-bromoquinoline-8-carbonitrile 11a was reacted with aminopyrrolidine derivative under Buckwald Harting cross coupling condition to give 11 b. The nitrile moiety was converted to carboxylic amide using hot concentrated sulfuric acid to afford the compound 11c.

Scheme 12

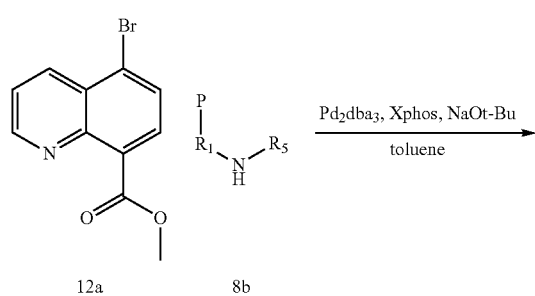

Under Buckwald Harting cross coupling condition, methyl 5-bromoquinoline-8-carboxylate 12a is reacted with the amine intermediate 8b gave 12b. 12b was treated with ammonia in methanol to yield the carboxylic amide 12c, which was then removed the protecting group to generate 12d.

Analytical Methodology

Analytical LC/MS was Performed Using the Following Three Methods:

Method A: A Discovery $C^{18}$, 5 μm, 3×30 mm column was used at a flow rate of 400 μL/min, sample loop 54, mobile phase: (A) water with 0.1% formic acid, mobile phase, (B) methanol with 0.1% formic acid; retention times are given in minutes. Method details: (I) runs on a Quaternary Pump G1311A (Agilent) with UV/VIS diode array detector G1315B (Agilent) and Finnigan LCQ Duo MS detector in ESI+ modus with UV-detection at 254 and 280 nm with a gradient of 15-95% (B) in a 3.2 min linear gradient (II) hold for 1.4 min at 95% (B) (III) decrease from 95-15% (B) in a 0.1 min linear gradient (IV) hold for 2.3 min at 15% (B).

Method B: A Waters Symmetry $C^{18}$, 3.5 μm, 4.6×75 mm column at a flow rate of 1 mL/min, sample loop 104, mobile phase (A) is water with 0.05% TFA, mobile phase (B) is ACN with 0.05% TFA; retention times are given in minutes. Methods details: (I) runs on a Binary Pump G1312A (Agilent) with UV/Vis diode array detector G1315B (Agilent) and Agilent G1956B (SL) MS detector in ESI+ mode with UV-detection at 254 and 280 nm with a gradient of 20-85% (B) in a 10 min linear gradient (II) hold for 1 min at 85% (B) (III) decrease from 20-85% (B) in a 0.2 min linear gradient (IV) hold for 3.8 min at 20% (B).

Method C: Gradient: 4.2 min/Flow: 2 ml/min 99:01-0:100 Water+0.1%(Vol.) TFA; Acetonitril+0.1%(Vol.) TFA; 0.0 to 0.2 min: 99:01; 0.2 to 3.8 min: 99:01→0:100; 3.8 to 4.2 min: 0:100; Column: Chromolith Performance RP18e; 100 mm long, 3 mm diameter; Wavelength: 220 nm.

Analytical Chiral HPLC

Analytical chiral HPLC was performed using a ChiralPak AD-H column (250×4.6 mm) from Daicel Chemical Industries, Ltd. on an Agilent 1100 Series system. The method used a 5.0 µL injection volume, with a flow rate of 1 mL/min of 100% methanol for 15 min at 25° C., and UV-detection at 254 and 280 nm.

Preparative HPLC

Preparative HPLC was performed using either a Waters Atlantis dC$_{18}$ OBD™ 10 µM (30×250 mm) column or a Waters Sunfire Prep C$_{18}$ OBD 10 µM (30×250 mm) column. The columns were used at a flow rate of 60 mL/min on a Waters Prep LC 4000 System equipped with a sample loop (10 mL) and an ISCO UA-6 UV/Vis detector. The mobile phase was drawn from two solvent reservoirs containing (A) water and (B) HPLC-grade acetonitrile. A typical preparative run used a linear gradient (e.g., 0-60% solvent B over 60 min).

EXAMPLES

The working examples presented below are intended to illustrate particular embodiments of the invention and are not intended to limit the scope of the specification or the claims in any way. These working examples describe both the synthesis of reagents used prepare the heterocyclic carboxamide compounds useful in the treatment of hyperproliferative diseases and these same heterocyclic quinazoline and quinoline carboxamide compounds.

Preparation Of The Intermediates

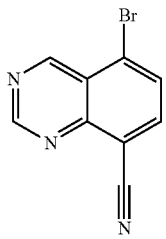 [SMILES: N#Cc1ccc(Br)c2cncnc12]

Intermediate A: 5-bromoquinazoline-8-carbonitrile

Step 1: 8-Methylquinazolin-4(3H)-one

2-Amino-3-methylbenzoic acid (100 g, 0.66 mol), formamidine acetate (206 g, 1.98 mol) and formamide (26 mL, 0.6600 mol) were mixed in a 2 L R.B fitted with Mechanical stirrer. The reaction mixture was heated at 160° C. for 16 h. The reaction completion was monitored by LCMS. After completion, the reaction mixture was cooled to was RT and diluted with 2N NaOH solution (300 mL). After stirring at the same temperature for 15 min, the reaction mixture neutralised with 1.5N HCl solution. The solid precipitated was filtered off, washed with ice cold water and dried under vacuum to yield (90 g, 86% yield) of the titled compound as an off white solid. $^1$H NMR (DMSO-d$_6$, 400 MHz) δ 12.21 (bs, 1H), 8.10 (s, 1H), 7.95-7.93 (dd, J=8.8, 7.9 Hz, 1H), 7.65-7.63 (d, J=7.9 Hz, 1H), 7.39-7.35 (t, J=15.2 Hz, 1H), 2.51 (s, 3H).

Step 2: 4-Chloro-8-methylquinazoline

POCl$_3$ (300 mL) was taken in a 2 L round bottom flask under nitrogen. To this was added 8-Methylquinazolin-4 (3H)-one (45 g) in portions. The reaction mixture refluxed at 120° C. for 12 h. Reaction completion was monitored by TLC and LCMS. After completion, the reaction mixture was cooled to RT and evaporated to dryness under reduced pressure. The resulted residue was dissolved in DCM (500 mL) and quenched slowly into an ice cold solution of saturated K$_2$CO$_3$ with constant stirring. Then the organic layer was separated and washed with brine solution, dried over sodium sulphate and concentrated under vacuum to afford (45 g, 90% yield) of the titled compound as yellow solid. This was taken for next step without further purification. $^1$H NMR (CDCl$_3$, 400 MHz) δ 9.03 (s, 1H), 8.08-8.06 (dd, J=8.9, 8.4 Hz, 1H), 7.77-7.76 (d, J=7.1 Hz, 1H), 7.59-7.56 (d, J=15.5 Hz, 1H), 2.75 (s, 3H).

Step 3: 8-Methylquinazoline

To a stirred solution of 4-Chloro-8-methylquinazoline (45 g, 0.252 mol) in DCM (700 mL) under N$_2$ was added p-toluenesulfonylhydrazide (65.9 g, 0.353 mol) in portions. The reaction mixture was heated at 45° C. for 12 h. The reaction completion was monitored by LCMS and TLC. After completion, the reaction mixture was cooled to RT, the solvent evaporated to dryness and the resulted residue redissolved in EtOH (500 mL) and added 2N NaOH solution (300 mL) and refluxed for 6 h. After confirming by LCMS, the reaction mixture was cooled to RT and extracted with MTBE (3×600 mL). The combined organic layers were washed with brine solution, dried over sodium sulfate and concentrated under vacuum. The resulted residue was filtered through column chromatography using neutralized silica gel (60-120 mesh) and pet ether/ethyl acetate as an elutent to yield (15 g, 27% yield) of the titled compound as a low melting yellow solid. $^1$H NMR (DMSO-d$_6$, 400 MHz) δ 9.54 (s, 1H), 9.31 (s, 1H), 7.97-7.94 (dd, J=8.8, 8.1 Hz, 1H), 7.87-7.84 (m, 1H), 7.65-7.62 (d, J=15.2 Hz, 1H), 2.67 (s, 3H).

Step 4: 5-Bromo-8-methylquinazoline

To a solution of 8-Methylquinazoline (10 g, 0.0694 mol) in conc.H$_2$SO$_4$ (100 mL), was added silver sulphate (34.64 g, 0.1111 mol) in portions at 0CC. To this was added Bromine (4.4 mL, 0.0832 mol) in drops. The reaction mixture was stirred at RT for 16 h. Reaction was monitored by LCMS at regular intervals. At the end of 16 h, LCMS showed 42% starting material and 51% of product. The reaction mixture was quenched with ice and basified with NH$_4$OH solution. The aqueous layer was extracted with EtOAc (4×500 mL), washed with water and brine solution. The organic layer was dried over Na$_2$SO$_4$ and concentrated under vacuum. The crude was purified by column chromatography using neutralized silica gel (60-120 mesh) and pet ether/ethyl acetate as an elutent to yield the titled compound as pale yellow liquid (51% yield). $^1$H NMR (DMSO-d$_6$, 400 MHz) δ 9.60-9.58 (s, 1H), 9.40-9.38 (s, 1H), 7.93-7.91 (d, J=7.72 Hz, 1H), 7.77-7.75 (d, J=7.72 Hz, 1H), 2.62 (s, 3H).

Step 5: 5-Bromo-8-(dibromomethyl) quinazoline

To a stirred solution of 5-Bromo-8-methylquinazoline (46 g, 0.206 mol) in CCl$_4$ (800 mL) under N$_2$, was added N-Bromosuccinimide (80.4 g, 0.451 mol) followed by AIBN (6.74 g, 0.041 mol) at RT. Then the reaction mixture was heated at 90° C. for 12 h. After completion, the reaction mixture cooled to RT, filtered off and washed with CCl$_4$. The filtrate was concentrated to dryness to yield (61 g) of the titled compound as yellow liquid. The crude product was taken as such for next step without purification. $^1$H NMR (DMSO-d$_6$, 400 MHz) δ 9.73 (s, 1H), 9.53 (s, 1H), 8.45-8.43 (d, J=8.0 4 Hz, 1H), 8.22-8.20 (d, J=8.04 Hz, 1H), 8.02 (s, 1H).

Step 6: 5-Bromoquinazoline-8-carbaldehyde

To a stirred solution of 5-Bromo-8-(dibromomethyl) quinazoline (61 g, crude mixture) in Acetone (500 mL) and water (100 mL), was added silver nitrate (61 g) in portions at 0° C. The reaction mixture was stirred at RT for 6 h. The reaction completion was confirmed by TLC. The reaction mixture was filtered off and filtrate was extracted with ethyl acetate (3×500 mL). The organic layer was washed with 10% NaHCO$_3$ solution, water and brine solution. The solvent was dried over Na$_2$SO$_4$ and concentrated under vacuum to afford the crude product with HPLC (56%) (25 g, 65%) was subjected to prep.HPLC condition: COLUMN: Xterra, C18 (19× 300 mm), 10 micron, Mobile: 0.1% TFA; B: MeOH to isolate the compound. The resulted solid was basified with NH$_4$OH and extracted with EtOAc. The organic layer was washed water. The solvent was dried over Na$_2$SO$_4$ and concentrated under vacuum to yield (6.2 g) of the titled compound as pale yellow solid. $^1$H NMR (DMSO-d$_6$, 400 MHz) 11.14 (s, 1H), 9.80 (s, 1H), 9.58 (s, 1H), 8.30-8.27 (d, J=12.3 Hz, 2H).

Step 7: 5-Bromo-quinazoline-8-carbaldehyde oxime

To a suspension solution of 5-Bromo-quinazoline-8-carbaldehyde (2400.00 mg; 10.12 mmol; 1.00 eq.) in acetonitrile (10 ml), hydroxylamine hydrogen chloride (773.90 mg; 11.14 mmol; 1.10 eq.) was added, followed by triethylamine (1.57 ml; 11.14 mmol; 1.10 eq.). The reaction mixture was stirred at 100° C. for 1 hr, LCMS showed MS 270/272 (M+18). The reaction was cooled, filtrate and washed with ether to collect products-Bromo-quinazoline-8-carbaldehyde oxime 3000 mg, yield 117% (1HNMR showed contained 1eq triethyamine HCl salt).

Step 8: 5-bromoquinazoline-8-carbonitrile

To a solution of 5-Bromo-quinazoline-8-carbaldehyde oxime (3000.00 mg; 11.90 mmol; 1.00 eq.) in DMF (15 ml) was added 2,4,6-Tripropyl-[1,3,5,2,4,6]trioxatriphosphinane 2,4,6-trioxide (10.42 ml; 17.85 mmol; 1.50 eq.) 50% in DMF. The resulting mixture was stirred at 100° C. for 45 min, LCMS showed major peak (MS: 252/254, 234/236) and small (MS: 208/209). The reaction mixture was cooled, poured into water, extracted with EtOAc, dried and concentrated to yield sticky solid, which was washed with ether to collected the title product (1665 mg. yield 59.6%). LC-MS (232/234 and 250/252).

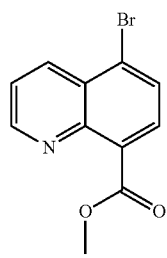

Intermediate B: Methyl 5-bromoquinoline-8-carboxylate

Step 1: 5-Bromo-8-methylquinoline

To a solution of 8-Metyl quinoline (30 g, 0.209 mol) in Conc.H$_2$SO$_4$ (300 ml) was added Silver sulphate (97.98 g, 0.314 mol) in lots at 0° C. and followed by Bromine (10.74 ml, 0.209 mol) drop wise for 10 min. After addition of Bromine, the reaction mixture was stirred at RT for 4 h and the reaction completion was confirmed by TLC. After completion of reaction the reaction mixture was quenched with ice and basified with NH$_4$OH solution and extracted with ethyl acetate. The organic layer was washed with water, brine solution and dried over anhydrous sodium sulphate and concentrated to afford (43 g, 92.4% yield) as dark brown liquid. The crude product was as such taken for next step without further purification. $^1$H NMR (DMSO-d$_6$ 400 MHz): δ 8.97-8.96 (dd, J=4.16, 5.8 Hz, 1H), 8.45-8.42 (dd, J=8.56, 10.2 Hz, 1H), 7.81-7.79 (d, J=7.68 Hz, 1H), 7.67-7.64 (dd, J~8.52, 12.64 Hz, 1H), 7.53-7.51 (dd, J=7.64, 8.52 Hz, 1H), 2.66 (s, 3H).

Step 2: 5-Bromo-8-(dibromomethyl)quinoline

To a solution of 5-Bromo-8-methylquinoline (86 g, 0.387 mol) in CCl$_4$ (700 ml) was added N-Bromosuccinamide (144 g, 0.813 mol), Followed by Benzoylperoxide (8.6 g) at RT and the reaction mixture was heated for 90° C. for 12 h. The reaction completion was confirmed by TLC. After completion of reaction, the reaction mixture was filtered and concentrated to afford (140 g, 95% yield) as pale orange solid. The crude product was as such taken for next step without further purification. $^1$H NMR (DMSO-d$_6$ 400 MHz): δ 9.1-9.08 (dd, J=4.16, 5.8 Hz, 1H), 8.59-8.57 (dd, J=8.56, 10.2 Hz, 1H), 8.25-8.23 (d, J=8.04 Hz, 1H), 8.16-8.11 (t, J=19.08 Hz, 2H), 7.82-7.79 (dd, J=8.6, 12.8 Hz, 1H).

Step 3: 5-Bromoquinoline-8-carbaldehyde

To a solution of 5-Bromo-8-(dibromomethyl)quinoline (75 g, 0.197 mol) in Acetone (400 ml), Water (100 ml) was added Silvernitrate (75 g) at 0° C. in lots for 10 min and this reaction mixture was stirred at RT for 6 h. The reaction completion was confirmed by TLC. After completion of reaction the reaction mixture was filtered and the filterate was extracted with MTBE (1000 ml). The organic layer was washed with 10% NaHCO$_3$ solution water, brine and the organic layer was dried over sodium sulphate and concentrated to afford the title compound as off white solid (15 g, 32% yield). $^1$H NMR (DMSO-d$_6$ 400 MHz): δ 11.272-11.27 (s, 1H), 9.17-9.15 (dd, J=4.2, 5.8 Hz, 1H), 8.64-8.62 (dd, J=8.6, 10.3 Hz, 1H), 8.17-8.15 (d, J=7.84, 1H), 8.09-8.07 (d, J=7.88 Hz, 1H), 7.85-7.82 (dd, J=8.64, 12.84 Hz, 1H).

Step 4: 5-Bromoquinoline-8-carboxylic acid

To a solution of 5-Bromoquinoline-8-carbaldehyde (10 g, 0.039 mol) in THF (300 ml) was added aqueous NaOH (30 g) and followed by silver nitrate (10.79 g, 0.0635 mol) lot wise at RT for 10 min and this reaction mixture was stirred at RT for 30 min. The reaction completion was confirmed by TLC. After completion of reaction the reaction mixture was filtered. The black solid was wanded with THF, MeOH and DMF (50 ml each). (Note: Product was not soluble in any of these solvents!! The filtrate and washings were discarded). The black solid was dried to afford the title compound (crude ~30 g). The crude product was as such taken for the next step. $^1$H NMR (DMSO-d$_6$, 400 MHz): δ 8.92-8.91 (dd, J=4.12, 5.8 Hz, 1H), 8.49 (s, 1H), 8.46-8.44 (dd, J=8.56, 10.2 Hz, 1H), 7.83-7.81 (dd, J=7.6, Hz, 1H), 7.63-7.6 (dd, J=8.52, 12.68 Hz, 1H), 7.46-7.44 (d, J=7.6 Hz, 1H).

Step 5: Methyl 5-bromoquinoline-8-carboxylate

To a solution of 5-Bromoquinoline-8-carboxylic acid (30 g, 0.119 mol, crude) in DMF (400 ml) was added potassium carbonate (41.12 g, 0.297 mol) and MeI (22.3 ml, 0.357 mol) at RT. The reaction mixture was stirred at RT for 12 h and the reaction completion was confirmed by TLC. After completion of reaction the reaction mixture was filtered and evaporated. The reaction mixture was basified with 10% NaHCO$_3$ and extracted with ethyl acetate. The organic layer was washed with water, brine and dried over sodium sulphate and concentrated to afford the title compound as brown liquid (4.6 g). LCMS: Mass found (M+, 268). $^1$H NMR (DMSO-d$_6$ 400 MHz): δ 9.04-9.02 (dd, J=3.92, 5.68, Hz, 1H), 8.58-8.56 (m, 1H), 8.05-8.03 (d, J=7.72 Hz, 1H), 7.87-7.86 (d, J=7.76 Hz, 1H), 7.78-7.75 (dd, J=8.6, 12.8 Hz, 1H), 3.91 (s, 3H).

Representative Synthesis of Intermediate C (Scheme 4)

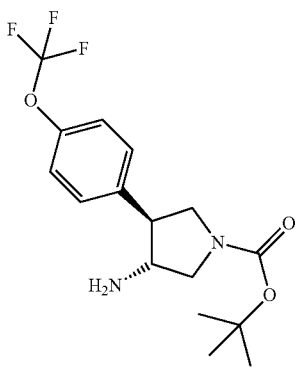

tert-butyl 3-amino-4-(4-(trifluoromethoxy)phenyl) pyrrolidine-1-carboxylate (trans, racemic)

Step 1: 1-(3-trifuoromethoxy-phenyl)-2-nitro-ethanol

A solution of 3-fluoromethoxybenzaldehyde (21.37 ml; 201.43 mmol; 1.00 eq.) and nitromethane (13.06 ml; 241.71 mmol; 1.20 eq.) in MeOH (40 ml) was cooled to −10° C. A solution of NaOH (8.46 g; 211.50 mmol; 1.05 eq.) in H$_2$O (20 ml) was added over 10 min, keeping the temperature below −5° C. The reaction mixture was stirred at −5° C. for 15 min, during which the reaction solution solidified as a white solid. The reaction mixture was warmed to 0° C., and diluted with H$_2$O (150 ml). Upon dissolution of all of the solids, HCl (4M, 100 ml) was added. The reaction mixture was extracted with DCM (300 ml×2). The combined extracts were washed with brine and concentrated to provide the desired 1-(3-trifuoromethoxy-phenyl)-2-nitro-ethanol 34.8 g, yield 93%.

Step 2: 1-trifluoromethoxy-3-((E)-2-nitro-vinyl)-benzene

N,N-Dimethylpyridin-4-amine (2.30 g; 18.80 mmol) was added to a solution of 1-(3-fluoromethoxyphenyl)-2-nitroethanol (34.80 g; 187.95 mmol) in acetic anhydride (35.53 ml; 375.90 mmol) at 0° C., and stirred at RT for 72 h. The reaction mixture was quenched by pouring into a vigorously stirred satd. NaHCO$_3$ solution (400 mL). The desired intermediate was extracted with ethyl acetate (3×100 mL). The organic extracts were washed with satd. NaHCO$_3$, brine, dried over MgSO$_4$, filtered, and concentrated to provide the desired 1-trifluoromethoxy-3-((E)-2-nitro-vinyl)-benzene 26.0 g, yield 83%.

Step 3: Trans-1-Benzyl-3-(3-trifluoromethoxy-phenyl)-4-nitro-pyrrolidine

N-benzyl-1-methoxy-N-[(trimethylsilyl)methyl]methanamine was added to a solution of 1-trifluoromethoxy-3-((E)-2-nitro-vinyl)-benzene (6.00 g; 35.90 mmol) in DCM (50 ml). The reaction solution was cooled to 0° C., TFA (0.30 ml; 3.95 mmol) was added dropwise, and stirred overnight at RT. The reaction solution was washed with H$_2$O and brine, dried over MgSO$_4$, filtered, and concentrated. The crude material was purified via Biotage (340 g column) eluting with 5% EtOAc in hexane to provide the desired product 5.5 g, yield 51%.

Step 4: (Trans-1-Benzyl-4-(3-trifluromethoxy-phenyl)-pyrrolidin-3-ylamine

Trans-1-benzyl-3-(3-trifluoromethoxyphenyl)-4-nitropyrrolidine (5.50 g; 18.31 mmol) was dissolved in MeOH (300 mL). NH$_3$ (30 ml, 2.0M in MeOH) was added, and the solution was passed through the H cube (flow 1.5 min/min, full H$_2$, at 50° C.). The reaction solution was concentrated to provide (Trans-1-Benzyl-4-(3-trifluromethoxy-phenyl)-pyrrolidin-3-ylamine 4.6 g, yield 92%.

Step 5: 2-(trimethylsilyl)ethyl [trans-1-Benzyl-4-(3-trifluoromethoxy-phenyl)-pyrrolidin-3-yl]-carbamate 1-({[2-(Trimethylsilyl)ethoxy]carbonyl}oxy)pyrrolidine-2,5-dione (4.5 g; 17.37 mmol) was added to a solution of trans-1-benzyl-4-(3-trifluoromethoxyphenyl) pyrrolidinyl-3-amine (4.5 g; 16.87 mmol) and DIEA (4.5 ml; 25.30 mmol) in DCM (50 ml) at 0° C. The reaction mixture was then warmed to RT and stirred for 1 hr at RT. The reaction solution was washed with brine, dried over MgSO$_4$, filtered, and concentrated. The crude material was purified by Biotage eluting with a gradient of 30 to 60% EtOAc in hexane to provide the title compound 6.0 g, yield 99%.

Step 6: 2-(trimethylsilyl)ethyl [trans-4-(3-trifluoromethoxy-phenyl)-pyrrolidin-3-yl]-carbamate AcOH (2 mL) was added to a solution of 2-(trimethylsilyl) ethyl [trans-benzyl-4-(3-trifluoromethoxyphenyl)pyrrolidin-3-yl]carbamate (2.50 g; 6.03 mmol) in EtOH (150 ml). Pd/C (1.25 g, wet, 10% Pd) was then added, and the reaction mixture was put on a par shaker (60 Psi), and reacted for 2 h. The reaction mixture was filtered, and the filtrate was concentrated to provide the title compound (1.96 g, quantitative yield).

Step 7: Tert-butyl trans-3-(3-trifluoromethoxyphenyl)-4-({[2-(trimethylsilyl)ethoxy]carbonyl}amino)-pyrrolidine-1-carboxylate Di-tert-butyl dicarbonate (1.27 g; 5.82 mmol) was added to a solution of 2-(trimethylsilyl)ethyl [trans-4-(3-fluoromethoxyphenyl)pyrrolidin-3-yl]carbamate (1.80 g; 5.55 mmol) and DIEA (2.2 ml; 12.26 mmol) in DCM (100 ml) and stirred overnight at RT. The reaction mixture was concentrated, and the crude product was purified via Biotage eluting with a gradient of 20 to 60% EtOAc in hexanes to provide the title compound 2.0 g, yield 85%.

Step 8: tert-butyl 3-amino-4-(4-(trifluoromethoxy) phenyl)pyrrolidine-1-carboxylate (trans, racemic)

Tert-butyl trans-3-(3-trifluoromethoxyphenyl)-4-({[2-(trimethylsilyl)ethoxy]carbonyl}amino)-pyrrolidine-1-carboxylate (2.4 g; 5.76 mmol) and N,N,N-tributylbutan-1-aminium fluoride (20.00 ml; 1.00 M; 20.00 mmol) was dissolved in MeOH, and stirred overnight at RT. The crude product was purified via Biotage eluting with a gradient of 5 to 10% MeOH in DCM to provide title compound (1.61 g, yield 79%). LC-MS (M+H=346, obsd=347). $^1$HNMR (DMSO-d6) δ 1.39 (s, 9H), 1.55 (s, 1H), 2.90-2.99 (m, 2H), 3.24-3.26 (m, 1H), 3.33-3.37 (m, 1H), 3.55-3.57 (m, 1H), 3.60-3.68 (m, 1H), 3.70-3.72 (m, 1H), 7.05-7.06 (m, 1H), 7.13-7.15 (m, 2H), 7.35-7.36 (m, 1H).

Representative Synthesis of Intermediate D (Scheme 6)

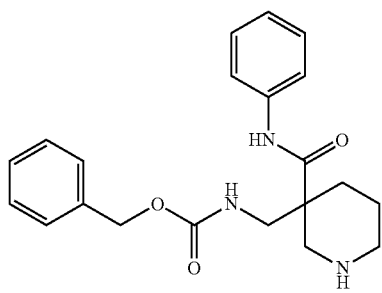 [SMILES: O=C(NCC1(C(=O)Nc2ccccc2)CCCNC1)OCc1ccccc1]

Benzyl((3-(phenylcarbamoyl)piperidin-3-yl)methyl) carbamate (racemic)

Step 1: 3-((((benzyloxy)carbonyl)amino)methyl)-1-((2-(trimethylsilyl)ethoxy)-carbonyl)piperidine-3-carboxylic acid To 3-(Benzyloxycarbonylamino-methyl)-piperidine-3-carboxylic acid hydrochloride (2000.00 mg; 6.08 mmol; 1.00 eq.) in DME (60 ml) was added DIEA (3.82 ml; 21.29 mmol; 3.50 eq.). After stirring for 15 mins, 3-trimethylsilanyl-propionic acid 2,5-dioxo-pyrrolidin-1-yl ester was added (1628.18 mg; 6.69 mmol; 1.10 eq.). The reaction mixture was stirred overnight at RT. Added another 50 ml of DME to the reaction solution, then washed with 1% citric acid, brine, dried and concentrated to yield the residue showed clean ms as the title compound (2462 mg, yield 85%), which was directly used for the next step reaction.

Step 2: 2-(trimethylsilyl)ethyl 3-((((benzyloxy)carbonyl)amino)methyl)-3-(phenylcarbamoyl)piperidine-1-carboxylate To a solution of 3-((((benzyloxy)carbonyl)amino)methyl)-1-((2-(trimethylsilyl)ethoxy)carbonyl)piperidine-3-carboxylic acid (2462.00 mg; 5.64 mmol; 1.00 eq.) in DCE (4.0 ml) bis(2-oxo-1,3-oxazolidin-3-yl)phosphinic chloride (1435.59 mg; 5.64 mmol; 1.00 eq.) was added. After stirring for 15 mins at RT, DIEA (1.52 ml; 8.46 mmol; 1.50 eq.) and Phenylamine (525.18 mg; 5.64 mmol; 1.00 eq.) were added. The reaction mixture was stirred overnight at RT. The reaction mixture was added 50 ml of DCM, washed with brine, dried and concentrated. The residue was subjected to SNAP column (100 g) for purification, eluted with 20-50% EtOAc in hexane to yield the title compound (2600 mg, yield 90.1%)

Step 3: benzyl((3-(phenylcarbamoyl)piperidin-3-yl) methyl)carbamate

The reaction mixture of 2-(trimethylsilyl)ethyl 3-((((benzyloxy)carbonyl)amino)methyl)-3-(phenylcarbamoyl)piperidine-1-carboxylate (1200.00 mg; 2.35 mmol; 1.00 eq.) and TBAF (10.00 ml; 9.38 mmol; 4.00 eq.) in THF was stirred at RT overnight. The crude was purified by prep HPLC to afford the title compound (600 mg, 69.6%)

Representative Synthesis of Intermediate E (Scheme 5)

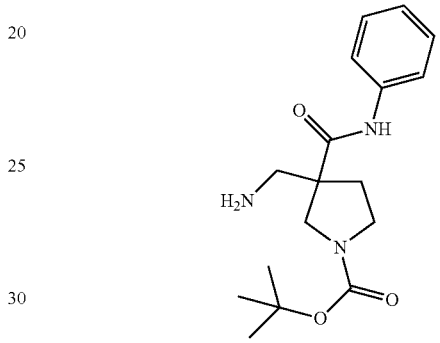

tert-Butyl 3-aminomethyl-3-phenylcarbamoyl-pyrrolidine-1-carboxylate (racemic)

Step 1: 3-(Benzyloxycarbonylamino-methyl)-pyrrolidine-1,3-dicarboxylic acid 1-tert-butyl ester A reaction mixture of 3-(benzyloxycarbonylamino-methyl)-pyrrolidine-3-carboxylic acid, hydrochloride (2000.00 mg; 6.35 mmol; 1.00 eq.) and di-tert-butyl dicarbonate (1.77 ml; 8.26 mmol; 1.30 eq.) was suspended in t-BuOH (25.00 ml) and then treated with aqueous 2N NaOH (3.97 ml; 7.94 mmol; 1.25 eq.). The reaction mixture was warmed to 75° C. (immediate effervescence was observed) for 2 h. The reaction mixture was concentrated. The residue was dissolved in EtOAc (100 ml) and washed with water and brine, dried over MgSO$_4$, concentrated and dried to afford 3-(benzyloxycarbonylamino-methyl)-pyrrolidine-1,3-dicarboxylic acid 1-tert-butyl ester (2200 mg, 89.4%).

Step 2: 3-(Benzyloxycarbonylamino-methyl)-3-phenylcarbamoyl-pyrrolidine-1-carboxylic acid tert-butyl ester To a solution of 3-(benzyloxycarbonylamino-methyl)-pyrrolidine-1,3-dicarboxylic acid 1-tert-butyl ester (2200.00 mg; 5.81 mmol; 1.00 eq.) in DCE (40.0 ml), bis(2-oxo-1,3-oxazolidin-3-yl)phosphinic chloride (1627.95 mg; 6.40 mmol; 1.10 eq.) was added. After stirring for 15 mins. DIEA (1.25 ml; 6.98 mmol; 1.20 eq.) and phenylamine (595.55 mg; 6.40 mmol; 1.10 eq) were added. The reaction mixture was stirred overnight at RT. DCM (100 ml) was added. The solution was washed with brine, dried and concentrated to give the crude product, which was subjected for biotage for purification (20-50% EtOAc in hexane) to afford the title compound (1800 mg, 68.3%).

Step 3: tert-Butyl 3-aminomethyl-3-phenylcarbamoyl-pyrrolidine-1-carboxylate To 3-(benzyloxycarbonylamino-methyl)-3-phenylcarbamoyl-pyrrolidine-1-carboxylic acid tert-butyl ester (1200.00 mg; 2.65 mmol; 1.00 eq.) in 30 ml of methanol was added of ammonium formate (1668.40 mg; 26.46 mmol; 10.00 eq.) and 10% Pd/C (wet) 1.2 g. The mixture was stirred at 65° C. for 1 hr and then filtered. The filtrate was concentrated to give the crude, which was dissolved in DCM and washed with 5% NaHCO₃, brine, dried and concentrated to afford the title compound (820 mg, 97%).

Representative Synthesis of Intermediate F (Scheme 3)

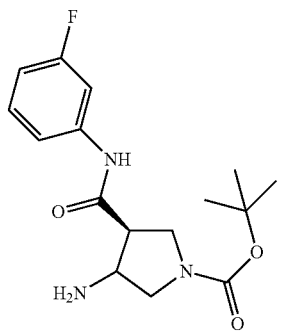 [SMILES: CC(C)(C)OC(=O)N1CC(N)[C@@H](C(=O)Nc2cccc(F)c2)C1]

tert-butyl 3-amino-4-((3-fluorophenyl)carbamoyl)pyrrolidine-1-carboxylate (racemic)

Step 1: 4-(2-Trimethylsilanyl-ethoxycarbonylamino)-pyrrolidine-1,3-dicarboxylic acid 1-tert-butyl ester 3-ethyl ester A reaction mixture of 4-(2-Trimethylsilanyl-ethoxycarbonylamino)-pyrrolidine-1,3-dicarboxylic acid 1-tert-butyl ester 3-ethyl ester (4443.00 mg; 11.04 mmol; 1.00 eq.), LiOH.H2O (1389.45 mg; 33.11 mmol; 3.00 eq.) in water (16.50 ml) and MeOH (16.50 ml) were stirred at 45° C. overnight. After removing partial of solvents, the mixture was extracted with DCM, washed with 5% citric acid, then brine, dried and concentrated to yield light yellow oil as the title compound (3200 mg, 77.4%).

Step 2: 3-(3-Fluoro-phenylcarbamoyl)-4-(2-trimethylsilanyl-ethoxycarbonylamino)-pyrrolidine-1-carboxylic acid tert-butyl ester To a solution of 4-(2-trimethylsilanyl-ethoxycarbonylamino)-pyrrolidine-1,3-dicarboxylic acid 1-tert-butyl ester (3200.00 mg; 8.54 mmol; 1.00 eq.) in DCE (40.0 ml), bis(2-oxo-1,3-oxazolidin-3-yl)phosphinic chloride (2392.68 mg; 9.40 mmol; 1.10 eq.) was added. After stirring for 15 mins. DIEA (1.69 ml; 9.40 mmol; 1.10 eq) and 3-fluoro-phenylamine (1044.40 mg; 9.40 mmol; 1.10 eq) were added. The reaction mixture was stirred overnight at 45° C. The reaction solution was diluted with EtOAc, washed, dried and concentrated to give the crude product, which was subjected for SNAP (100 g) column for purification (eluted with 20-50% EtOAc in hexane) to afford the title compound (1700 mg, 42.5%).

Step 3: tert-Butyl 3-amino-4-(3-fluoro-phenylcarbamoyl)-pyrrolidine-1-carboxylate To 3-(3-Fluoro-phenylcarbamoyl)-4-(2-trimethylsilanyl-ethoxycarbonylamino)-pyrrolidine-1-carboxylic acid tert-butyl ester (1700.00 mg; 3.64 mmol; 1.00 eq.) was added of TBAF (2851.67 mg; 10.91 mmol; 3.00 eq.) (1.0M in THF 11 ml). The resulting mixture was stirred overnight. The reaction mixture was poured into water, washed with brine, then 5% NaHCO₃, brine, dried and concentrated to give the crude, which was added of ether (5 ml). The precipitated white solid was filtered to afford the title compound (710 mg, 60.4%).

Representative Synthesis of Intermediate G (Scheme 7)

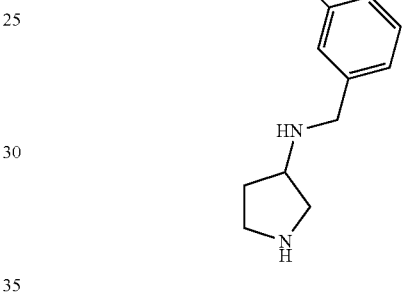

N-(3,4-dichlorobenzyl)pyrrolidin-3-amine (racemic)

Step 1: tert-Butyl 3-((3,4-dichlorobenzyl)amino) pyrrolidine-1-carboxylate

A solution of tert-butyl 3-aminopyrrolidine-1-carboxylate (1.5 g; 8.05 mmol; 1.00 eq and 3,4-dichlorobenzaldehyde (1339.00 mg; 7.65 mmol; 0.95 eq.) in methanol (10.00 ml) and acetic acid (1.00 ml) was stirred for 30 minutes at ambient temperature, then sodium cyanoborohydride (9.66 ml; 9.66 mmol; 1.20 eq.) was added. The reaction mixture was stirred for an additional 12 hours at ambient temperature at which time the reaction was quenched by pouring into aqueous ammonia (30 mL). The resulting inorganic precipitate was filtered off, and washed with dichloromethane (50 mL). The organic layer was separated and the remaining aqueous layer was extracted with dichloromethane (50 mL×3). The combined organic extracts were washed with brine (50 mL), dried over sodium sulfate, filtered and concentrated in vacuo. The resultant oil is purified under flash chromatography using silicon column with gradient of ethyl acetate in hexanes to afford the desired intermediate, tert-Butyl 3-((3,4-dichlorobenzyl)amino)pyrrolidine-1-carboxylate (2.47 g; 7.16 mmol; 88.9%), as a clear viscous oil. LC-MS (M+H=346, obsd.=288 (M-57))

Step 2: N-(3,4-dichlorobenzyl)pyrrolidin-3-amine

To a solution of tert-Butyl 3-((3,4-dichlorobenzyl)amino) pyrrolidine-1-carboxylate (100 mg; 0.29 mmol; 1.00 eq) in dichloromethane (3 mL) is added trifluoroacetic acid (0.04 mL; 0.58 mmol; 2.00 eq). The reaction flask is equipped with argon inlet and stirred until deemed complete as determined by TLC (10% methanol in dichloromethane). Upon completion, the solution is concentrated en vacuo to a dry residue, then taken up with dichloromethane and concentrated (×3) to give the desired Intermediate G as the TFA salt in quantitative yield. LC-MS (M+H=246, obsd.=246).

Example Compounds According to Formula (I)

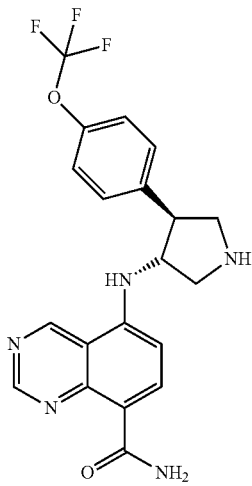

Example 1

5-((4-(4-(trifluoromethoxy)phenyl)pyrrolidin-3-yl)amino)quinazoline-8-carboxamide (trans_racemic)

Step 1: Tert-butyl 3-((8-cyano-quinazolin-5-yl)amino)-4-(4-(trifluoromethoxy)phenyl)pyrrolidine-1-carboxylate (trans_racemic)

A reaction mixture of Intermediate A (100.00 mg; 0.43 mmol; 1.00 eq.), tert-butyl 3-amino-4-(4-(trifluoromethoxy)phenyl)pyrrolidine-1-carboxylate (trans_racemic) (155.38 mg; 0.45 mmol; 1.05 eq.) and DIEA (0.15 ml; 0.85 mmol; 2.00 eq.) in NMP (2 ml) was stirred at 120° C. for overnight. The reaction mixture was purified by pre-HPLC to give the title compound (120 mg, 56.8%).

Step 2: Tert-butyl 3-((8-carbamoylquinazolin-5-yl)amino)-4-(4-(trifluoromethoxy)phenyOpyrrolidine-1-carboxylate (trans_racemic)

Tert-butyl 3-(8-Cyano-quinazolin-5-ylamino)-4-(4-trifluoromethoxy-phenyl)-pyrrolidine-1-carboxylate (100.00 mg; 0.20 mmol; 1.00 eq.) was stirred with aqueous 2.0M NaOH (1 ml; 2.00 mmol; 10.00 eq.) and aqueous 35% $H_2O_2$ (0.19 ml; 2.00 mmol; 10.00 eq.) in DMSO (8 ml) at 40° C. overnight. The crude was purified by pre-HPLC to yield the title compound (58 mg, 56.0%).

Step 3: 5-((4-(4-(trifluoromethoxy)phenyl)pyrrolidin-3-yl)amino)quinazoline-8-carboxamide (trans_racemic)

To Tert-butyl 3-((8-carbamoylquinazolin-5-yl)amino)-4-(4-(trifluoromethoxy)phenyl)pyrrolidine-1-carboxylate (trans_racemic) 58.0 mg was added 1 ml of methanol, and 1 ml of 4.0M HCl in dioxane. The resulting mixture was stirred at RT for 3 hrs. The solvents were removed to give the crude product, which was treated with acetonitrile to yield Example 1 (42 mg) as HCl salt. LC-MS (M+H=418, obsd.=418). $^1$HNMR: (DMSO)$^6$10.12 (s, 1H), 9.80 (s, 1H), 9.67 (s, 1H), 9.32 (1s, 1H), 8.49-8.51 (d, 2H), 8.05-8.07 (d, 1H), 7.67-7.70 (d, 2H), 7.38-7.40 (d, 2H), 6.72-6.7 (d, 1H), 4.65 (t, 1H), 3.77-3.81 (m, 3H), 3.35-3.40 (m, 1H), 3.15-3.25 (m, 1H), 3.20 (s, 1H).

P70S6K IC$_{50}$: 23 nM

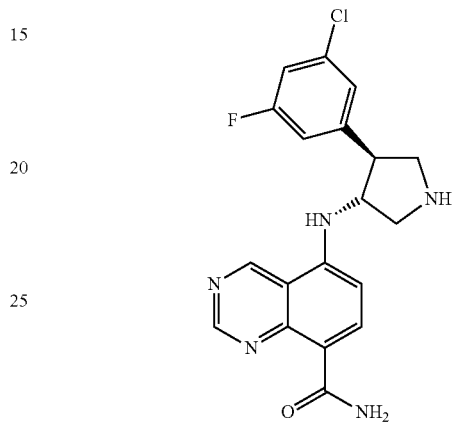

Example 2

5-((4-(3-chloro-5-fluorophenyl)pyrrolidin-3-yl)amino)quinazoline-8-carboxamide (Trans_racemic)

The title compound was synthesized according to the procedure described for the preparation of Example 1 by coupling with tert-butyl 3-amino-4-(3-chloro-5-fluorophenyl)pyrrolidine-1-carboxylate (trans_racemic). LC-MS (M+H=386, obsd.=386/388).

P70S6K IC$_{50}$: 160 nM

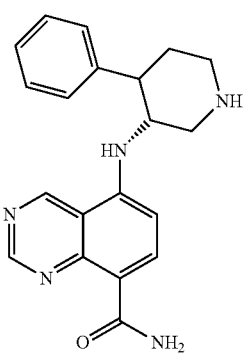

Example 3

5-((4-phenylpiperidin-3-yl)amino)quinazoline-8-carboxamide (trans_racemic)

The title compound was synthesized according to the procedure described for the preparation of Example 1 by coupling with tert-butyl 3-amino-4-phenylpiperidine-1-carboxylate (trans_racemic). LC-MS. (M+H=348, obsd=348).

P70S6K IC$_{50}$: 4.1 nM

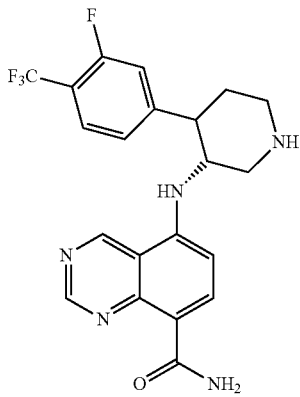

Example 4

5-((4-(3-fluoro-4-(trifluoromethyl)phenyl)piperidin-3-yl)amino)quinazoline-8-carboxamide (trans_racemic)

The title compound was synthesized according to the procedure described for the preparation of Example 1 by coupling with tert-butyl 3-amino-4-(3-fluoro-4-(trifluoromethyl)phenyl)piperidine-1-carboxylate (trans_racemic). LC-MS. (M+H=434, obsd.=434). $^1$HNMR: (DMSO) δ 9.85 (s, 1H), 9.20 (s, 1H), 9.24-9.26 (d, 2H), 8.50-8.52 (d, 1H), 7.73-7.75 (m, 1H), 7.47-7.49 (d, 1H), 7.29-7.30 (d, 1H), 6.88-6.90 (d, 1H), 4.50-4.55 (d, 1H), 3.58-3.60 (m, 1H), 3.46-3.49 (m, 1H), 3.35-3.40 (m, 2H), 3.12-3.14 (m, 1H), 2.80-2.84 (m, 1H), 2.30-2.35 (m, 1H).

P70S6K IC$_{50}$: 5.9 nM

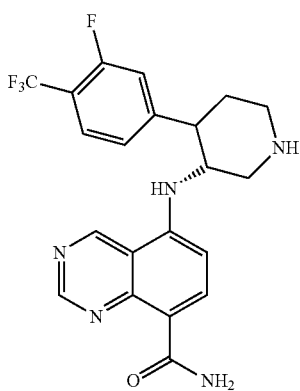

Example 5

5-(((3R)-4-(3-fluoro-4-(trifluoromethyl)phenyl)piperidin-3-yl)amino)quinazoline-8-carboxamide (chiral, one of enantiomer of Example 4 with unknown absolute configuration)

The title compound was isolated via chiral chromatography of Example 4. LC-MS (M+H=434, obsd.=434).

P70S6K IC$_{50}$: 9.9 nM

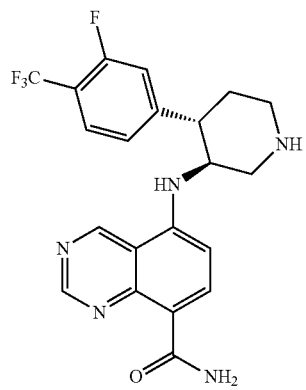 [SMILES: NC(=O)c1ccc(N[C@@H]2CNCC[C@H]2c2ccc(C(F)(F)F)c(F)c2)c2cncnc12]

Example 6

5-(((3S,4S)-4-(3-fluoro-4-(trifluoromethyl)phenyl)piperidin-3-yl)amino)quinazoline-8-carboxamide (chiral, second enantiomer of Example 4 with unknown absolute configuration)

The title compound was isolated via chiral chromatography of Example 4. LC-MS (M+H=434, obsd.=434).

P70S6K IC$_{50}$: 54 nM

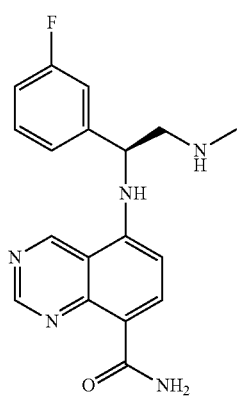 [SMILES: CNC[C@@H](Nc1ccc(C(N)=O)c2ncncc12)c1cccc(F)c1]

Example 7

(S)-5-((1-(3-fluorophenyl)-2-(methylamino)ethyl)amino)quinazoline-8-carboxamide (chiral)

A reaction mixture of A (100.00 mg; 0.43 mmol; 1.00 eq.), N—[(S)-2-Amino-2-(3-fluoro-phenyl)-ethyl]-4-nitro-benzenesulfonamide (152.24 mg; 0.45 mmol; 1.05 eq.) and DIEA (0.15 ml; 0.85 mmol; 2.00 eq.) in NMP (1 ml) was stirred at 120° C. for overnight. The reaction solution was cooled and then poured into water, extracted with EtOAc and washed with brine, dried, and concentrated to give the crude product, which was subjected to SNAP column (25 g, eluted with 20-80% EtOAc in hexane) to afford N—[(S)-2-(8-Cyano-quinazolin-5-ylamino)-2-(3-fluoro-phenyl)-ethyl]-N-methyl-4-nitro-benzenesulfonamide (120 mg).

To a stirred solution of N—[(S)-2-(8-Cyano-quinazolin-5-ylamino)-2-(3-fluoro-phenyl)-ethyl]-N-methyl-4-nitro-benzenesulfonamide (120.00 mg; 0.24 mmol; 1.00 eq.) in DMSO (8 ml) was added aqueous 2.0M NaOH (0.59 ml; 1.18 mmol; 5.00 eq.) and aqueous 35% hydrogen peroxide (0.14 ml; 1.42 mmol; 6.00 eq.) and continued stirring at 40° C. overnight. The crude product was purified by prep-HPLC to yield the desired product, which was then added of acetonitrile (2 ml), thiophenol (0.1 ml), CsCO$_3$ (200 mg), and stirred at 40° C. overnight. The crude was purified by prepHPLC to afford the title product. LC-MS (M+H=434, obsd.=434).

P70S6K IC$_{50}$: >1000 nM

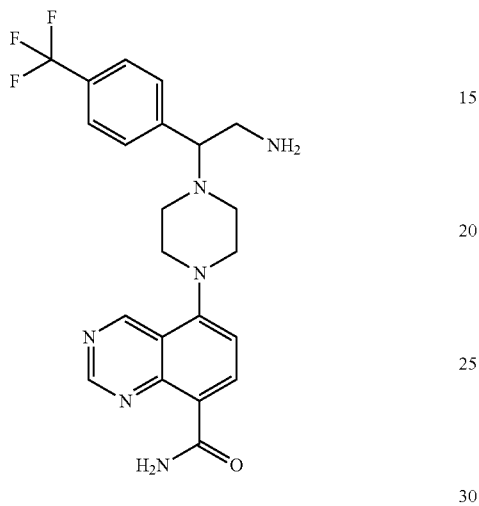

Example 8

5-(4-(2-amino-1-(4-(trifluoromethyl)phenyl)ethyl) piperazin-1-yl)quinazoline-8-carboxamide (racemic)

The title compound was synthesized according to the procedure described for the preparation of Example 7 by coupling with 4-nitro-N-(2-(piperazin-1-yl)-2-(4-(trifluoromethyl)phenyl)ethyl)benzenesulfonamide, followed by hydrolysis and deprotection. LC-MS. (M+H=445, obsd=445).

P70S6K IC$_{50}$: 210 nM

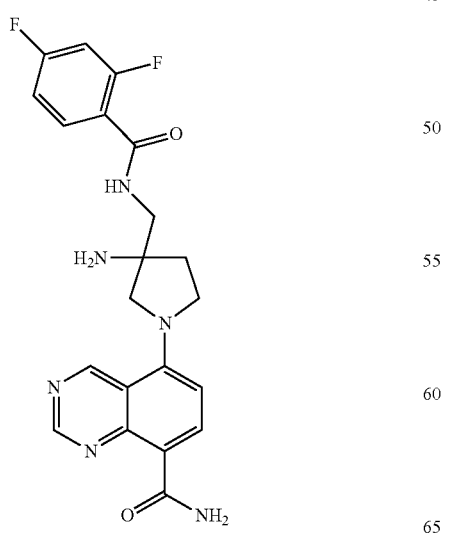

Example 9

5-(3-amino-3-((2,4-difluorobenzamido)methyl)pyrrolidin-1-yl)quinazoline-8-carboxamide (racemic)

The title compound was synthesized according to the procedure described for the preparation of Example 1 by coupling with N-((3-aminopyrrolidin-3-yl)methyl)-2,4-difluorobenzamide, followed by nitrile hydrolysis. LC-MS (M+H=427, obsd=427).

p70S6K IC$_{50}$: >1000 nM

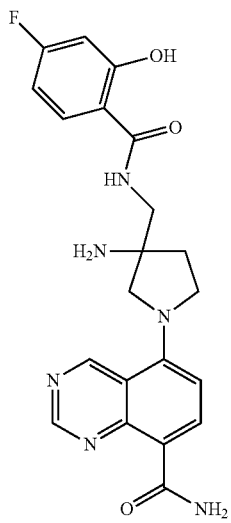 [SMILES: NC(=O)c1ccc(N2CCC(N)(CNC(=O)c3ccc(F)cc3O)C2)c2cncnc12]

Example 10

5-(3-amino-3-((4-fluoro-2-hydroxybenzamido)methyl)pyrrolidin-1-yl)quinazoline-8-carboxamide (racemic)

The title compound was isolated as a side product from the synthesis of Example 9. LC-MS (M+H=425, obsd=425).

p70S6K IC$_{50}$: >1000 nM

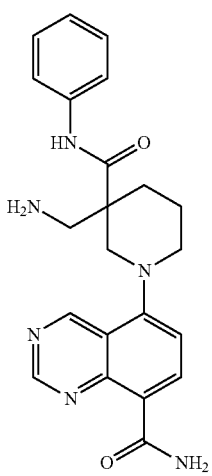 [SMILES: NCC1(C(=O)Nc2ccccc2)CCCN(c2ccc(C(N)=O)c3ncncc23)C1]

Example 11

5-(3-(aminomethyl)-3-(phenylcarbamoyl)piperidin-1-yl)quinazoline-8-carboxamide (racemic)

The title compound was synthesized according to the procedure described for the preparation of Example 1 by coupling with benzyl((3-(phenylcarbamoyl)piperidin-3-yl)methyl)carbamate, followed by hydrolysis and de-protection. LC-MS (M+H=404, obsd=405).

p70S6K IC$_{50}$: >1000 nM

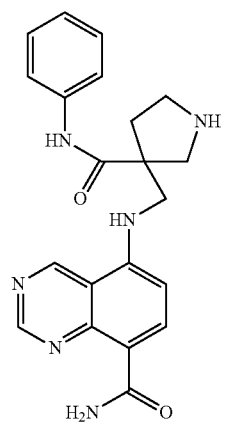 [SMILES: NC(=O)c1ccc(NCC2(C(=O)Nc3ccccc3)CCNC2)c2cncnc12]

Example 12

5-(((3-(phenylcarbamoyl)pyrrolidin-3-yl)methyl)amino)quinazoline-8-carboxamide (racemic)

The title compound was synthesized according to the procedure described for the preparation of Example 1 by coupling with tert-butyl 3-(aminomethyl)-3-(phenyl-carbamoyl)pyrrolidine-1-carboxylate (racemic. LC-MS (M+H=390, obsd.=391).

p70S6K IC$_{50}$: 650 nM

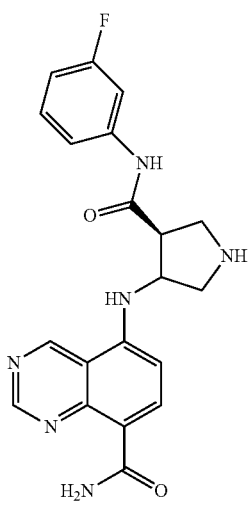 [SMILES: NC(=O)c1ccc(NC2CNC[C@@H]2C(=O)Nc2cccc(F)c2)c2cncnc12]

Example 13

5-((-4-((3-fluorophenyl)carbamoyl)pyrrolidin-3-yl)amino)quinazoline-8-carboxamide (trans_racemic)

The title compound was synthesized according to the procedure described for the preparation of Example 1 by coupling with tert-butyl 3-amino-4-((3-fluorophenyl)carbamoyl)pyrrolidine-1-carboxylate (trans_racemic). LC-MS (M+H=395, obsd.=395).

p70S6K IC$_{50}$: 290 nM

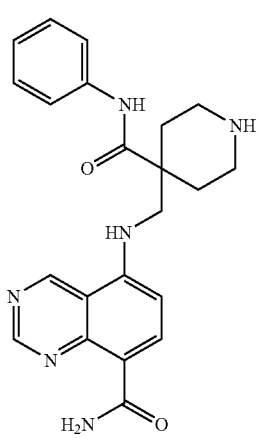 [SMILES: NC(=O)c1ccc(NCC2(C(=O)Nc3ccccc3)CCNCC2)c2cncnc12]

Example 14

5-(((4-(phenylcarbamoyl)piperidin-4-yl)methyl)amino)quinazoline-8-carboxamide (racemic)

The title compound was synthesized according to the procedure described for the preparation of Example 1 by coupling with 2-(trimethylsilyl)ethyl 4-(aminomethyl)-4-(phenylcarbamoyl)piperidine-1-carboxylate (racemic). LC-MS (M+H=404, obsd.=405).

p70S6K IC$_{50}$: >1000 nM

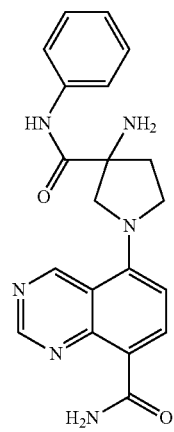 [SMILES: NC(=O)c1ccc(N2CCC(N)(C(=O)Nc3ccccc3)C2)c2cncnc12]

Example 15

5-(3-amino-3-(phenylcarbamoyl)pyrrolidin-1-yl)quinazoline-8-carboxamide (racemic)

The title compound was synthesized according to the procedure described for the preparation of Example 1 by coupling with tert-butyl(3-(phenylcarbamoyl)pyrrolidin-3-yl)carbamate (racemic). LC-MS (M+H=377, obsd.=377).

p70S6K $IC_{50}$: 2300 nM

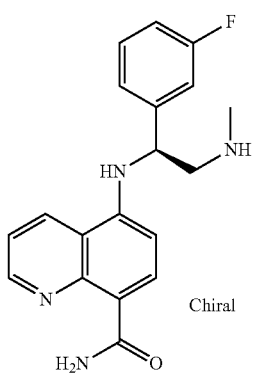 [SMILES: CNC[C@@H](Nc1ccc(C(N)=O)c2ncccc12)c1cccc(F)c1]

Chiral

Example 16

(S)-5-((1-(3-fluorophenyl)-2-(methylamino)ethyl)amino)quinoline-8-carboxamide (chiral)

A reaction mixture of 5-Bromo-quinoline-8-carboxylic acid methyl ester (600.00 mg; 2.25 mmol; 1.00 eq.), N—[(S)-2-Amino-2-(3-fluoro-phenyl)-ethyl]-N-methyl-4-nitro-benzenesulfonamide (876.48 mg; 2.48 mmol; 1.10 eq.), potassium phosphate, tribasic (957.26 mg; 4.51 mmol; 2.00 eq.), dicyclohexyl-(2',4',6'-triisopropyl-biphenyl-2-yl)-phosphane (214.99 mg; 0.45 mmol; 0.20 eq.), palladium (+2) acetate (50.62 mg; 0.23 mmol; 0.10 eq.) and toluene (5 ml) in microwave tube were stirred at 100° C. overnight. The crude was purified by prep HPLC (Basic condition) to afford (S)-5-{1-(3-Fluoro-phenyl)-2-[methyl-(4-nitro-benzenesulfonyl)-amino]-ethylamino}-quinoline-8-carboxylic acid methyl ester (250 mg). LC-MS (M+H=339, obsd.=339).

The above methyl ester (250.00 mg; 0.46 mmol; 1.00 eq.) was added 7.0M ammonia in MeOH (15.00 ml), stirred at 50° C. for 5 days. The reaction mixture was concentrated and purified by prep HPLC to yield (S)-5-{1-(3-Fluoro-phenyl)-2-[methyl-(4-nitro-benzenesulfonyl)-amino]-ethylamino}-quinoline-8-carboxamide, which was dissolved in acetonitrile (5 ml) and added of benzenethiol (204.58 mg; 1.86 mmol; 4.00 eq.) and $Cs_2CO_3$ (605.00 mg; 1.86 mmol; 4.00 eq.). The reaction mixture was stirred at RT overnight. After workup, the residue was purified by prep HPLC to afford Example 16 (30 mg, 19%). LC-MS (M+H=339, obsd=339).

p70S6K $IC_{50}$: >1000 nM

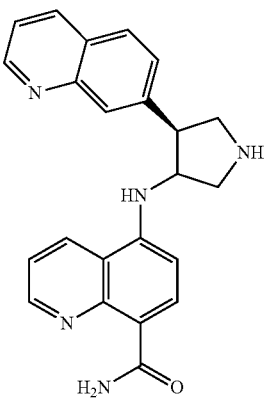 [SMILES: NC(=O)c1ccc(NC2CNC[C@@H]2c2ccc3cccnc3c2)c2cccnc12]

Example 17

5-((-4-(quinolin-7-yl)pyrrolidin-3-yl)amino)quinoline-8-carboxamide (trans_racemic)

The title compound was synthesized according to the procedure described for the preparation of Example 16 by using methyl 5-bromoquinazoline-8-carboxylate coupled with tert-butyl 3-amino-4-(quinolin-7-yl)pyrrolidine-1-carboxylate (trans_racemic), conversion of the methyl ester to the amide with $NH_3$ in MeOH, followed by N-Boc deprotection to afford Example 17. LC-MS (M+H=384, obsd=384).

p70S6K $IC_{50}$: 190 nM

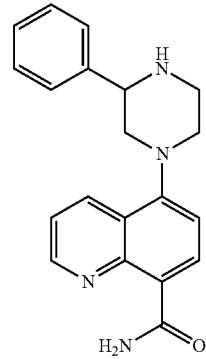 [SMILES: NC(=O)c1ccc(N2CCNC(c3ccccc3)C2)c2cccnc12]

Example 18

5-(3-phenylpiperazin-1-yl)quinoline-8-carboxamide (racemic)

The title compound was synthesized according to the procedure described for the preparation of Example 16 by using methyl 5-bromoquinazoline-8-carboxylate coupled with tert-butyl 2-phenylpiperazine-1-carboxylate, conversion of the methyl ester to the amide with $NH_3$ in MeOH, followed by N-Boc deprotection to afford Example 18. LC-MS. (M+H=333, obsd=333).

p70S6K $IC_{50}$: 670 nM

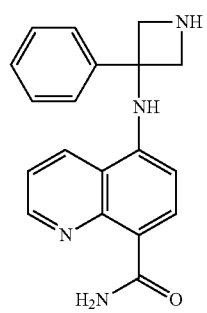 [SMILES: NC(=O)c1ccc(NC2(c3ccccc3)CNC2)c2cccnc12]

Example 19

5-((3-phenylazetidin-3-yl)amino)quinoline-8-carboxamide

The title compound was synthesized according to the procedure described for the preparation of Example 16 by using methyl 5-bromoquinazoline-8-carboxylate coupled with tert-butyl 3-amino-3-phenylazetidine-1-carboxylate (racemic), conversion of the methyl ester to the amide with $NH_3$ in MeOH, followed by N-Boc deprotection to afford Example 19. LC-MS (M+H=319, obsd=319).

p70S6K $IC_{50}$: >1000 nM

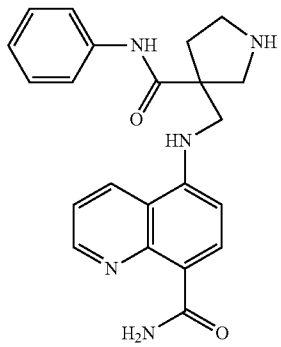 [SMILES: NC(=O)c1ccc(NCC2(C(=O)Nc3ccccc3)CCNC2)c2cccnc12]

Example 20

5-(((3-(phenylcarbamoyl)pyrrolidin-3-yl)methyl)amino)quinoline-8-carboxamide (racemic)

The title compound was synthesized according to the procedure described for the preparation of Example 16 by using methyl 5-bromoquinazoline-8-carboxylate coupled with tert-butyl 3-(aminomethyl)-3-(phenylcarbamoyl)pyrrolidine-1-carboxylate (racemic), conversion of the methyl ester to the amide with $NH_3$ in MeOH, followed by N-Boc deprotection to afford Example 20. LC-MS (M+H=390, obsd.=390).

p70S6K $IC_{50}$: >1000 nM

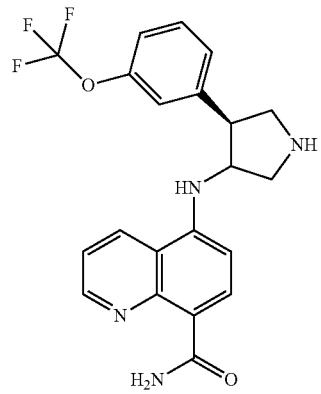 [SMILES: NC(=O)c1ccc(NC2CNC[C@@H]2c2cccc(OC(F)(F)F)c2)c2cccnc12]

Example 21

5-((-4-(3-(trifluoromethoxy)phenyl)pyrrolidin-3-yl)amino)quinoline-8-carboxamide (racemic_trans)

A reaction mixture of 5-Bromo-quinoline-8-carbonitrile (200.00 mg; 0.86 mmol; 1.00 eq), (3-amino-4-(3-trifluoromethoxy-phenyl)-pyrrolidine-1-carboxylic acid tert-butyl ester (0.41 ml; 1.03 mmol; 1.20 eq.) (trans_racemic), sodium; 2-methyl-propan-2-olate (181.43 mg; 1.89 mmol; 2.20 eq.), and dicyclohexyl-(2',4',6'-triisopropyl-biphenyl-2-yl)-phosphane (122.73 mg; 0.26 mmol; 0.30 eq.) in toluene (5 ml) in microwave tube was degas, followed by adding $Pd_2(dba)_3$ (74.02 mg; 0.13 mmol; 0.15 eq.). The resulting mixture was stirred for 10 min at RT, placed in microwave at 100° C. for 20 min. The reaction mixture was concentrated and re-dissolved in DMSO, purified by prep HPLC (Basic condition, 70-75% acetonitrile in water) to give 3-(8-cyano-quinolin-5-ylamino)-4-(3-trifluoromethoxy-phenyl)-pyrrolidine-1-carboxylic acid tert-butyl ester (trans_racemic) (150 mg, 35%).

A reaction mixture of 3-(8-Cyano-quinolin-5-ylamino)-4-(3-trifluoromethoxy-phenyl)-pyrrolidine-1-carboxylic acid tert-butyl ester (trans_racemic) (136.00 mg; 0.27 mmol; 1.00 eq.) in concentrate sulfate acid (2.00 ml; 37.52 mmol; 137.53 eq.) was heated at 100° C. for 1 hr. The reaction solution was cooled and poured to crashed ice. Solid sodium hydroxide was added to adjust PH=9. The separated oil was purified by prep HPLC to afford Example 21 (15 mg). LC-MS (M+H=417, obsd=417).

p70S6K $IC_{50}$: 22 nM

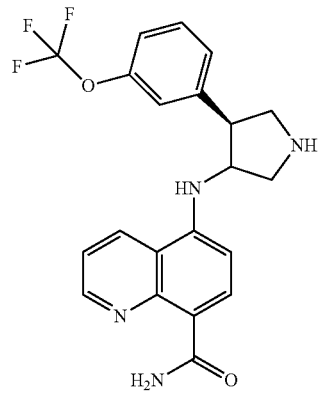 [SMILES: NC(=O)c1ccc(NC2CNC[C@@H]2c2cccc(OC(F)(F)F)c2)c2cccnc12]

Example 22

5-(((4S)-4-(3-(trifluoromethoxy)phenyl)pyrrolidin-3-yl)amino)quinoline-8-carboxamide (chiral, 1st enantiomer of Example 21 with unknown absolute configuration)

The title compound was isolated via chiral chromatography of racemic Example 21. LC-MS (M+H=417, obsd=417).
p70S6K IC$_{50}$: 31 nM

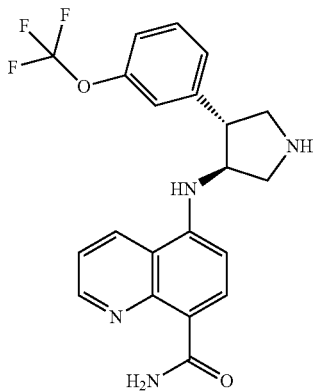 [SMILES: NC(=O)c1ccc(N[C@@H]2CNC[C@H]2c2cccc(OC(F)(F)F)c2)c2cccnc12]

Example 23

5-(((3S,4R)-4-(3-(trifluoromethoxy)phenyl)pyrrolidin-3-yl)amino)quinoline-8-carboxamide (chiral, 2nd enantiomer of Example 21 with unknown absolute configuration)

The title compound was isolated via chiral chromatography of racemic Example 21. LC-MS (M+H=417, obsd=417).
$^1$HNMR: (DMSO) $^\delta$ 9.92 (s, 1H), 9.76 (s, 1H), 8.20-8.23 (d, 1H), 7.98-8.00 (d, 1H), 7.30-7.32 (d, 1H), 7.25 (s, 1H), 7.15 (t, 1H), 6.80-6.82 (d, 1H), 4.60-4.63 (m, 1H), 3.80-3.90 (m, 2H), 3.65 (t, 1H), 3.30 (t, 1H), 3.20-3.25 (m, 1H).
p70S6K IC$_{50}$: 690 nM

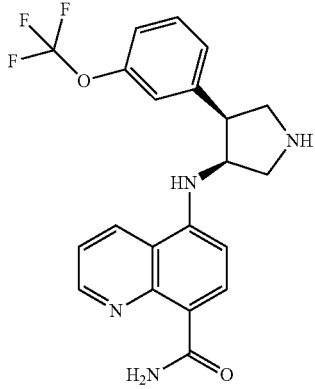 [SMILES: NC(=O)c1ccc(N[C@@H]2CNC[C@@H]2c2cccc(OC(F)(F)F)c2)c2cccnc12]

Example 24

5-((-4-(3-(trifluoromethoxy)phenyl)pyrrolidin-3-yl)amino)quinoline-8-carboxamide (racemic_cis)

The title compound was isolated as a side product from the synthesis of Example 21. LC-MS. (M+H=417, obsd.=417).
p70S6K IC$_{50}$: 23 nM

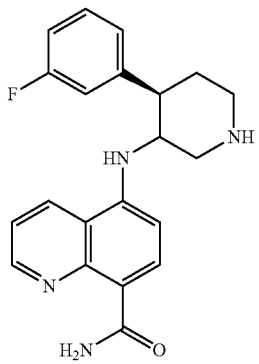 [SMILES: NC(=O)c1ccc(NC2CNCC[C@@H]2c2cccc(F)c2)c2cccnc12]

Example 25

5-((4-(3-fluorophenyl)piperidin-3-yl)amino)quinoline-8-carboxamide (racemic_trans)

The title compound was synthesized according to the procedure described for the preparation of Example 16 by using methyl 5-bromoquinazoline-8-carboxylate coupled with tert-butyl 3-amino-4-(3-fluorophenyl)piperidine-1-carboxylate (trans_racemic), conversion of the methyl ester to the amide with NH$_3$ in MeOH, followed by N-Boc deprotection to afford Example 25. LC-MS (M+H=365, obsd.=365).
p70S6K IC$_{50}$: 520 nM

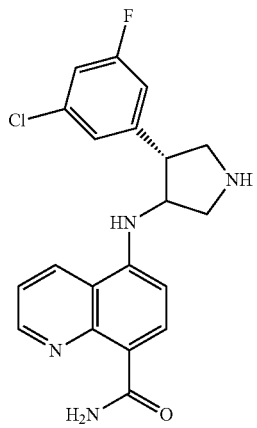 [SMILES: NC(=O)c1ccc(NC2CNC[C@H]2c2cc(F)cc(Cl)c2)c2cccnc12]

Example 26

5-(((4R)-4-(3-chloro-5-fluorophenyl)pyrrolidin-3-yl)amino)quinoline-8-carboxamide (racemic_trans)

The title compound was synthesized according to the procedure described for the preparation of Example 16 by using methyl 5-bromoquinazoline-8-carboxylate coupled with tert-butyl 3-amino-4-(3-chloro-5-fluorophenyl)pyrrolidine-1-carboxylate (trans_racemic), conversion of the methyl ester to the amide with NH$_3$ in MeOH, followed by N-Boc deprotection to afford Example 26. LC-MS. (M+H=385, obsd=384/386).
p70S6K IC$_{50}$: 350 nM

49

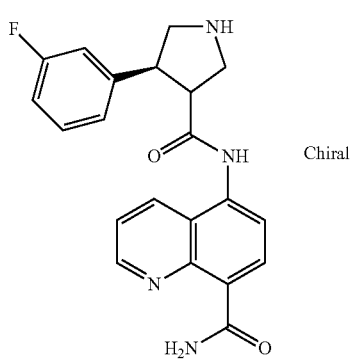 [SMILES: NC(=O)c1ccc(NC(=O)C2CNC[C@@H]2c2cccc(F)c2)c2cccnc12]

Example 27

5-((4S)-4-(3-fluorophenyl)pyrrolidine-3-carboxamido)quinoline-8-carboxamide (chiral, absolutely)

A reaction mixture of 5-amino-quinoline-8-carbonitrile (1000.00 mg; 4.29 mmol; 1.00 eq.) in sulfuric acid (5.00 ml; 93.80 mmol; 21.86 eq.) was stirred at 100° C. for 1 h. The reaction mixture was then cooled, poured into ice and neutralized with 2N sodium hydroxide to PH=9. The precipitate was filtered, washed with water and dried to afford 5-amino-quinoline-8-carboxamide (800 mg, yield 74.3%).

To a solution of tert-butyl(3R,4S)-4-(3-fluoro-phenyl)-pyrrolidine-1,3-dicarboxylate (125.00 mg; 0.40 mmol; 1.00 eq.) in DCE (4.0 ml) bis(2-oxo-1,3-oxazolidin-3-yl)phosphinic chloride (102.87 mg; 0.40 mmol; 1.00 eq.) was added. After stirring for 15 mins at RT, DIEA (0.15 ml; 0.81 mmol; 2.00 eq.) and 5-aminoquinoline-8-carboxamide (75.65 mg; 0.40 mmol; 1.00 eq) were added. The reaction mixture was stirred overnight at 60° C. The crude was purified by prep HPLC to yield (4S)-tert-butyl 3-((8-carbamoylquinolin-5-yl)carbamoyl)-4-(3-fluorophenyl)pyrrolidine-1-carboxylate, which was added 1 ml 4.0M HCl and 1 ml methanol, stirred at RT for 3 h. The reaction mixture was concentrated, neutralized to Ph 7 and purified by prep HPLC to afford Example 27. (M+H=479, obsd=479).

p70S6K $IC_{50}$: >1000 nM

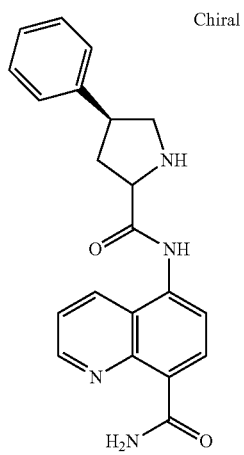 [SMILES: NC(=O)c1ccc(NC(=O)C2C[C@@H](c3ccccc3)CN2)c2cccnc12]

50

Example 28

5-((4S)-4-phenylpyrrolidine-2-carboxamido)quinoline-8-carboxamide (chiral, absolutely)

The title compound was synthesized according to the procedure described for the preparation of Example 27 by using 5-aminoquinoline-8-carboxamide coupled with (4S)-1-(tert-butoxycarbonyl)-4-phenylpyrrolidine-2-carboxylic acid, followed by removal of the protecting group to afford Example 28. LC-MS. (M+H=361, obsd=361).

p70S6K $IC_{50}$: 578 nM

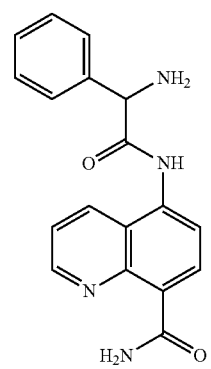 [SMILES: NC(=O)c1ccc(NC(=O)C(N)c2ccccc2)c2cccnc12]

Example 29

5-(2-amino-2-phenylacetamido)quinoline-8-carboxamide (racemic)

The title compound was synthesized according to the procedure described for the preparation of Example 27 by using 5-aminoquinoline-8-carboxamide coupled with 2-((tert-butoxycarbonyl)amino)-2-phenylacetic acid, followed by removal of the protecting group to afford Example 29. LC-MS (M+H=321, obsd=321).

p70S6K $IC_{50}$: >1000 nM

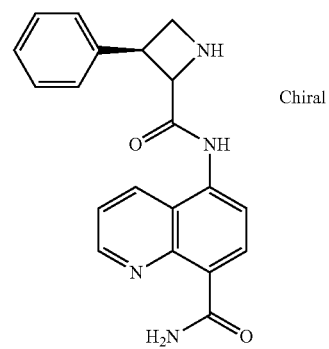 [SMILES: NC(=O)c1ccc(NC(=O)C2NC[C@@H]2c2ccccc2)c2cccnc12]

Example 30

5-((3S)-3-phenylazetidine-2-carboxamido)quinoline-8-carboxamide (chiral, absolutely)

The title compound was synthesized according to the procedure described for the preparation of Example 27 by using 5-aminoquinoline-8-carboxamide coupled with (3S)-1-(tert-butoxycarbonyl)-3-phenylazetidine-2-carboxylic acid, followed by de-Boc to afford Example 30. LC-MS (M+H=347, obsd=347).

p70S6K IC$_{50}$: >1000 nM

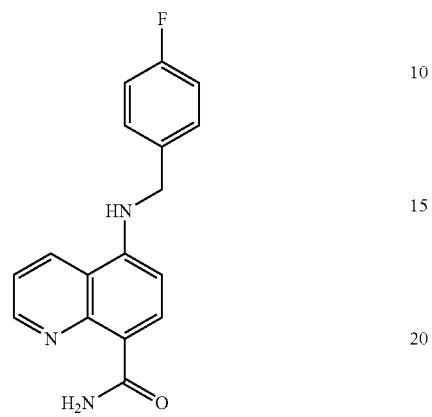

Example 31

5-(4-Fluorobenzylamino)-quinoline-8-carboxamide

To a solution of 5-aminoquinoline-8-carboxamide (120 mg, 0.64 mmol) in anhydrous DMF (2 mL) were added 4-fluorobenzyl bromide (242.34 mg, 1.28 mmol) and potassium carbonate (531.56 mg, 3.85 mmol). The suspension was heated at 50° C. overnight. The mixture was diluted with MeOH (4 mL) and the solid was filtered. The crude product was purified through reverse phase HPLC to afford Example 31 (90 mg). LC-MS (M+H=296, obsd=296).

p70S6K IC$_{50}$: 875 nM

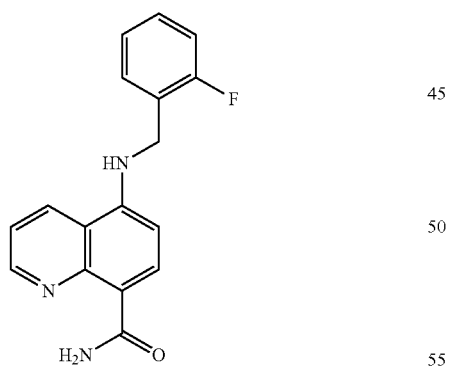

Example 32

5-(2-Fluorobenzylamino)-quinoline-8-carboxamide

The title compound was synthesized according to the procedure described for the preparation of Example 31. LC-MS (M+H=296, obsd=296).

p70S6K IC$_{50}$: >1000 nM

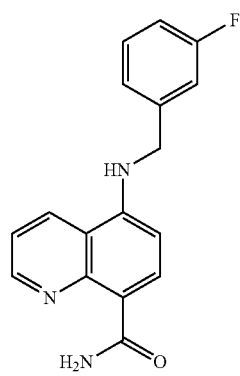 [SMILES: NC(=O)c1ccc(NCc2cccc(F)c2)c2cccnc12]

Example 33

5-(3-Fluorobenzylamino)-quinoline-8-carboxamide

The title compound was synthesized according to the procedure described for the preparation of Example 31. LC-MS (M+H=296, obsd=296).

p70S6K IC$_{50}$: 369 nM

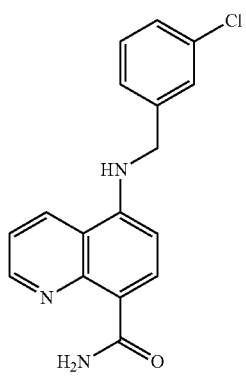 [SMILES: NC(=O)c1ccc(NCc2cccc(Cl)c2)c2cccnc12]

Example 34

5-(3-Chlorobenzylamino)-quinoline-8-carboxamide

The title compound was synthesized according to the procedure described for the preparation of Example 31. LC-MS (M+H=312, obsd=312).

p70S6K IC$_{50}$: 140 nM

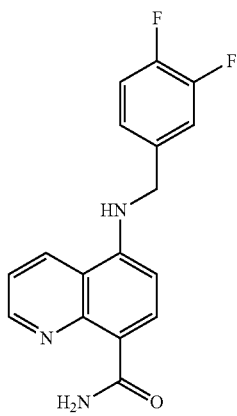 [SMILES: NC(=O)c1ccc(NCc2ccc(F)c(F)c2)c2cccnc12]

Example 35

5-(3,4-Difluorobenzylamino)-quinoline-8-carboxamide

The title compound was synthesized according to the procedure described for the preparation of Example 31. LC-MS (M+H=314, obsd=314).

p70S6K $IC_{50}$: >1000 nM

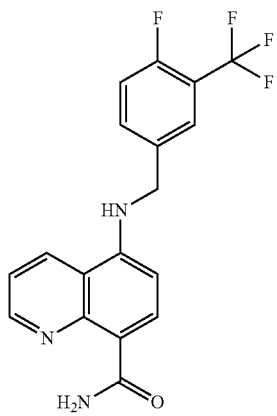

Example 37

5-(4-Fluoro-3-trifluoromethylbenzylamino)-quinoline-8-carboxamide

The title compound was synthesized according to the procedure described for the preparation of Example 31. LC-MS (M+H=364, obsd.=364).

p70S6K $IC_{50}$: 695 nM

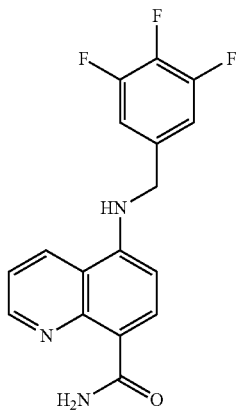 [SMILES: NC(=O)c1ccc(NCc2cc(F)c(F)c(F)c2)c2cccnc12]

Example 36

5-(3,4,5-trifluorobenzylamino)-quinoline-8-carboxamide

The title compound was synthesized according to the procedure described for the preparation of Example 31. LC-MS (M+H=332, obsd.=332).

p70S6K $IC_{50}$: >1000 nM

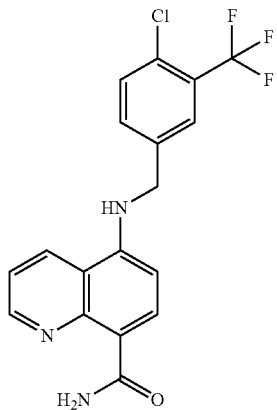 [SMILES: NC(=O)c1ccc(NCc2ccc(Cl)c(C(F)(F)F)c2)c2cccnc12]

Example 38

5-(4-Chloro-3-trifluoromethylbenzylamino)-quinoline-8-carboxamide

The title compound was synthesized according to the procedure described for the preparation of Example 31. LC-MS (M+H=380, obsd.=380).

p70S6K $IC_{50}$: >1000 nM

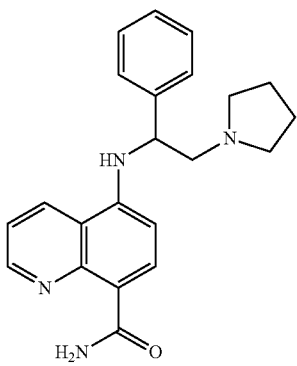 [SMILES: NC(=O)c1ccc(NC(CN2CCCC2)c2ccccc2)c2cccnc12]

Example 39

5-((1-phenyl-2(pyrrolidin-1-yl)ethyl)amino-quinoline-8-carboxamide

The title compound was synthesized according to the procedure described for the preparation of Example 31. LC-MS (M+H=361, obsd.=361).

p70S6K $IC_{50}$: >1000 nM

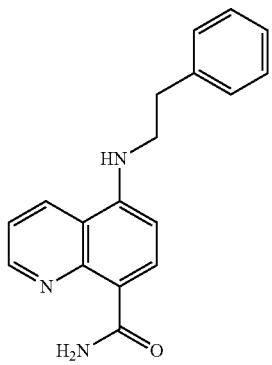 [SMILES: NC(=O)c1ccc(NCCc2ccccc2)c2cccnc12]

Example 40

5-(Phenylethylamino)-quinoline-8-carboxamide

The title compound was synthesized according to the procedure described for the preparation of Example 31. LC-MS (M+H=292, obsd.=292).

p70S6K $IC_{50}$: >1000 nM

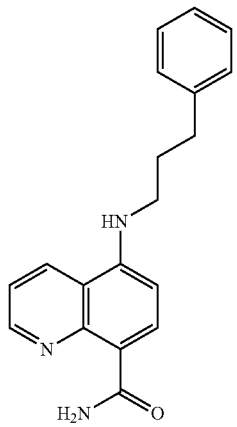 [SMILES: NC(=O)c1ccc(NCCCc2ccccc2)c2cccnc12]

Example 41

5-(Phenylpropylamino)-quinoline-8-carboxamide

The title compound was synthesized according to the procedure described for the preparation of Example 31. LC-MS (M+H=306, obsd.=306).

p70S6K $IC_{50}$: >1000 nM

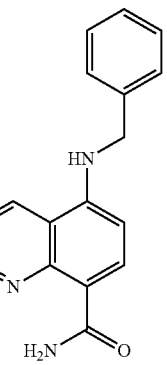

Example 42

5-(Benzylamino)quinoline-8-carboxamide

The title compound was synthesized according to the procedure described for the preparation of Example 31. LC-MS (M+H=278, obsd.=278).

p70S6K $IC_{50}$: 680 nM

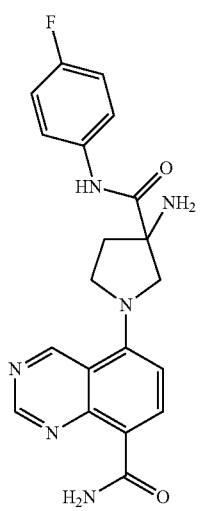 [SMILES: NC(=O)c1ccc(N2CCC(N)(C(=O)Nc3ccc(F)cc3)C2)c2cncnc12]

Example 43

5-[3-amino-3-[(4-fluorophenyl)carbamoyl]pyrrolidin-1-yl]quinazoline-8-carboxamide (racemic)

The title compound was synthesized according to the procedure described for the preparation of Example 1 by coupling with 3-amino-N-(4-fluorophenyl)pyrrolidine-3-carboxamide (racemic), followed by hydrolysis of the nitrile intermediate. LC-MS (M+H=395, obsd.=395). $^1$H NMR (400 MHz, DMSO) δ 13.03 (s, 0H), 9.76 (d, J=13.4 Hz, 2H), 9.24-9.17 (m, 1H), 8.54 (t, J=9.2 Hz, 1H), 7.75 (dd, J=9.0, 5.0 Hz, 2H), 7.55 (d, J=4.1 Hz, 1H), 7.17 (dd, J=16.2, 7.4 Hz, 2H), 6.88 (t, J=8.2 Hz, 1H), 4.36-4.26 (m, 1H), 4.11 (dd, J=16.7, 9.7 Hz, 1H), 3.68 (d, J=10.4 Hz, 1H), 2.08 (t, J=8.5 Hz, 1H), 1.45-1.18 (m, 1H).

p70S6K IC$_{50}$: 1200 nM

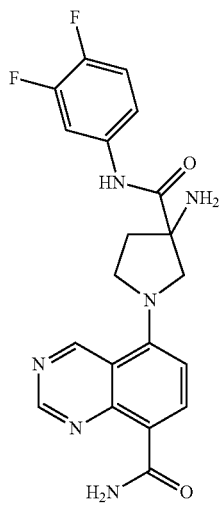 [SMILES: NC(=O)c1ccc(N2CCC(N)(C(=O)Nc3ccc(F)c(F)c3)C2)c2cncnc12]

Example 44

5-(3-amino-3-((3,4-difluorophenyl)carbamoyl)pyrrolidin-1-yl)quinazoline-8-carboxamide (racemic)

The title compound was synthesized according to the procedure described for the preparation of Example 1 by coupling with 3-amino-N-(3,4-difluorophenyl)pyrrolidine-3-carboxamide (racemic), followed by hydrolysis of the nitrile intermediate. LC-MS (M+H=413, obsd.=413). $^1$H NMR (400 MHz, DMSO) δ 9.79-9.71 (m, 2H), 9.21 (s, 1H), 8.56 (d, J=8.9 Hz, 1H), 7.93 (ddd, J=13.3, 7.5, 2.5 Hz, 1H), 7.59-7.49 (m, 2H), 7.41 (dd, J=19.7, 9.1 Hz, 1H), 6.89 (d, J=9.0 Hz, 1H), 4.31 (d, J=10.3 Hz, 1H), 4.10 (dd, J=16.5, 9.7 Hz, 1H), 3.78 (t, J=8.0 Hz, 1H), 3.68 (d, J=10.3 Hz, 1H), 2.08 (t, J=8.5 Hz, 1H).

p70S6K IC$_{50}$: 1300 nM

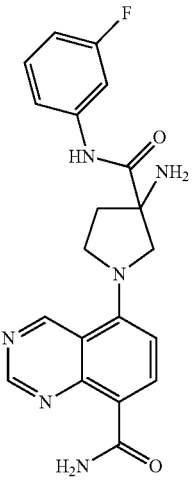 [SMILES: NC(=O)c1ccc(N2CCC(N)(C(=O)Nc3cccc(F)c3)C2)c2cncnc12]

Example 45

5-(3-amino-3-((3-fluorophenyl)carbamoyl)pyrrolidin-1-yl)quinazoline-8-carboxamide (racemic)

The title compound was synthesized according to the procedure described for the preparation of Example 1 by coupling with 3-amino-N-(3-fluorophenyl)pyrrolidine-3-carboxamide (racemic), followed by hydrolysis of the nitrile intermediate. LC-MS (M+H=395, obsd.=395). $^1$H NMR (400 MHz, DMSO) δ 13.48 (s, 1H), 9.76 (d, J=13.6 Hz, 2H), 9.21 (d, J=6.6 Hz, 1H), 8.55 (t, J=9.0 Hz, 1H), 7.74 (d, J=11.4 Hz, 1H), 7.54 (dd, J=28.9, 10.7 Hz, 2H), 7.42-7.26 (m, 1H), 7.19 (d, J=8.8 Hz, 1H), 6.96-6.76 (m, 2H), 5.22 (s, 1H), 4.31 (dd, J=19.8, 11.2 Hz, 2H), 4.11 (s, 1H), 3.93-3.73 (m, 2H), 3.69 (d, J=10.3 Hz, 1H).

p70S6K IC$_{50}$: 2000 nM

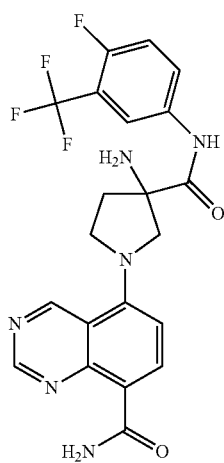 [SMILES: NC(=O)c1ccc(N2CCC(N)(C(=O)Nc3ccc(F)c(C(F)(F)F)c3)C2)c2cncnc12]

Example 46

5-(3-amino-3-((4-fluoro-3-(trifluoromethyl)phenyl)carbamoyl)pyrrolidin-1-yl)quinazoline-8-carboxamide (racemic)

The title compound was synthesized according to the procedure described for the preparation of Example 1 by coupling with 3-amino-N-(4-fluoro-3-(trifluoromethyl)-phenyl)pyrrolidine-3-carboxamide (racemic), followed by hydrolysis of the nitrile intermediate. LC-MS (M+H=395, obsd.=395). $^1$H NMR (400 MHz, DMSO) δ 9.81-9.68 (m, 2H), 9.21 (d, J=7.7 Hz, 1H), 8.56 (d, J=8.9 Hz, 1H), 8.27 (dd, J=6.4, 2.6 Hz, 1H), 8.10-8.00 (m, 1H), 7.60-7.46 (m, 2H), 6.88 (t, J=8.2 Hz, 1H), 4.32 (d, J=10.4 Hz, 1H), 4.10 (dd, J=16.7, 9.7 Hz, 1H), 3.79 (t, J=8.0 Hz, 1H), 3.69 (d, J=10.1 Hz, 1H), 2.11 (d, J=5.1 Hz, 1H).

p70S6K IC$_{50}$: 270 nM

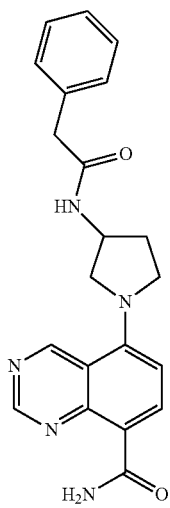 [SMILES: NC(=O)c1ccc(N2CCC(NC(=O)Cc3ccccc3)C2)c2cncnc12]

Example 47

5-(3-(2-phenylacetamido)pyrrolidin-1-yl)quinazoline-8-carboxamide (racemic)

The title compound was synthesized according to the procedure described for the preparation of Example 1 by coupling with 2-phenyl-N-(pyrrolidin-3-yl)acetamide (racemic), followed by hydrolysis of the nitrile intermediate. LC-MS (M+H=376, obsd=376). $^1$H NMR (500 MHz, dmso) δ 9.75 (d, J=9.8 Hz, 2H), 9.21 (d, J=1.3 Hz, 1H), 8.59-8.52 (m, 1H), 8.43 (d, J=6.3 Hz, 1H), 7.57 (s, 1H), 7.23 (td, J=15.7, 8.0 Hz, 5H), 6.88 (d, J=8.9 Hz, 1H), 4.37 (s, 1H), 4.03 (dd, J=10.2, 6.0 Hz, 1H), 3.85 (t, J=8.5 Hz, 1H), 3.76 (s, 1H), 3.59-3.51 (m, 1H), 3.40 (s, 2H), 2.21 (dd, J=12.6, 6.0 Hz, 1H), 2.00 (d, J=5.3 Hz, 1H).

p70S6K IC$_{50}$: 7900 nM

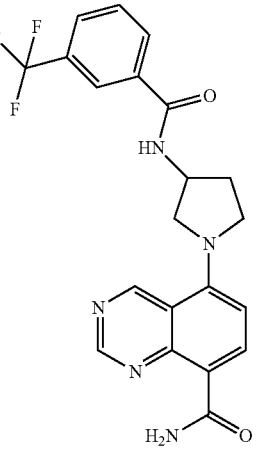

Example 48

5-(3-(3-(trifluoromethyl)benzamido)pyrrolidin-1-yl)quinazoline-8-carboxamide (racemic)

The title compound was synthesized according to the procedure described for the preparation of Example 1 by coupling with N-(pyrrolidin-3-yl)-3-(trifluoromethyl)benzamide (racemic), followed by hydrolysis of the nitrile intermediate. LC-MS (M+H=430, obsd=430). $^1$H NMR (500 MHz, dmso) δ 9.81 (s, 1H), 9.74 (s, 1H), 9.22 (s, 1H), 8.90 (d, J=6.0 Hz, 1H), 8.56 (d, J=8.9 Hz, 1H), 8.22-8.13 (m, 2H), 7.92 (d, J=8.0 Hz, 1H), 7.73 (t, J=8.0 Hz, 1H), 7.57 (s, 1H), 6.91 (d, J=8.9 Hz, 1H), 4.66 (d, J=5.4 Hz, 1H), 4.17-4.08 (m, 1H), 3.93 (s, 1H), 3.87-3.74 (m, 2H), 2.99 (s, 0H), 2.54 (s, 2H), 2.33 (d, J=6.1 Hz, 1H), 2.20 (s, 1H).

p70S6K IC$_{50}$: 2200 nM

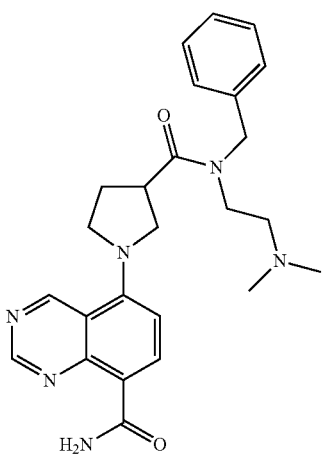 [SMILES: CN(C)CCN(Cc1ccccc1)C(=O)C1CCN(c2ccc(C(N)=O)c3ncncc23)C1]

Example 49

5-(3-(benzyl(2-(dimethylamino)ethyl)carbamoyl)
pyrrolidin-1-yl)quinazoline-8-carboxamide (racemic)

The title compound was synthesized according to the procedure described for the preparation of Example 1 by coupling with N-benzyl-N-(2-(dimethylamino)ethyl)pyrrolidine-3-carboxamide (racemic), followed by hydrolysis of the nitrile intermediate. LC-MS (M+H=447, obsd=447). $^1$H NMR (400 MHz, DMSO) δ 9.74 (s, 2H), 9.21 (d, J=4.5 Hz, 1H), 8.54 (t, J=9.1 Hz, 1H), 7.55 (s, 1H), 7.41-7.20 (m, 5H), 6.88 (dd, J=23.8, 8.7 Hz, 1H), 4.74 (s, 1H), 4.65 (d, J=15.0 Hz, 1H), 4.55 (d, J=14.6 Hz, 1H), 3.91 (ddd, J=23.2, 16.7, 8.5 Hz, 3H), 3.73 (s, 1H), 3.57 (d, J=44.4 Hz, 2H), 3.38 (dd, J=14.9, 7.8 Hz, 2H), 3.00 (s, 1H), 2.54 (d, J=5.9 Hz, 1H), 2.43-2.28 (m, 3H), 2.12 (d, J=14.3 Hz, 5H).

p70S6K IC$_{50}$: 1600 nM

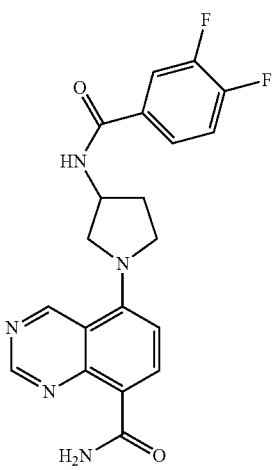 [SMILES: NC(=O)c1ccc(N2CCC(NC(=O)c3ccc(F)c(F)c3)C2)c2cncnc12]

Example 50

5-(3-(3,4-difluorobenzamido)pyrrolidin-1-yl)
quinazoline-8-carboxamide (racemic)

The title compound was synthesized according to the procedure described for the preparation of Example 1 by coupling with 3,4-difluoro-N-(pyrrolidin-3-yl)benzamide (racemic), followed by hydrolysis of the nitrile intermediate. LC-MS (M+H=398, obsd=398). $^1$H NMR (500 MHz, dmso) δ 9.81 (s, 1H), 9.74 (s, 1H), 9.22 (s, 1H), 8.71 (d, J=6.2 Hz, 1H), 8.56 (d, J=8.7 Hz, 1H), 7.97-7.88 (m, 1H), 7.76 (s, 1H), 7.56 (dt, J=16.9, 8.6 Hz, 2H), 6.90 (d, J=8.9 Hz, 1H), 4.64-4.58 (m, 1H), 4.10 (dd, J=10.4, 6.1 Hz, 1H), 3.97-3.88 (m, 1H), 3.82 (s, 1H), 3.74 (dd, J=10.7, 4.3 Hz, 1H), 2.30 (dd, J=12.9, 5.9 Hz, 1H), 2.17 (d, J=5.2 Hz, 1H).

p70S6K IC$_{50}$: 380 nM

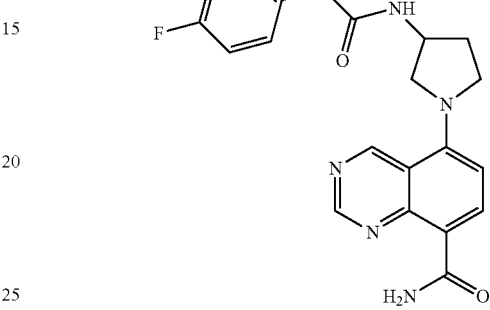

Example 51

5-(3-(2-(4-fluorophenyl)acetamido)pyrrolidin-1-yl)
quinazoline-8-carboxamide (racemic)

The title compound was synthesized according to the procedure described for the preparation of Example 1 by coupling with 2-(4-fluorophenyl)-N-(pyrrolidin-3-yl)-acetamide (racemic), followed by hydrolysis of the nitrile intermediate. LC-MS (M+H=394, obsd=394). $^1$H NMR (400 MHz, DMSO) δ 9.76 (s, 2H), 9.21 (s, 1H), 8.55 (d, J=8.5 Hz, 1H), 8.44 (d, J=6.0 Hz, 1H), 7.59 (s, 1H), 7.25 (s, 2H), 7.08 (t, J=8.0 Hz, 2H), 6.88 (d, J=9.0 Hz, 1H), 4.36 (s, 1H), 4.04 (d, J=6.6 Hz, 1H), 3.85 (s, 1H), 3.77 (s, 1H), 3.54 (d, J=10.1 Hz, 1H), 3.38 (d, J=14.2 Hz, 2H), 2.20 (s, 1H), 1.99 (s, 1H).

p70S6K IC$_{50}$: 5400 nM

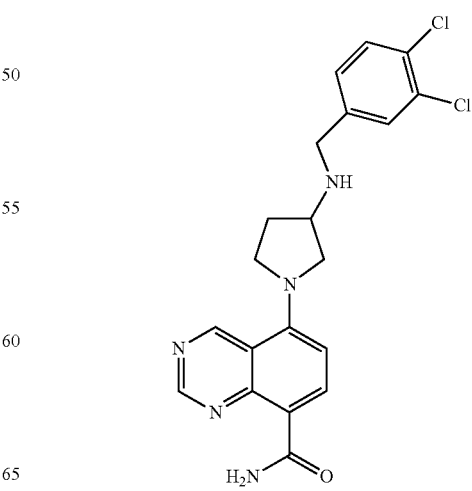

Example 52

5-(3-((3,4-dichlorobenzyl)amino)pyrrolidin-1-yl)quinazoline-8-carboxamide (racemic)

The title compound was synthesized according to the procedure described for the preparation of Example 1 by coupling with N-(3,4-dichlorobenzyl)pyrrolidin-3-amine (racemic), followed by hydrolysis of the nitrile intermediate. LC-MS (M+H=417, obsd=417). $^1$H NMR (500 MHz, dmso) δ 9.73 (s, 2H), 9.18 (s, 1H), 8.52 (d, J=8.9 Hz, 1H), 7.59 (d, J=1.8 Hz, 1H), 7.55-7.47 (m, 2H), 7.34-7.28 (m, 1H), 6.82 (d, J=9.0 Hz, 1H), 3.91 (dd, J=10.4, 5.5 Hz, 1H), 3.88-3.81 (m, 1H), 3.74 (s, 2H), 3.68 (s, 1H), 3.54 (dd, J=10.3, 3.9 Hz, 1H), 3.38 (s, 1H), 2.63 (s, 1H), 2.13-2.04 (m, 1H), 1.94 (d, J=5.3 Hz, 1H).

p70S6K IC$_{50}$: 490 nM

Example 53

5-(3-((3,4-dichlorobenzyl)(methyl)amino)pyrrolidin-1-yl)quinazoline-8-carboxamide (racemic)

The title compound was synthesized according to the procedure described for the preparation of Example 1 by coupling with N-(3,4-dichlorobenzyl)-N-methylpyrrolidin-3-amine (racemic), followed by hydrolysis of the nitrile intermediate. LC-MS (M+H=431, obsd=431). $^1$H NMR (400 MHz, DMSO) δ 9.78 (d, J=17.6 Hz, 2H), 9.21 (s, 1H), 8.54 (d, J=8.7 Hz, 1H), 7.63-7.50 (m, 3H), 7.34 (d, J=8.1 Hz, 1H), 6.90 (d, J=8.9 Hz, 1H), 3.94-3.73 (m, 4H), 3.61 (s, 2H), 3.20 (s, 2H), 2.27 (s, 2H), 2.18 (s, 3H), 2.06-1.93 (m, 2H), 0.08 (s, 1H).

p70S6K IC$_{50}$: 570 nM

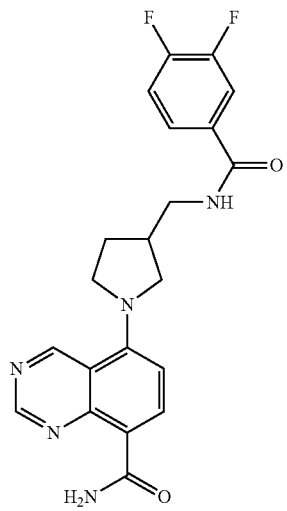 [SMILES: NC(=O)c1ccc(N2CCC(CNC(=O)c3ccc(F)c(F)c3)C2)c2cncnc12]

Example 54

5-(3-((3,4-difluorobenzamido)methyl)pyrrolidin-1-yl)quinazoline-8-carboxamide (racemic)

The title compound was synthesized according to the procedure described for the preparation of Example 1 by coupling 5-bromo-quinazoline-8-carbonitrile with 3,4-difluoro-N-(pyrrolidin-3-ylmethyl)-benzamide (racemic), followed by hydrolysis of the nitrile intermediate. LC-MS (M+H=412, obsd=412). $^1$H NMR (400 MHz, DMSO) δ 9.81 (s, 1H), 9.75 (d, J=4.0 Hz, 1H), 9.20 (s, 1H), 8.72 (t, J=5.6 Hz, 1H), 8.53 (d, J=8.9 Hz, 1H), 7.89 (ddd, J=11.5, 7.8, 2.0 Hz, 1H), 7.74 (dd, J=5.1, 3.3 Hz, 1H), 7.62-7.50 (m, 2H), 6.85 (d, J=9.0 Hz, 1H), 3.92-3.74 (m, 3H), 3.65 (dd, J=10.2, 7.0 Hz, 1H), 3.41 (dtd, J=19.7, 13.3, 6.1 Hz, 2H), 2.63 (dt, J=13.7, 6.8 Hz, 1H), 2.16 (td, J=12.0, 5.9 Hz, 1H), 1.85 (dq, J=15.2, 7.5 Hz, 1H).

p70S6K IC$_{50}$: 233 nM

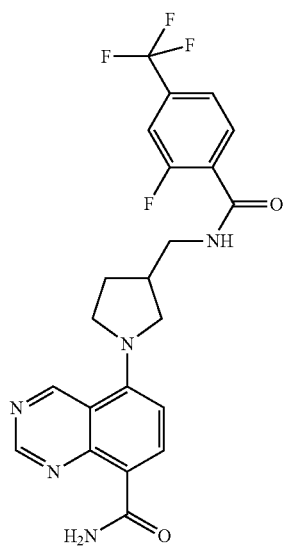 [SMILES: NC(=O)c1ccc(N2CCC(CNC(=O)c3ccc(C(F)(F)F)cc3F)C2)c2cncnc12]

Example 55

5-(3-((2-fluoro-4-(trifluoromethyl)benzamido)methyl)pyrrolidin-1-yl)quinazoline-8-carboxamide (racemic)

The title compound was synthesized according to the procedure described for the preparation of Example 1 by coupling with 2-fluoro-N-(pyrrolidin-3-ylmethyl)-4-(trifluoromethyl)benzamide (racemic), followed by hydrolysis of the nitrile intermediate. LC-MS (M+H=462, obsd=462). $^1$H NMR (400 MHz, DMSO) δ 10.87 (s, 1H), 9.80 (s, 1H), 9.75 (d, J=3.9 Hz, 1H), 9.19 (s, 1H), 8.53 (d, J=8.9 Hz, 1H), 7.89 (d, J=8.1 Hz, 1H), 7.52 (d, J=3.8 Hz, 1H), 6.90-6.80 (m, 2H), 6.72 (d, J=8.0 Hz, 1H), 3.87-3.77 (m, 3H), 3.61 (dd, J=10.1, 7.3 Hz, 1H), 3.45 (s, 2H), 2.71-2.57 (m, 1H), 2.14 (dt, J=19.7, 7.0 Hz, 1H), 1.93-1.79 (m, 1H).

p70S6K $IC_{50}$: 290 nM

Example 56

5-(3-(aminomethyl)piperidin-1-yl)quinazoline-8-carboxamide (racemic)

The title compound was synthesized according to the procedure described for the preparation of Example 1 by coupling 5-bromo-quinazoline-8-carbonitrile with 3-N-boc-aminomethyl piperidine (racemic), followed by hydrolysis of the nitrile intermediate. LC-MS (M+H=287, obsd.=286.2/287.2).

P70S6K $IC_{50}$: 56000 nM AKT $IC_{50}$: >100000 nM

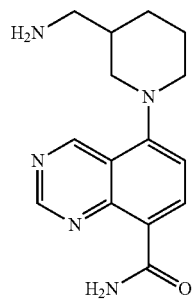 [SMILES: NCC1CCCN(c2ccc(C(N)=O)c3ncncc23)C1]

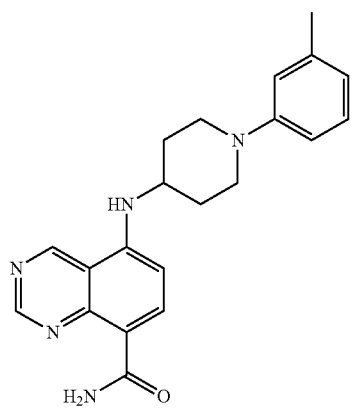 [SMILES: Cc1cccc(N2CCC(Nc3ccc(C(N)=O)c4ncncc34)CC2)c1]

Example 57

5-((1-(m-tolyl)piperidin-4-yl)amino)quinazoline-8-carboxamide

The title compound was synthesized according to the procedure described for the preparation of Example 1 by coupling 5-Bromo-quinazoline-8-carbonitrile with 1-(m-tolyl)piperidin-4-amine, followed by hydrolysis of the nitrile intermediate. LC-MS (M+H=363, obsd.=362.2/363.3).

P70S6K $IC_{50}$: 22000 nM AKT $IC_{50}$: >100000 nM

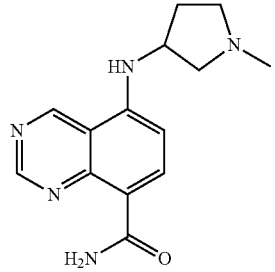 [SMILES: CN1CCC(Nc2ccc(C(N)=O)c3ncncc23)C1]

Example 58

5-((1-methylpyrrolidin-3-yl)amino)quinazoline-8-carboxamide (racemic)

The title compound was synthesized according to the procedure described for the preparation of Example 1 by coupling 5-Bromo-quinazoline-8-carbonitrile with 1-methylpyrrolidin-3-amine (racemic), followed by hydrolysis of the nitrile intermediate. LC-MS (M+H=273, obsd.=272.1/273.1).

P70S6K $IC_{50}$: 20000 nM AKT $IC_{50}$: >100000 nM

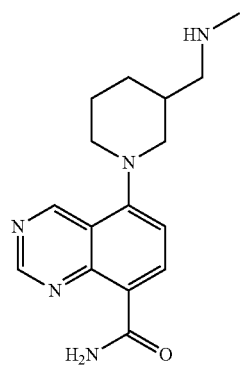 [SMILES: CNCC1CCCN(c2ccc(C(N)=O)c3ncncc23)C1]

Example 59

5-(3-((methylamino)methyl)piperidin-1-yl)quinazoline-8-carboxamide (racemic)

The title compound was synthesized according to the procedure described for the preparation of Example 1 by coupling 5-Bromo-quinazoline-8-carbonitrile with tert-butyl methyl(piperidin-3-ylmethyl)carbamate (racemic), followed by hydrolysis of the nitrile intermediate. LC-MS (M+H=300, obsd.=300.1/301.1).

P70S6K $IC_{50}$: 5900 nM AKT $IC_{50}$: 18000 nM

67

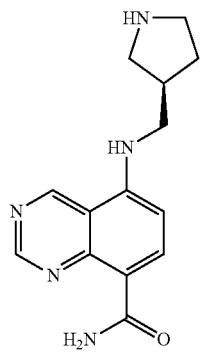 [SMILES: NC(=O)c1ccc(NC[C@@H]2CCNC2)c2cncnc12]

Example 60

(R)-5-((pyrrolidin-3-ylmethyl)amino)quinazoline-8-carboxamide (chiral)

The title compound was synthesized according to the procedure described for the preparation of Example 1 by coupling 5-Bromo-quinazoline-8-carbonitrile with (S)-tert-butyl 3-(aminomethyl)pyrrolidine-1-carboxylate, followed by hydrolysis of the nitrile intermediate. LC-MS (M+H=273, obsd.=272.1/273.1).

P70S6K IC$_{50}$: 4800 nM AKT IC$_{50}$: >100000 nM

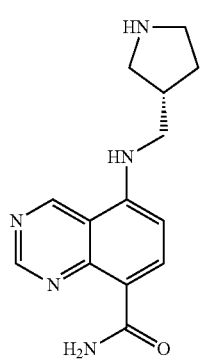 [SMILES: NC(=O)c1ccc(NC[C@H]2CCNC2)c2cncnc12]

Example 61

(S)-5-((pyrrolidin-3-ylmethyl)amino)quinazoline-8-carboxamide (chiral)

The title compound was synthesized according to the procedure described for the preparation of Example 1 by coupling 5-Bromo-quinazoline-8-carbonitrile with (R)-tert-butyl 3-(aminomethyl)pyrrolidine-1-carboxylate, followed by hydrolysis of the nitrile intermediate. LC-MS (M+H=273, obsd.=272.1/273.1).

P70S6K IC$_{50}$: 1700 nM AKT IC$_{50}$: >100000 nM

68

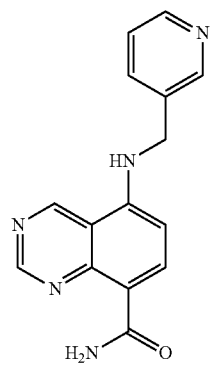 [SMILES: NC(=O)c1ccc(NCc2cccnc2)c2cncnc12]

Example 62

5-((pyridin-3-ylmethyl)amino)quinazoline-8-carboxamide

The title compound was synthesized according to the procedure described for the preparation of Example 1 by coupling 5-Bromo-quinazoline-8-carbonitrile with pyridin-3-ylmethanamine, followed by hydrolysis of the nitrile intermediate. LC-MS (M+H=279, obsd.=280.1/281.1).

P70S6K IC$_{50}$: 1600 nM AKT IC$_{50}$: 70000 nM

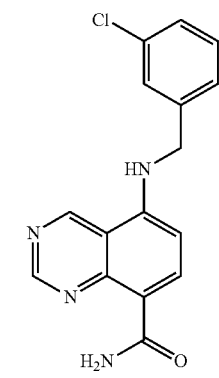 [SMILES: NC(=O)c1ccc(NCc2cccc(Cl)c2)c2cncnc12]

Example 63

5-((3-chlorobenzyl)amino)quinazoline-8-carboxamide

The title compound was synthesized according to the procedure described for the preparation of Example 1 by coupling 5-Bromo-quinazoline-8-carbonitrile with (3-chlorophenyl)methanamine, followed by hydrolysis of the nitrile intermediate. LC-MS (M+H=313, obsd.=313.1/314.1).

P70S6K IC$_{50}$: 59.2 nM AKT IC$_{50}$: 12000 nM

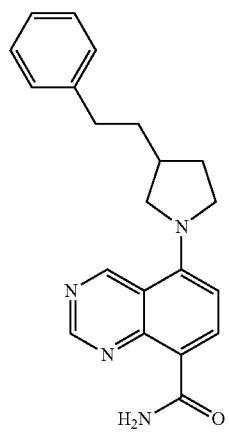 [SMILES: NC(=O)c1ccc(N2CCC(CCc3ccccc3)C2)c2cncnc12]

Example 64

5-(3-phenethylpyrrolidin-1-yl)quinazoline-8-carboxamide (racemic)

The title compound was synthesized according to the procedure described for the preparation of Example 1 by coupling 5-Bromo-quinazoline-8-carbonitrile with 3-phenethylpyrrolidine (racemic), followed by hydrolysis of the nitrile intermediate. LC-MS (M+H=347, obsd.=347.2/348.2).

P70S6K $IC_{50}$: 240 nM AKT $IC_{50}$: 3100 nM

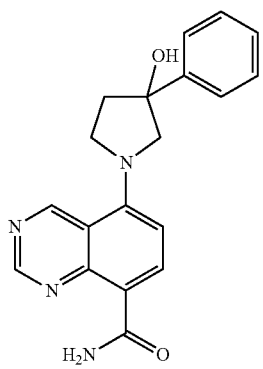

Example 66

5-(3-hydroxy-3-phenylpyrrolidin-1-yl)quinazoline-8-carboxamide (racemic)

The title compound was synthesized according to the procedure described for the preparation of Example 1 by coupling 5-Bromo-quinazoline-8-carbonitrile with 3-phenylpyrrolidin-3-ol (racemic), followed by hydrolysis of the nitrile intermediate. LC-MS (M+H=335, obsd.=335.1/336.1).

P70S6K $IC_{50}$: 1800 nM AKT $IC_{50}$: >100000 nM

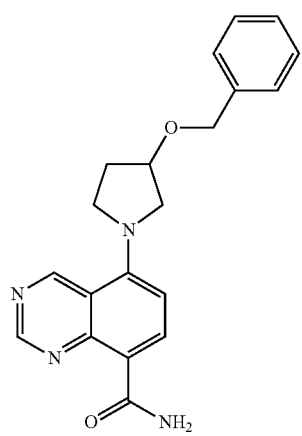 [SMILES: NC(=O)c1ccc(N2CCC(OCc3ccccc3)C2)c2cncnc12]

Example 65

5-(3-(benzyloxy)pyrrolidin-1-yl)quinazoline-8-carboxamide (racemic)

The title compound was synthesized according to the procedure described for the preparation of Example 1 by coupling 5-Bromo-quinazoline-8-carbonitrile with 3-(benzyloxy)pyrrolidine (racemic), followed by hydrolysis of the nitrile intermediate. LC-MS (M+H=349, obsd.=349.1/350.1).

P70S6K $IC_{50}$: 710 nM AKT $IC_{50}$: >100000 nM

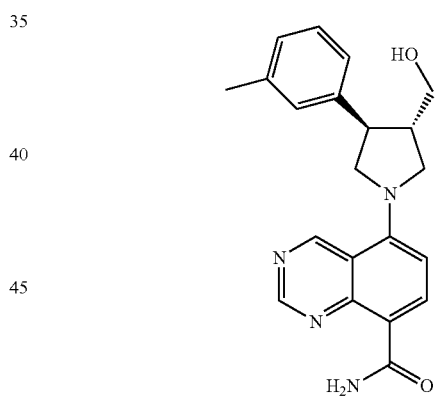

Example 67

5-((3S,4R)-3-(hydroxymethyl)-4-(m-tolyl)pyrrolidin-1-yl)quinazoline-8-carboxamide (chiral)

The title compound was synthesized according to the procedure described for the preparation of Example 1 by coupling 5-Bromo-quinazoline-8-carbonitrile with ((3S,4R)-4-(m-tolyl)pyrrolidin-3-yl)methanol, followed by hydrolysis of the nitrile intermediate. LC-MS (M+H=363, obsd.=363.2/364.1).

P70S6K $IC_{50}$: 190 nM AKT $IC_{50}$: 8200 nM

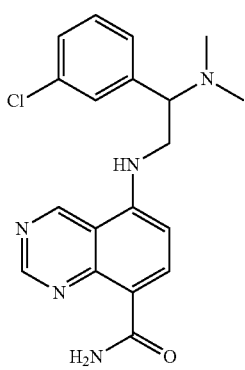 [SMILES: CN(C)C(CNc1ccc(C(N)=O)c2ncncc12)c1cccc(Cl)c1]

Example 68

5-((2-(3-chlorophenyl)-2-(dimethylamino)ethyl)amino)quinazoline-8-carboxamide (racemic)

The title compound was synthesized according to the procedure described for the preparation of Example 1 by coupling 5-Bromo-quinazoline-8-carbonitrile with 1-(3-chlorophenyl)-N1,N1-dimethylethane-1,2-diamine (racemic), followed by hydrolysis of the nitrile intermediate. LC-MS (M+H=370, obsd.=370.1/371.1).

P70S6K IC$_{50}$: 2600 nM AKT IC$_{50}$: >100000 nM

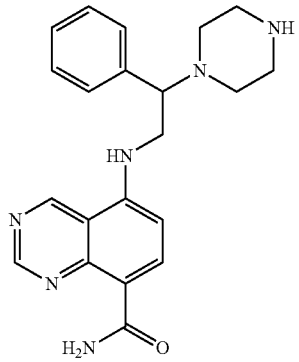 [SMILES: NC(=O)c1ccc(NCC(c2ccccc2)N2CCNCC2)c2cncnc12]

Example 69

5-((2-phenyl-2-(piperazin-1-yl)ethyl)amino)quinazoline-8-carboxamide (racemic)

The title compound was synthesized according to the procedure described for the preparation of Example 1 by coupling 5-Bromo-quinazoline-8-carbonitrile with tert-butyl 4-(2-amino-1-phenylethyl)piperazine-1-carboxylate (racemic), followed by hydrolysis of the nitrile intermediate. LC-MS (M+H=363, obsd.=363.2/364.1).

P70S6K IC$_{50}$: 170 nM AKT IC$_{50}$: 10000 nM

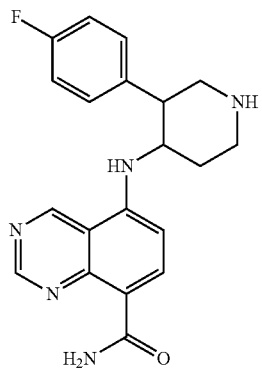 [SMILES: NC(=O)c1ccc(NC2CCNCC2c2ccc(F)cc2)c2cncnc12]

Example 70

5-((3-(4-fluorophenyl)piperidin-4-yl)amino)quinazoline-8-carboxamide (diasteromeric racemic mixture)

The title compound was synthesized according to the procedure described for the preparation of Example 1 by coupling 5-Bromo-quinazoline-8-carbonitrile with tert-butyl 4-amino-3-(4-fluorophenyl)piperidine-1-carboxylate (diastereomeric racemic mixtures), followed by hydrolysis of the nitrile intermediate. LC-MS (M+H=366, obsd.=366.1/367.2).

P70S6K IC$_{50}$: 550 nM AKT IC$_{50}$: 2500 nM

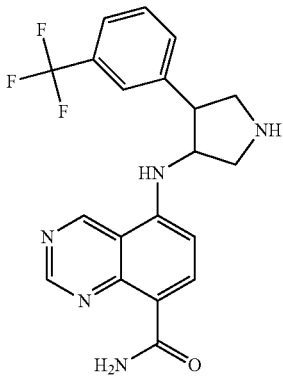 [SMILES: NC(=O)c1ccc(NC2CNCC2c2cccc(C(F)(F)F)c2)c2cncnc12]

Example 71

5-((4-(3-(trifluoromethyl)phenyl)pyrrolidin-3-yl)amino)quinazoline-8-carboxamide (diasteromeric racemic mixtures)

The title compound was synthesized according to the procedure described for the preparation of Example 1 by coupling 5-Bromo-quinazoline-8-carbonitrile with tert-butyl 3-amino-4-(3-(trifluoromethyl)phenyl)pyrrolidine-1-carboxylate (diastereomeric racemic mixtures), followed by hydrolysis of the nitrile intermediate. LC-MS (M+H=402, obsd.=402.2).

P70S6K IC$_{50}$: 21 nM AKT IC$_{50}$: 4500 nM

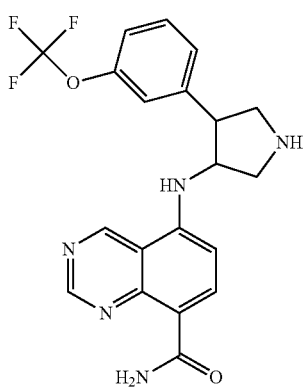 [SMILES: NC(=O)c1ccc(NC2CNCC2c2cccc(OC(F)(F)F)c2)c2cncnc12]

Example 72

5-((4-(3-(trifluoromethoxy)phenyl)pyrrolidin-3-yl)amino)quinazoline-8-carboxamide (diasteromeric racemic mixtures)

The title compound was synthesized according to the procedure described for the preparation of Example 1 by coupling 5-Bromo-quinazoline-8-carbonitrile with tert-butyl 3-amino-4-(3-(trifluoromethoxy)phenyl)pyrrolidine-1-carboxylate (diastereomeric racemic mixtures), followed by hydrolysis of the nitrile intermediate. LC-MS (M+H=418, obsd.=418.2/418.9).

P70S6K IC$_{50}$: 100 nM AKT IC$_{50}$: >100000 nM

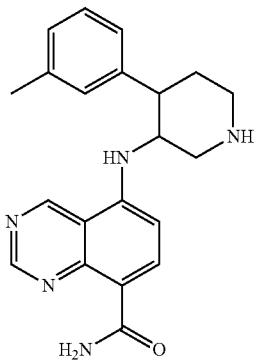 [SMILES: Cc1cccc(C2CCNCC2Nc2ccc(C(N)=O)c3ncncc23)c1]

Example 73

5-((4-(m-tolyl)piperidin-3-yl)amino)quinazoline-8-carboxamide (diasteromeric racemic mixtures)

The title compound was synthesized according to the procedure described for the preparation of Example 1 by coupling 5-Bromo-quinazoline-8-carbonitrile with tert-butyl 3-amino-4-(m-tolyl)piperidine-1-carboxylate (diastereomeric racemic mixtures), followed by hydrolysis of the nitrile intermediate. LC-MS (M+H=362, obsd.=362.2/363.2).

P70S6K IC$_{50}$: 390 nM AKT IC$_{50}$: 9000 nM

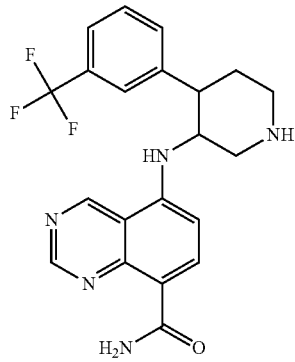 [SMILES: NC(=O)c1ccc(NC2CNCCC2c2cccc(C(F)(F)F)c2)c2cncnc12]

Example 74

5-((4-(3-(trifluoromethyl)phenyl)piperidin-3-yl)amino)quinazoline-8-carboxamide (diasteromeric racemic mixtures)

The title compound was synthesized according to the procedure described for the preparation of Example 1 by coupling 5-bromo-quinazoline-8-carbonitrile with tert-butyl 3-amino-4-(3-(trifluoromethyl)phenyl)piperidine-1-carboxylate (diastereomeric racemic mixtures), followed by hydrolysis of the nitrile intermediate. LC-MS (M+H=416, obsd.=416.2/417.2).

P70S6K IC$_{50}$: 140 nM AKT IC$_{50}$: 2100 nM

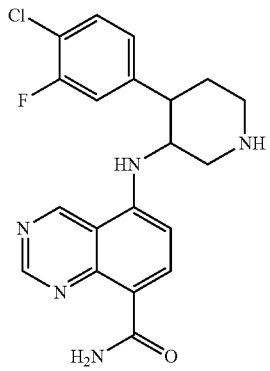 [SMILES: NC(=O)c1ccc(NC2CNCCC2c2ccc(Cl)c(F)c2)c2cncnc12]

Example 75

5-((4-(4-chloro-3-fluorophenyl)piperidin-3-yl)amino)quinazoline-8-carboxamide (diasteromeric racemic mixtures)

The title compound was synthesized according to the procedure described for the preparation of Example 1 by coupling 5-Bromo-quinazoline-8-carbonitrile with tert-butyl 3-amino-4-(4-chloro-3-fluorophenyl)piperidine-1-carboxylate (diastereomeric racemic mixtures), followed by hydrolysis of the nitrile intermediate. LC-MS (M+H=400.8, obsd.=400.2).

P70S6K IC$_{50}$: 8.1 nM AKT IC$_{50}$: 130 nM

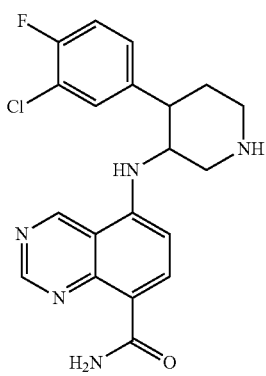 [SMILES: NC(=O)c1ccc(NC2CNCCC2c2ccc(F)c(Cl)c2)c2cncnc12]

Example 76

5-((4-(3-chloro-4-fluorophenyl)piperidin-3-yl)amino)quinazoline-8-carboxamide (diasteromeric racemic mixtures)

The title compound was synthesized according to the procedure described for the preparation of Example 1 by coupling 5-bromo-quinazoline-8-carbonitrile with tert-butyl 3-amino-4-(3-chloro-4-fluorophenyl)piperidine-1-carboxylate (diastereomeric racemic mixtures), followed by hydrolysis of the nitrile intermediate. LC-MS (M+H=400.8, obsd.=400.1/401.1).

P70S6K $IC_{50}$: 33 nM AKT $IC_{50}$: 570 nM

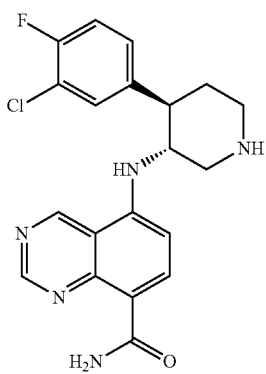 [SMILES: NC(=O)c1ccc(N[C@H]2CNCC[C@@H]2c2ccc(F)c(Cl)c2)c2cncnc12]

Example 77

5-(((3R,4R)-4-(3-chloro-4-fluorophenyl)piperidin-3-yl)amino)quinazoline-8-carboxamide (chiral, one of the enantiomers of Example 76 with unknown absolute configuration)

The title compound was separated from the diasteromeric mixture (Example 76) via chiral SFC. LC-MS (M+H=400.8, obsd.=400.1/401.1). $^1$HNMR (MeOH-d4) δ 1.16 (m, 1H), 1.31 (m, 1H), 1.78 (m, 1H), 2.34 (m, 1H), 2.89 (m, 1H), 3.20-3.32 (m, 3H), 6.29 (m, 1H), 6.97 (m, 1H), 7.25 (m, 1H), 7.39 (m, 1H), 8.33 (m, 1H), 9.21 (s, 1H), 9.93 (s, 1H).

P70S6K $IC_{50}$: 50 nM AKT $IC_{50}$: 850 nM

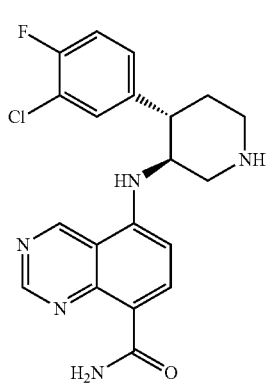 [SMILES: NC(=O)c1ccc(N[C@@H]2CNCC[C@H]2c2ccc(F)c(Cl)c2)c2cncnc12]

Example 78

5-(((3S,4S)-4-(3-chloro-4-fluorophenyl)piperidin-3-yl)amino)quinazoline-8-carboxamide (chiral, one of the enantiomers of Example 76 with unknown absolute configuration)

The title compound was separated from the diasteromeric mixture (Example 76) via chiral SFC. LC-MS (M+H=400.8, obsd.=400.2).

P70S6K $IC_{50}$: 350 nM AKT $IC_{50}$: 5700 nM

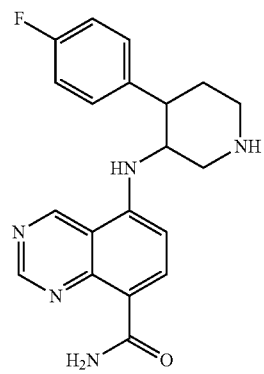 [SMILES: NC(=O)c1ccc(NC2CNCCC2c2ccc(F)cc2)c2cncnc12]

Example 79

5-((4-(4-fluorophenyl)piperidin-3-yl)amino)quinazoline-8-carboxamide (diasteromeric racemic mixtures)

The title compound was synthesized according to the procedure described for the preparation of Example 1 by coupling 5-bromo-quinazoline-8-carbonitrile with tert-butyl 3-amino-4-(4-fluorophenyl)piperidine-1-carboxylate (diastereomeric racemic mixtures), followed by hydrolysis of the nitrile intermediate. LC-MS (M+H=366, obsd.=366.1/367.1).

P70S6K $IC_{50}$: 290 nM AKT $IC_{50}$: 2000 nM

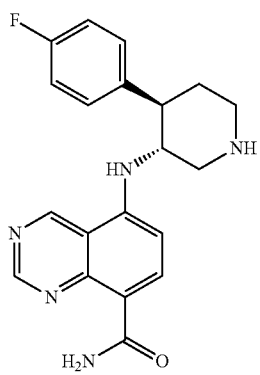 [SMILES: NC(=O)c1ccc(N[C@H]2CNCC[C@@H]2c2ccc(F)cc2)c2cncnc12]

Example 80

5-(((3R,4R)-4-(4-fluorophenyl)piperidin-3-yl)amino)quinazoline-8-carboxamide (chiral, one of the enantiomers of Example 79 with unknown absolute configuration)

The title compound was separated from the diasteromeric mixture (Example 79) via chiral SFC. LC-MS (M+H=366, obsd.=366.2).

P70S6K IC$_{50}$: 290 nM AKT IC$_{50}$: 2200 nM

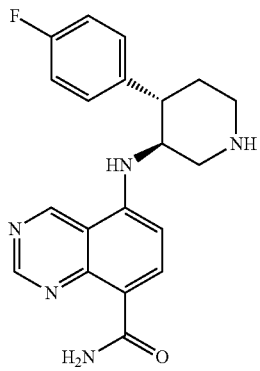 [SMILES: NC(=O)c1ccc(N[C@@H]2CNCC[C@H]2c2ccc(F)cc2)c2cncnc12]

Example 81

5-(((3S,4S)-4-(4-fluorophenyl)piperidin-3-yl)amino)quinazoline-8-carboxamide (chiral, one of the enantiomers of Example 79 with unknown absolute configuration)

The title compound was separated from the diasteromeric mixture (Example 79) via chiral SFC. LC-MS (M+H=366, obsd.=366.1).

P70S6K IC$_{50}$: 52 nM AKT IC$_{50}$: 900 nM

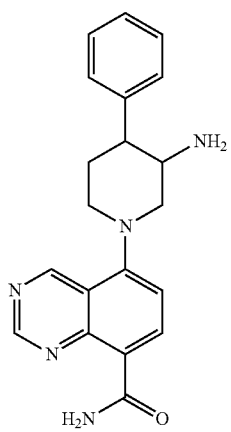 [SMILES: NC(=O)c1ccc(N2CCC(c3ccccc3)C(N)C2)c2cncnc12]

Example 82

5-(3-amino-4-phenylpiperidin-1-yl)quinazoline-8-carboxamide (racemic)

The title compound was synthesized according to the procedure described for the preparation of Example 1 by coupling 5-bromo-quinazoline-8-carbonitrile with 4-phenyl-piperidin-3-ylamine, followed by hydrolysis of the nitrile intermediate. LC-MS (M+H=347, obsd=348).

P70S6K IC$_{50}$: 120 nM

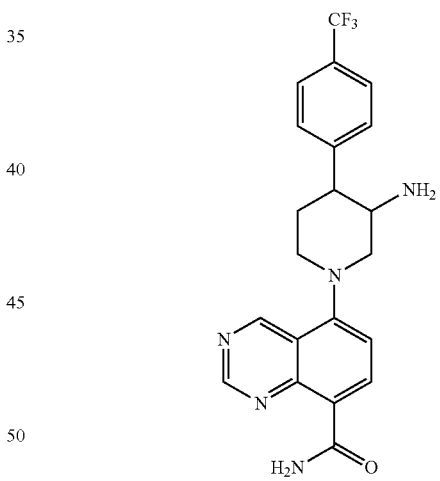

Example 83

5-(3-amino-4-(4-(trifluoromethyl)phenyl)piperidin-1-yl)quinazoline-8-carboxamide (racemic)

The title compound was synthesized according to the procedure described for the preparation of Example 1 by coupling 5-bromo-quinazoline-8-carbonitrile with 4-(4-trifluoromethyl-phenyl)-piperidin-3-ylamine, followed by hydrolysis of the nitrile intermediate. LC-MS (M+H=415, obsd=416).

P70S6K IC$_{50}$: 350 nM

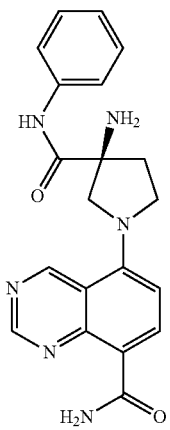 [SMILES: NC(=O)c1ccc(N2CC[C@@](N)(C(=O)Nc3ccccc3)C2)c2cncnc12]

Example 84

(S)-5-(3-amino-3-(phenylcarbamoyl)pyrrolidin-1-yl)quinazoline-8-carboxamide (pure enantiomer, absolute structure unknown)

The title compound was isolated by chiral HPLC from Example 15. LC-MS (M+H=376, obsd=377).

P70S6K $IC_{50}$: 2150 nM

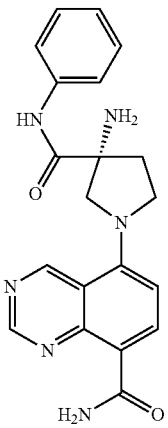 [SMILES: NC(=O)c1ccc(N2CC[C@](N)(C(=O)Nc3ccccc3)C2)c2cncnc12]

Example 85

(R)-5-(3-amino-3-(phenylcarbamoyl)pyrrolidin-1-yl)quinazoline-8-carboxamide (pure enantiomer, absolute structure unknown)

The title compound was isolated by chiral HPLC from Example 15. LC-MS (M+H=376, obsd=377).

P70S6K $IC_{50}$: 11500 nM

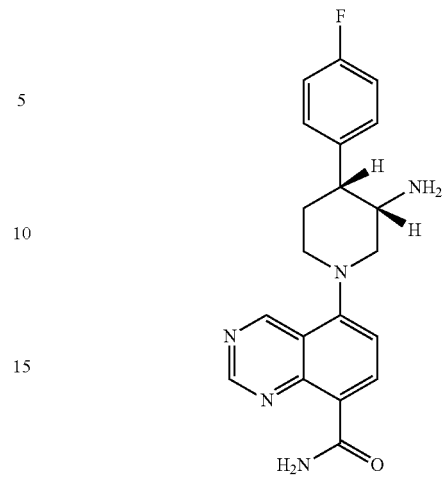

Example 86

5-[(3S,4R)-3-Amino-4-(4-fluoro-phenyl)-piperidin-1-yl]-quinazoline-8-carboxylic acid amide (racemic_cis)

The title compound was synthesized according to the procedure described for the preparation of Example 1 by coupling 5-bromo-quinazoline-8-carbonitrile with cis-4-(4-fluorophenyl)piperidin-3-amine, followed by hydrolysis of the nitrile intermediate. LC-MS (M+H=366, obsd=366).

P70S6K $IC_{50}$: 250 nM

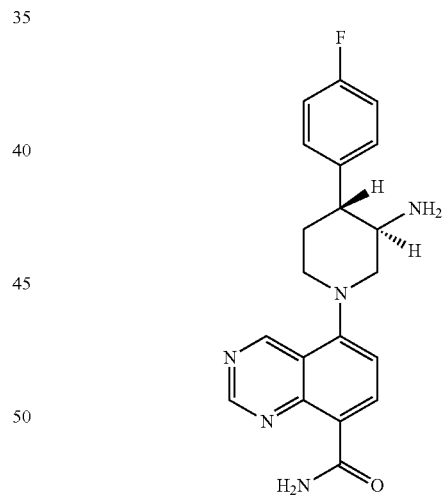

Example 87

5-[(3R,4R)-3-Amino-4-(4-fluoro-phenyl)-piperidin-1-yl]-quinazoline-8-carboxylic acid amide. (racemic_trans)

The title compound was synthesized according to the procedure described for the preparation of Example 1 by coupling 5-bromo-quinazoline-8-carbonitrile with trans-4-(4-fluorophenyl)piperidin-3-amine, followed by hydrolysis of the nitrile intermediate. LC-MS (M+H=366, obsd=366).

P70S6K $IC_{50}$: 7100 nM

81

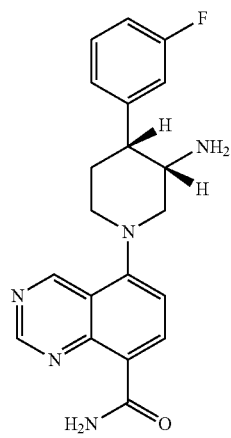 [SMILES: NC(=O)c1ccc(N2CC[C@H](c3cccc(F)c3)[C@H](N)C2)c2cncnc12]

Example 88

5-[(3S,4R)-3-Amino-4-(3-fluoro-phenyl)-piperidin-1-yl]-quinazoline-8-carboxylic acid amide (racemic_cis)

The title compound was synthesized according to the procedure described for the preparation of Example 1 by coupling 5-bromo-quinazoline-8-carbonitrile with cis-4-(3-fluorophenyl)piperidin-3-amine, followed by hydrolysis of the nitrile intermediate. LC-MS (M+H=366, obsd=366).

P70S6K IC$_{50}$: 17100 nM

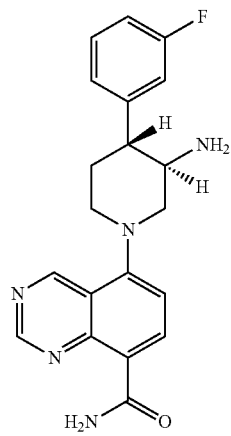 [SMILES: NC(=O)c1ccc(N2CC[C@H](c3cccc(F)c3)[C@@H](N)C2)c2cncnc12]

Example 89

5-[(3R,4R)-3-Amino-4-(3-fluoro-phenyl)-piperidin-1-yl]-quinazoline-8-carboxylic acid amide (racemic_trans)

The title compound was synthesized according to the procedure described for the preparation of Example 1 by coupling 5-bromo-quinazoline-8-carbonitrile with trans-4-(3-fluorophenyl)piperidin-3-amine, followed by hydrolysis of the nitrile intermediate. LC-MS (M+H=366, obsd=366).

P70S6K IC$_{50}$: 2400 nM

82

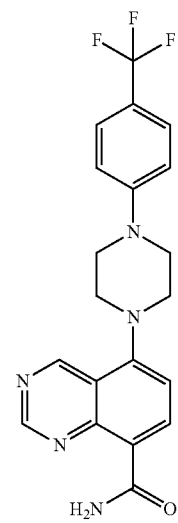 [SMILES: NC(=O)c1ccc(N2CCN(c3ccc(C(F)(F)F)cc3)CC2)c2cncnc12]

Example 90

5-[4-(4-Trifluoromethyl-phenyl)-piperazin-1-yl]-quinazoline-8-carboxylic acid amide The title compound was synthesized according to the procedure described for the preparation of Example 1 by coupling with 5-bromo-quinazoline-8-carbonitrile and 1-(4-trifluoromethyl-phenyl)-piperazine, followed by hydrolysis of the nitrile intermediate. LC-MS. (M+H=402, obsd=402).

P70S6K IC$_{50}$: 24000 nM AKT IC$_{50}$: >100000 nM

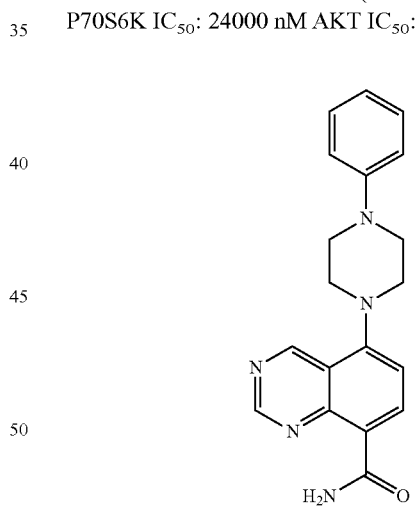

Example 91

5-[4-phenyl-piperazin-1-yl]-quinazoline-8-carboxylic acid amide

The title compound was synthesized according to the procedure described for the preparation of Example 1 by coupling with 5-bromo-quinazoline-8-carbonitrile and 1-phenylpiperazine, followed by hydrolysis of the nitrile intermediate. LC-MS. (M+H=334, obsd=334).

P70S6K IC$_{50}$: 3000 nM AKT IC$_{50}$: 15000 nM

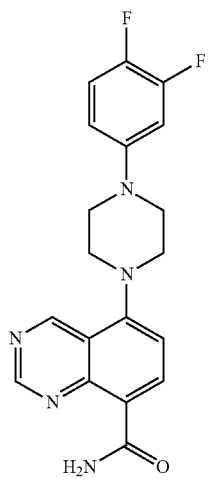 [SMILES: NC(=O)c1ccc(N2CCN(c3ccc(F)c(F)c3)CC2)c2cncnc12]

Example 92

5-[4-(3,4-difluoro-phenyl)-piperazin-1-yl]-quinazoline-8-carboxylic acid amide

The title compound was synthesized according to the procedure described for the preparation of Example 1 by coupling with 5-bromo-quinazoline-8-carbonitrile and 1-(3,4-difluoro-phenyl)-piperazine, followed by hydrolysis of the nitrile intermediate. LC-MS. (M+H=370, obsd=370).

P70S6K $IC_{50}$: 1000 nM AKT $IC_{50}$: >100000 nM

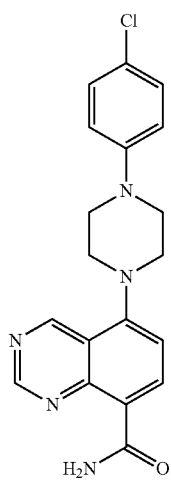 [SMILES: NC(=O)c1ccc(N2CCN(c3ccc(Cl)cc3)CC2)c2cncnc12]

Example 93

5-[4-(4-chloro-phenyl)-piperazin-1-yl]-quinazoline-8-carboxylic acid amide

The title compound was synthesized according to the procedure described for the preparation of Example 1 by coupling with 5-bromo-quinazoline-8-carbonitrile and 1-(4-chlorophenyl)piperazine, followed by hydrolysis of the nitrile intermediate. LC-MS. (M+H=368, obsd=368).

P70S6K $IC_{50}$: 1000 nM

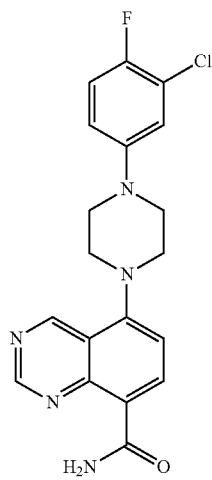 [SMILES: NC(=O)c1ccc(N2CCN(c3ccc(F)c(Cl)c3)CC2)c2cncnc12]

Example 94

5-[4-(3-chloro-4-fluorophenyl)-piperazin-1-yl]-quinazoline-8-carboxylic acid amide The title compound was synthesized according to the procedure described for the preparation of Example 1 by coupling with 5-bromo-quinazoline-8-carbonitrile and 1-(3-chloro-4-fluoro-phenyl)-piperazine, followed by hydrolysis of the nitrile intermediate. LC-MS. (M+H=386, obsd=386).

P70S6K $IC_{50}$: 12000 nM AKT $IC_{50}$: >100000 nM

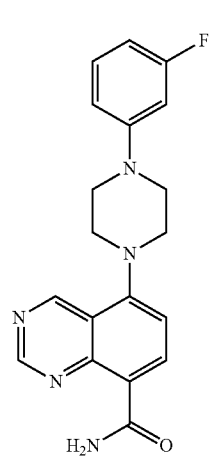 [SMILES: NC(=O)c1ccc(N2CCN(c3cccc(F)c3)CC2)c2cncnc12]

Example 95

5-[4-(3-fluoro-phenyl)-piperazin-1-yl]-quinazoline-8-carboxylic acid amide

The title compound was synthesized according to the procedure described for the preparation of Example 1 by coupling with 5-bromo-quinazoline-8-carbonitrile and 1-(3-fluoro-phenyl)-piperazine, followed by hydrolysis of the nitrile intermediate. LC-MS. (M+H=352, obsd=352).

P70S6K $IC_{50}$: 770 nM AKT $IC_{50}$: 6400 nM

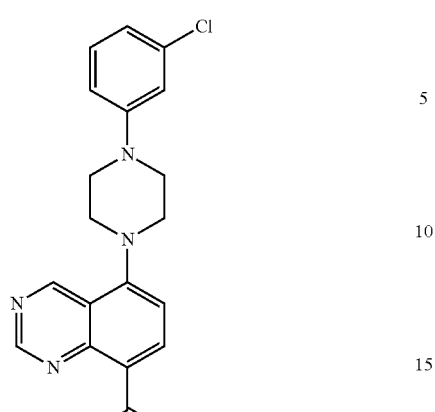

Example 96

5-[4-(3-chloro-phenyl)-piperazin-1-yl]-quinazoline-8-carboxylic acid amide

The title compound was synthesized according to the procedure described for the preparation of Example 1 by coupling with 5-bromo-quinazoline-8-carbonitrile and 1-(3-chlorol-phenyl)-piperazine, followed by hydrolysis of the nitrile intermediate. LC-MS. (M+H=368, obsd=368).

P70S6K IC$_{50}$: 10000 nM AKT IC$_{50}$: >100000 nM

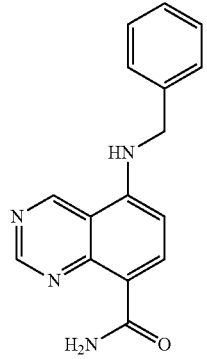 [SMILES: NC(=O)c1ccc(NCc2ccccc2)c2cncnc12]

Example 97

5-(benzylamino)quinazoline-8-carboxamide

The title compound was synthesized according to the procedure described for the preparation of Example 1 by coupling with benzylamine, followed by hydrolysis of the nitrile intermediate. LC-MS (M+H=261, obsd=261). $^1$H NMR (400 MHz, DMSO) δ 9.96 (s, 1H), 9.30 (s, 1H), 8.83 (t, J=5.6 Hz, 1H), 8.11 (d, J=8.6 Hz, 1H), 7.42 (d, J=7.7 Hz, 2H), 7.35 (t, J=7.3 Hz, 2H), 7.27 (t, J=6.9 Hz, 1H), 6.62 (d, J=8.7 Hz, 1H), 4.64 (d, J=5.8 Hz, 2H).

p70S6K IC$_{50}$: =690 nM AKT IC$_{50}$: =57000 nM

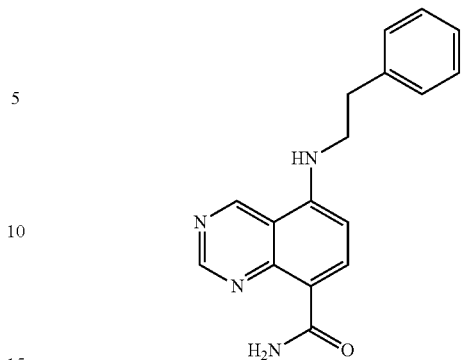

Example 98

5-(phenethylamino)quinazoline-8-carboxamide

The title compound was synthesized according to the procedure described for the preparation of Example 1 by coupling with 2-phenethylamine, followed by hydrolysis of the nitrile intermediate. LC-MS (M+H=293, obsd=293). $^1$H NMR (500 MHz, dmso) δ 9.84 (s, 1H), 9.69 (d, J=3.9 Hz, 1H), 9.26 (s, 1H), 8.56 (d, J=8.7 Hz, 1H), 7.86 (t, J=5.3 Hz, 1H), 7.52 (d, J=3.9 Hz, 1H), 7.39-7.27 (m, 4H), 7.26-7.19 (m, 1H), 6.85 (d, J=8.8 Hz, 1H), 3.62-3.52 (m, 2H), 3.04-2.97 (m, 2H).

p70S6K IC$_{50}$: =89 nM; AKT IC$_{50}$: =5600 nM

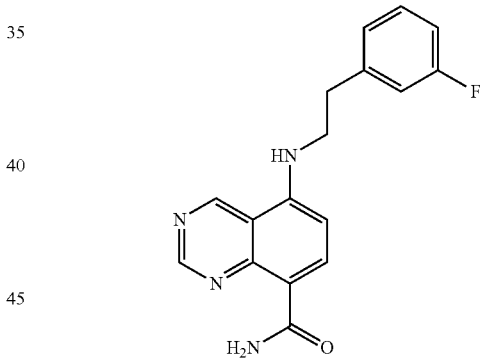

Example 99

5-[2-(3-fluorophenyl)ethylamino]quinazoline-8-carboxamide

The title compound was synthesized according to the procedure described for the preparation of Example 1 by coupling with 2-(3-fluorophenyl)ethanamine, followed by hydrolysis of the nitrile intermediate. LC-MS (M+H=311, obsd=311). $^1$H NMR (500 MHz, dmso) δ 9.83 (s, 1H), 9.69 (d, J=3.9 Hz, 1H), 9.26 (s, 1H), 8.56 (d, J=8.7 Hz, 1H), 7.84 (t, J=5.5 Hz, 1H), 7.52 (d, J=3.9 Hz, 1H), 7.38-7.30 (m, 1H), 7.24-7.18 (m, 1H), 7.16 (d, J=7.6 Hz, 1H), 7.04 (td, J=8.6, 2.5 Hz, 1H), 6.87 (d, J=8.8 Hz, 1H), 3.59 (dd, J=13.9, 6.4 Hz, 2H), 3.06-2.98 (m, 2H).

p70S6K IC$_{50}$: =120 nM AKT IC$_{50}$: =2400 nM

87

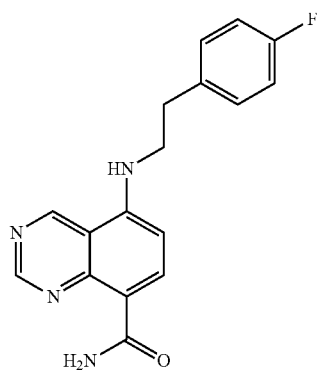 [SMILES: NC(=O)c1ccc(NCCc2ccc(F)cc2)c2cncnc12]

Example 100

5-[2-(4-fluorophenyl)ethylamino]quinazoline-8-carboxamide

The title compound was synthesized according to the procedure described for the preparation of Example 1 by coupling with 2-(4-fluorophenyl)ethanamine, followed by hydrolysis of the nitrile intermediate. LC-MS (M+H=311, obsd=311). $^1$H NMR (500 MHz, dmso) δ 9.83 (s, 1H), 9.69 (d, J=3.9 Hz, 1H), 9.26 (s, 1H), 8.55 (d, J=8.7 Hz, 1H), 7.84 (t, J=5.4 Hz, 1H), 7.52 (d, J=3.8 Hz, 1H), 7.39-7.31 (m, 2H), 7.16-7.07 (m, 2H), 6.85 (d, J=8.8 Hz, 1H), 3.55 (dd, J=14.0, 6.4 Hz, 2H), 3.03-2.95 (m, 2H).

p70S6K IC$_{50}$: =290 nM AKT IC$_{50}$: =4800 nM

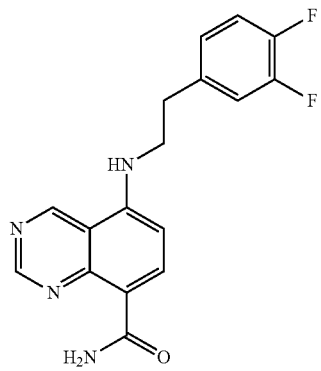 [SMILES: NC(=O)c1ccc(NCCc2ccc(F)c(F)c2)c2cncnc12]

Example 101

5-[2-(3,4-difluorophenyl)ethylamino]quinazoline-8-carboxamide

The title compound was synthesized according to the procedure described for the preparation of Example 1 by coupling with 2-(3,4-difluorophenyl)ethanamine, followed by hydrolysis of the nitrile intermediate. LC-MS (M+H=329, obsd=329). $^1$H NMR (500 MHz, dmso) δ 9.82 (s, 1H), 9.69 (d, J=3.9 Hz, 1H), 9.26 (s, 1H), 8.56 (d, J=8.7 Hz, 1H), 7.81 (t, J=5.3 Hz, 1H), 7.53 (d, J=3.7 Hz, 1H), 7.45 (ddd, J=12.0, 7.9, 2.0 Hz, 1H), 7.35 (dt, J=10.9, 8.5 Hz, 1H), 7.15 (s, 1H), 6.87 (d, J=8.8 Hz, 1H), 3.57 (dd, J=13.7, 6.4 Hz, 2H), 2.99 (t, J=7.3 Hz, 2H).

p70S6K IC$_{50}$: =360 nM AKT IC$_{50}$: =41000 nM

88

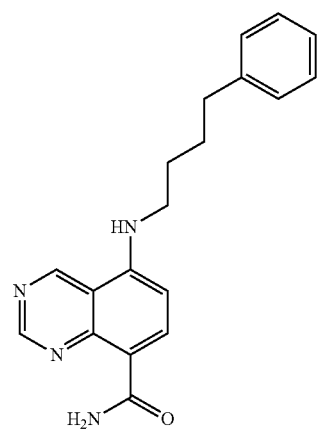 [SMILES: NC(=O)c1ccc(NCCCCc2ccccc2)c2cncnc12]

Example 102

5-(4-phenylbutylamino)quinazoline-8-carboxamide

The title compound was synthesized according to the procedure described for the preparation of Example 1 by coupling with 4-phenylbutan-1-amine, followed by hydrolysis of the nitrile intermediate. LC-MS (M+H=321, obsd=321). $^1$H NMR (500 MHz, dmso) δ 9.86 (s, 1H), 9.68 (d, J=3.9 Hz, 1H), 9.24 (s, 1H), 8.53 (d, J=8.7 Hz, 1H), 7.74 (t, J=5.2 Hz, 1H), 7.50 (d, J=3.9 Hz, 1H), 7.27 (t, J=7.6 Hz, 2H), 7.22 (d, J=7.0 Hz, 2H), 7.17 (t, J=7.2 Hz, 1H), 6.75 (d, J=8.8 Hz, 1H), 3.34 (dd, J=12.1, 6.8 Hz, 2H), 2.66 (t, J=7.1 Hz, 2H), 1.79-1.62 (m, 4H).

p70S6K IC$_{50}$: =87 nM AKT IC$_{50}$: >100000 nM

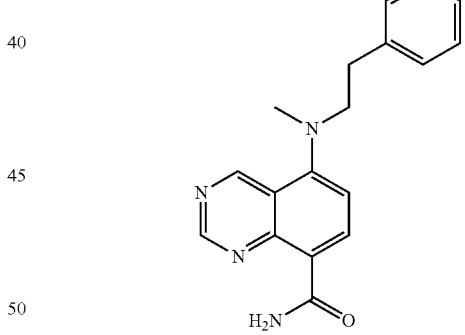

Example 103

5-[methyl(phenethyl)amino]quinazoline-8-carboxamide

The title compound was synthesized according to the procedure described for the preparation of Example 1 by coupling with N-methyl-2-phenylethanamine, followed by hydrolysis of the nitrile intermediate. LC-MS (M+H=307, obsd=307). $^1$H NMR (500 MHz, dmso) δ 9.71 (d, J=2.5 Hz, 1H), 9.48 (s, 1H), 9.29 (s, 1H), 8.59 (d, J=8.4 Hz, 1H), 7.76 (d, J=2.4 Hz, 1H), 7.32-7.19 (m, 5H), 7.18 (M, 1H), 3.60 (t, 2H), 3.13 (s, 3H), 2.99 (t, 2H).

p70S6K IC$_{50}$: =220 nM AKT IC$_{50}$: =14000 nM

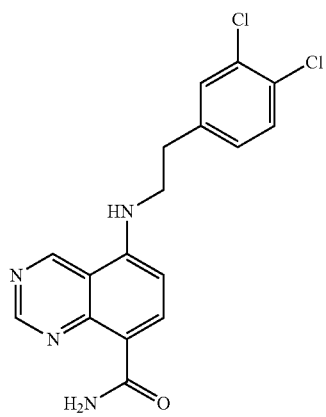 [SMILES: NC(=O)c1ccc(NCCc2ccc(Cl)c(Cl)c2)c2cncnc12]

Example 104

5-[2-(3,4-dichlorophenyl)ethylamino]quinazoline-8-carboxamide

The title compound was synthesized according to the procedure described for the preparation of Example 1 by coupling with 2-(3,4-dichlorophenyl)ethanamine, followed by hydrolysis of the nitrile intermediate. LC-MS (M+H=362, obsd=362). $^1$H NMR (500 MHz, cd$_3$od) δ 9.65 (s, 1H), 9.22 (s, 1H), 8.69 (d, J=8.8 Hz, 1H), 7.48 (d, J=1.9 Hz, 1H), 7.44 (d, J=8.2 Hz, 1H), 7.22 (dd, J=8.3, 2.0 Hz, 1H), 6.89 (d, J=8.8 Hz, 1H), 3.71-3.64 (m, 2H), 3.05 (t, J=7.3 Hz, 2H).

p70S6K IC$_{50}$: =98 nM AKT IC$_{50}$: >100000 nM

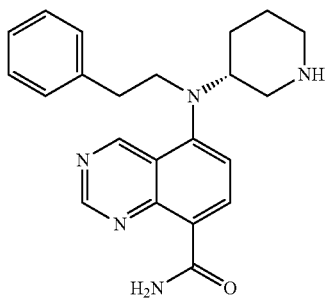 [SMILES: NC(=O)c1ccc(N(CCc2ccccc2)[C@@H]2CCCNC2)c2cncnc12]

Example 105

5-[phenethyl-[(3R)-3-piperidyl]amino]quinazoline-8-carboxamide (chiral)

The title compound was synthesized according to the procedure described for the preparation of Example 1 by coupling with (R)-tert-butyl 3-(phenethylamino)piperidine-1-carboxylate (Scheme 7), followed by hydrolysis of the nitrile intermediate and deprotection. LC-MS (M+H=376, obsd=376). $^1$H NMR (500 MHz, dmso) δ 10.34 (s, 1H), 8.39 (s, 1H), 7.95 (d, J=8.4 Hz, 1H), 7.41 (s, 1H), 7.32-7.06 (m, 5H), 6.88 (d, J=8.7 Hz, 1H), 5.56 (s, 1H), 3.57-3.47 (m, 1H), 3.26-3.10 (m, 2H), 2.93-2.74 (m, 3H), 2.68-2.60 (m, 1H), 2.42-2.33 (m, 1H), 2.07-1.99 (m, 1H), 1.93-1.75 (m, 2H), 1.74-1.56 (m, 2H), 1.27-1.19 (m, 1H).

p70S6K IC$_{50}$: =11000 nM AKT IC$_{50}$: >100000 nM

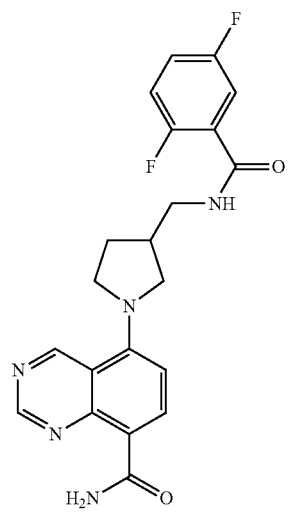 [SMILES: NC(=O)c1ccc(N2CCC(CNC(=O)c3cc(F)ccc3F)C2)c2cncnc12]

Example 106

5-(3-((2,5-difluorobenzamido)methyl)pyrrolidin-1-yl)quinazoline-8-carboxamide (racemic)

The title compound was synthesized according to the procedure described for the preparation of Example 1 by coupling with 2,5-difluoro-N-(pyrrolidin-3-ylmethyl)benzamide (racemic), followed by hydrolysis of the nitrile intermediate. LC-MS (M+H=412, obsd=412). 1H NMR (400 MHz, DMSO) δ 9.81 (s, 1H), 9.75 (d, J=4.2 Hz, 1H), 9.21 (s, 1H), 8.62 (s, 1H), 8.54 (d, J=8.8 Hz, 1H), 7.53 (s, 1H), 7.49-7.32 (m, 4H), 6.85 (d, J=8.9 Hz, 1H), 3.90-3.82 (m, 1H), 3.82-3.75 (m, 2H), 3.69-3.61 (m, 1H), 3.41 (ddd, J=34.0, 13.6, 7.3 Hz, 3H), 2.67-2.58 (m, 1H), 2.16 (dd, J=12.1, 6.2 Hz, 1H), 1.90-1.79 (m, 1H).

p70S6K IC50: 510 nM

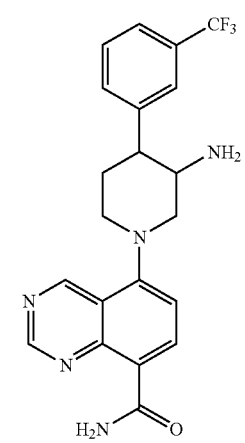 [SMILES: NC(=O)c1ccc(N2CCC(c3cccc(C(F)(F)F)c3)C(N)C2)c2cncnc12]

Example 107

5-[3-Amino-4-(3-trifluoromethyl-phenyl)-piperidin-1-yl]-quinazoline-8-carboxylic acid amide (racemic)

The title compound was synthesized according to the procedure described for the preparation of Example 1 by coupling with 5-bromo-quinazoline-8-carbonitrile and tert-butyl (4-(3-(trifluoromethyl)phenyl)piperidin-3-yl)carbamate, followed by hydrolysis of the nitrile intermediate and deprotection. LC-MS (M+H=416, obsd=416).

P70S6K IC$_{50}$: 380 nM AKt IC$_{50}$: 8100 nM

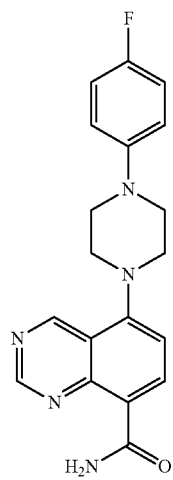

Example 108

5-[4-(4-fluorophenyl)-piperazin-1-yl]-quinazoline-8-carboxylic acid amide

The title compound was synthesized according to the procedure described for the preparation of Example 1 by coupling with 5-bromo-quinazoline-8-carbonitrile and 1-(4-fluorophenyl)piperazine, followed by hydrolysis of the nitrile intermediate. LC-MS. (M+H=352, obsd=352).

P70S6K IC$_{50}$: 2300 nM AKt IC$_{50}$: >100000 nM

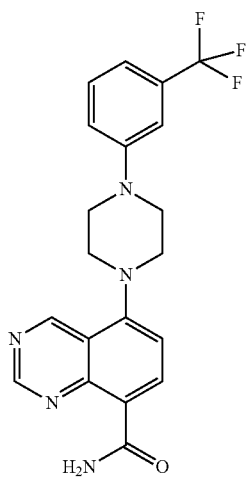 [SMILES: NC(=O)c1ccc(N2CCN(c3cccc(C(F)(F)F)c3)CC2)c2cncnc12]

Example 109

5-[4-(3-trifluoromethylphenyl)-piperazin-1-yl]-quinazoline-8-carboxylic acid amide The title compound was synthesized according to the procedure described for the preparation of Example 1 by coupling with 5-bromo-quinazoline-8-carbonitrile and 1-(3-trifluoromethylfluorophenyl)piperazine, followed by hydrolysis of the nitrile intermediate. LC-MS. (M+H=402, obsd=402).

P70S6K IC$_{50}$: 11000 nM AKt IC$_{50}$: 23000 nM

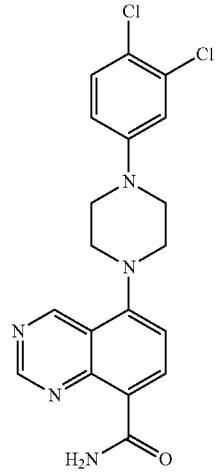 [SMILES: NC(=O)c1ccc(N2CCN(c3ccc(Cl)c(Cl)c3)CC2)c2cncnc12]

Example 110

5-[4-(3,4-dichlorophenyl)-piperazin-1-yl]-quinazoline-8-carboxylic acid amide

The title compound was synthesized according to the procedure described for the preparation of Example 1 by coupling with 5-bromo-quinazoline-8-carbonitrile and 1-(3,4-dichlorophenyl)-piperazine, followed by hydrolysis of the nitrile intermediate. LC-MS. (M+H=403, obsd=403).

P70S6K IC$_{50}$: >100000 nM AKt IC$_{50}$: >100000 nM

Example 111

5-[4-(5-chloro-2-methylphenyl)-piperazin-1-yl]-quinazoline-8-carboxylic acid amide The title compound was synthesized according to the procedure described for the preparation of Example 1 by coupling with 5-Bromo-quinazoline-8-carbonitrile and 1-(5-chloro-2-methylphenyl)piperazine, followed by hydrolysis of the nitrile intermediate. LC-MS. (M+H=382, obsd=382).

P70S6K IC$_{50}$: >100000 nM AKt IC$_{50}$: >100000 nM

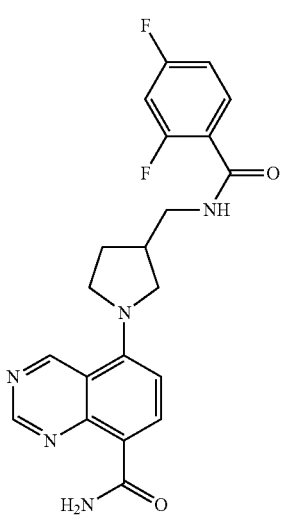 [SMILES: NC(=O)c1ccc(N2CCC(CNC(=O)c3ccc(F)cc3F)C2)c2cncnc12]

Example 112

5-{3-[(2,4-Difluoro-benzoylamino)-methyl]-pyrrolidin-1-yl}-quinazoline-8-carboxylic acid amide (racemic)

The title compound was synthesized according to the procedure described for the preparation of Example 1 by coupling with 2,4-difluoro-N-(pyrrolidin-3-ylmethyl)benzamide (racemic), followed by hydrolysis of the nitrile intermediate. LC-MS (M+H=412, obsd=412).
p70S6K IC50: 260 nM

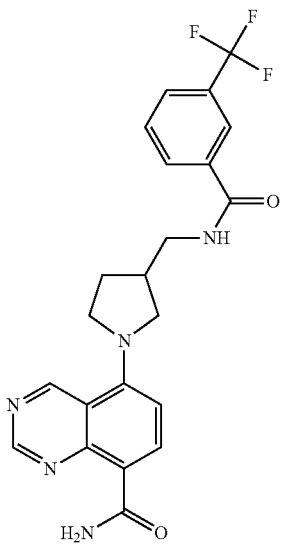 [SMILES: NC(=O)c1ccc(N2CCC(CNC(=O)c3cccc(C(F)(F)F)c3)C2)c2cncnc12]

Example 113

5-{3-[(3-Trifluoromethyl-benzoylamino)-methyl]-pyrrolidin-1-yl}-quinazoline-8-carboxylic acid amide (racemic)

The title compound was synthesized according to the procedure described for the preparation of Example 1 by coupling with N-(pyrrolidin-3-ylmethyl)-3-(trifluoromethyl) benzamide (racemic), followed by hydrolysis of the nitrile intermediate. LC-MS (M+H=444, obsd=444).
p70S6K IC50: nd nM

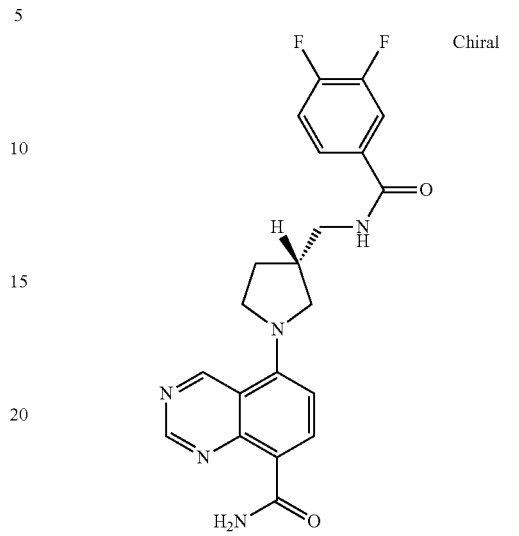

Example 114

5-{(R)-3-[(3,4-Difluoro-benzoylamino)-methyl]-pyrrolidin-1-yl}-quinazoline-8-carboxylic acid amide (pure enantiomer, absolute structure unknown)

The title compound was isolated by chiral HPLC from Example 54. LC-MS (M+H=412, obsd=412). 1H NMR (400 MHz, DMSO) δ 9.77 (d, J=26.9 Hz, 2H), 9.20 (s, 1H), 8.71 (s, 1H), 8.53 (d, J=7.2 Hz, 1H), 7.95-7.83 (m, 1H), 7.70 (d, J=13.6 Hz, 4H), 7.61-7.45 (m, 2H), 6.84 (d, J=8.5 Hz, 1H), 4.30-3.97 (m, 4H), 3.84 (dd, J=23.0, 14.6 Hz, 3H), 3.68-3.59 (m, 1H), 3.44 (s, 1H), 2.63 (dd, J=17.2, 8.6 Hz, 1H), 2.14 (s, 1H), 1.82 (s, 2H), 1.63 (s, 3H), 1.26 (d, J=18.5 Hz, 19H), 0.95-0.66 (m, 15H).
p70S6K IC$_{50}$: 470 nM

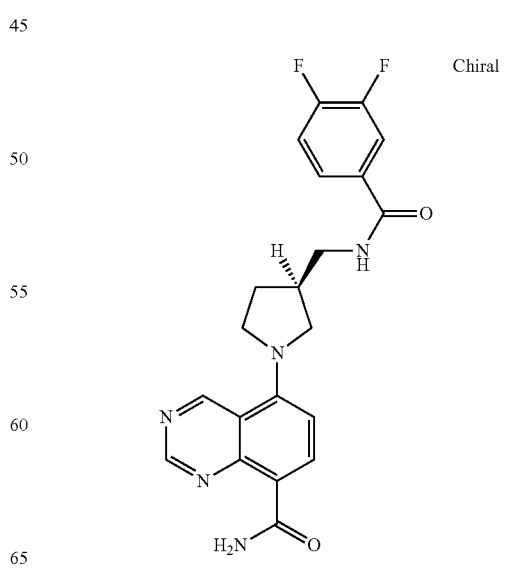

Example 115

5-{(S)-3-[(3,4-Difluoro-benzoylamino)-methyl]-pyrrolidin-1-yl}-quinazoline-8-carboxylic acid amide (pure enantiomer, absolute structure unknown)

The title compound was isolated by chiral HPLC from Example 54. LC-MS (M+H=412, obsd=412). $^1$H NMR (400 MHz, DMSO) δ 9.82 (s, 1H), 9.75 (s, 1H), 9.21 (s, 1H), 8.79 (s, 1H), 8.54 (d, J=8.8 Hz, 2H), 7.91 (s, 1H), 7.76 (s, 1H), 7.56 (d, J=10.0 Hz, 2H), 6.86 (d, J=9.2 Hz, 1H), 4.37 (s, 4H), 3.83 (d, J=28.4 Hz, 3H), 3.64 (s, 2H), 3.45 (d, J=6.2 Hz, 5H), 3.15 (d, J=29.4 Hz, 2H), 2.94 (s, 1H), 2.15 (s, 2H), 1.88 (s, 1H), 1.59 (s, 2H), 1.25 (s, 4H), 1.05 (dd, J=18.1, 12.1 Hz, 9H), 0.84 (s, 2H).

p70S6K IC$_{50}$: 450 nM

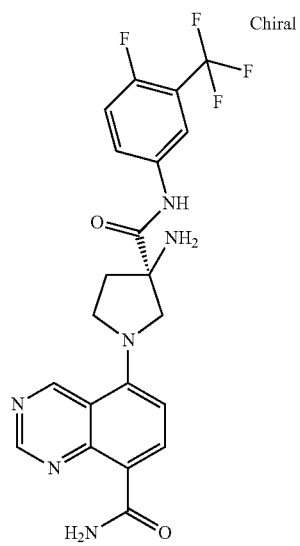

Example 116

5-[(S)-3-Amino-3-(4-fluoro-3-trifluoromethyl-phenylcarbamoyl)-pyrrolidin-1-yl]-quinazoline-8-carboxylic acid amide (pure enantiomer, absolute structure unknown)

The title compound was isolated by chiral HPLC from Example 46. LC-MS (M+H=463, obsd=463). $^1$H NMR (400 MHz, DMSO) δ 9.77 (d, J=12.8 Hz, 2H), 9.22 (s, 1H), 8.56 (d, J=9.0 Hz, 1H), 8.28 (s, 1H), 8.06 (s, 1H), 7.61-7.46 (m, 2H), 6.90 (d, J=8.7 Hz, 1H), 4.33 (d, J=10.7 Hz, 1H), 4.11 (s, 2H), 3.79 (s, 1H), 3.70 (d, J=9.1 Hz, 1H), 2.10 (s, 2H).

p70S6K IC$_{50}$: 520 nM

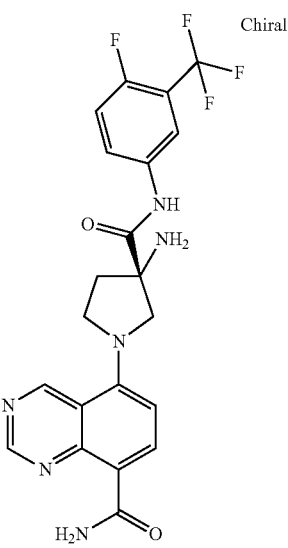 [SMILES: NC(=O)c1ccc(N2CC[C@@](N)(C(=O)Nc3ccc(F)c(C(F)(F)F)c3)C2)c2cncnc12]

Example 117

5-[(R)-3-Amino-3-(4-fluoro-3-trifluoromethyl-phenylcarbamoyl)-pyrrolidin-1-yl]-quinazoline-8-carboxylic acid amide (pure enantiomer, absolute structure unknown)

The title compound was isolated by chiral HPLC from Example 46. LC-MS (M+H=463, obsd=463). $^1$H NMR (400 MHz, DMSO) δ 9.76 (d, J=12.2 Hz, 2H), 9.22 (s, 1H), 8.56 (d, J=7.4 Hz, 1H), 8.27 (s, 1H), 8.05 (s, 1H), 7.62-7.44 (m, 2H), 6.89 (d, J=8.8 Hz, 1H), 4.32 (d, J=9.8 Hz, 1H), 4.10 (d, J=8.5 Hz, 1H), 3.79 (s, 1H), 3.69 (d, J=10.3 Hz, 1H), 2.10 (s, 2H).

p70S6K IC$_{50}$: 380 nM

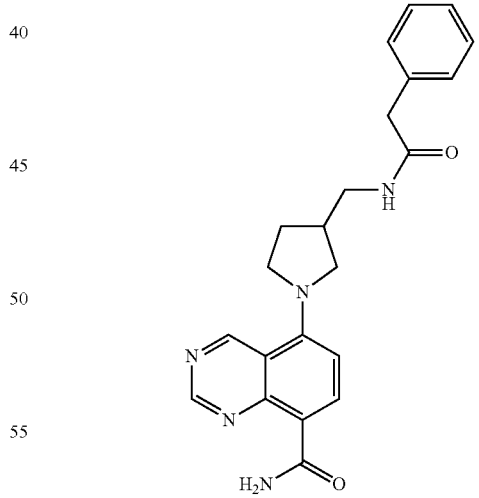

Example 118

5-{3-[(2,4-Difluoro-benzoylamino)-methyl]-pyrrolidin-1-yl}-quinazoline-8-carboxylic acid amide (racemic)

The title compound was synthesized according to the procedure described for the preparation of Example 1 by coupling with 2-phenyl-N-(pyrrolidin-3-ylmethyl)acetamide (racemic), followed by hydrolysis of the nitrile intermediate. LC-MS (M+H=390, obsd.=390). $^1$H NMR (400 MHz, DMSO) δ 9.81-9.70 (m, 2H), 9.21 (s, 1H), 8.53 (d, J=8.9 Hz, 1H), 8.22 (t, J=5.5 Hz, 1H), 7.54 (d, J=3.7 Hz, 1H), 7.33-7.24 (m, 4H), 7.24-7.16 (m, 1H), 6.81 (d, J=8.9 Hz, 1H), 3.76 (dd, J=14.9, 8.1 Hz, 3H), 3.54 (dd, J=10.2, 7.2 Hz, 1H), 3.43 (s, 2H), 3.21 (dtd, J=19.7, 13.3, 6.2 Hz, 2H), 2.08 (dd, J=11.8, 5.9 Hz, 1H), 1.83-1.67 (m, 1H).

p70S6K IC$_{50}$: 260 nM

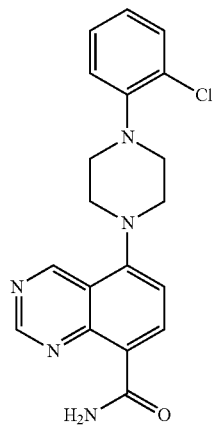 [SMILES: NC(=O)c1ccc(N2CCN(c3ccccc3Cl)CC2)c2cncnc12]

Example 119

5-[4-(2-chloro-phenyl)-piperazin-1-yl]-quinazoline-8-carboxylic acid amide

The title compound was synthesized according to the procedure described for the preparation of Example 1 by coupling with 5-Bromo-quinazoline-8-carbonitrile and 1-(2-chloro-phenyl)-piperazine, followed by hydrolysis. LC-MS. (M+H=368, obsd=368).

P70S6K IC$_{50}$: 400 nM

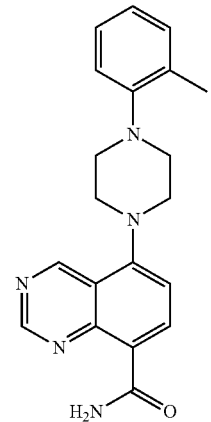 [SMILES: Cc1ccccc1N1CCN(c2ccc(C(N)=O)c3ncncc23)CC1]

Example 120

5-[4-(2-methyl-phenyl)-piperazin-1-yl]-quinazoline-8-carboxylic acid amide

The title compound was synthesized according to the procedure described for the preparation of Example 1 by cou-
pling with 5-Bromo-quinazoline-8-carbonitrile and 1-(2-methyl-phenyl)-piperazine, followed by hydrolysis. LC-MS. (M+H=348, obsd=348).

P70S6K IC$_{50}$: 980 nM

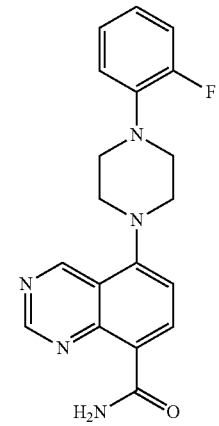 [SMILES: NC(=O)c1ccc(N2CCN(c3ccccc3F)CC2)c2cncnc12]

Example 121

5-[4-(2-fluorophenyl)-piperazin-1-yl]-quinazoline-8-carboxylic acid amide

The title compound was synthesized according to the procedure described for the preparation of Example 1 by coupling with 5-Bromo-quinazoline-8-carbonitrile and 1-(2-fluorophenyl)-piperazine, followed by hydrolysis. LC-MS. (M+H=352, obsd=352).

P70S6K IC$_{50}$: 12000 nM

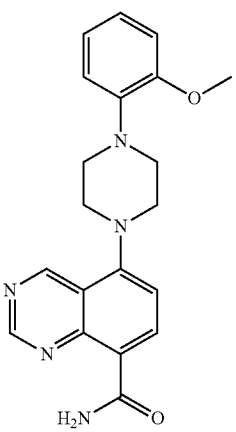 [SMILES: COc1ccccc1N1CCN(c2ccc(C(N)=O)c3ncncc23)CC1]

Example 122

5-[4-(2-methoxyphenyl)-piperazin-1-yl]-quinazoline-8-carboxylic acid amide

The title compound was synthesized according to the procedure described for the preparation of Example 1 by coupling with 5-Bromo-quinazoline-8-carbonitrile and 1-(2-methoxyphenyl)-piperazine, followed by hydrolysis. LC-MS. (M+H=364, obsd=364).

P70S6K IC$_{50}$: 11000 nM

Biological Activity
P70S6K Enzyme Assay

P70S6K inhibitor compounds are diluted and plated in 96 well plates. A reaction mixture including the following components is then added to the compound plate to initiate the enzyme reaction; P70S6K (3 nM, T412E mutant, Millipore) is mixed with 24 μM ATP in an assay buffer containing 100 mM Hepes (pH 7.5), 5 mM MgCl2, 1 mM DTT, 0.015% Brij and 1 μM of the substrate peptide FITC-AHA-AKRRRLSS-LRA-OH (derived from the S6 ribosomal protein sequence, FITC=fluorescein isothiocyanate, AHA=6-aminohexanoic acid). The reaction is incubated for 90 min at 25° C., before the addition of 10 mM EDTA to stop the reaction. The proportion of substrate and product (phosphorylated) peptide is analysed on a Caliper Life Sciences Lab Chip 3000, using a pressure of −1.4 psi, and upstream and downstream voltages of −3000 and −700 respectively. Product peaks are resolved before substrate peaks on the resulting chromatograms.

AKT Enyzme Assay

A TTP Mosquito liquid handling instrument is used to place 125 nl of the appropriate concentration of inhibitor in 100% DMSO (for a dose response curve calculation) into each well of a 384-well plate. To this reaction components are added to a final volume of 12.50

0.1 ng/μl His-AKT (Full Length), (Invitrogen, Part # P2999, Lot #641228C).
160 uM ATP (Fluka, 02055)
1 mM DTT (Sigma, D0632)
1 mM MgCl2 (Sigma, M1028)
1 μM substrate peptide (sequence FITC-AHA-GRPRTSS-FAEG-NH2), synthesized by Tufts Peptide Synthesis service.
100 mM HEPES pH 7.5 (Calbiochem, 391338)
0.015% Brij-35 (Sigma, B4184)

The reaction is incubated for 90 min at 25 C, and then stopped by the addition of 70 μl of Stop buffer (100 mM HEPES pH 7.5, 0.015% Brij-35, 10 mM EDTA (Sigma, E7889)).

The plate is read on a Caliper LC 3000 in an Off-Chip mobility shift assay format, using the following parameters for a 12-sipper chip: screening pressure −2.3 psi, upstream voltage −500, and downstream voltage −3000. These conditions cause unphosphorylated substrate and phosphorylated product peptide to resolve as separate peaks allowing direct measurement of percentage of conversion of substrate to product. The percent conversion can be plotted against concentration of inhibitor to produce a sigmoidal dose response curve, from which an IC50 can be calculated.

We claim:
1. A compound of Formula (I),

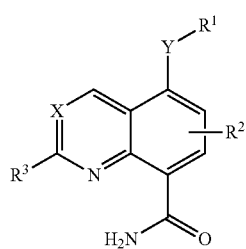

or its stereoisomers or tautomers, or pharmaceutically acceptable salts of each of the foregoing, including mixtures thereof in all ratios, wherein X is N;
Y is N—$R^5$, O, or absent;
$R^1$ is $L^1$-$R^6$, or $L^1$-$R^6$-$L^2$-$R^7$;
$R^2$ is H, Hal, OH, OA, CN, $NH_2$, or NHA;
$R^3$ is H, $CH_3$, or $C(Hal)_3$;
$R^4$ is H, Hal, OH, COOH, $NH_2$, or CN;
$R^5$ is H, LA or monocyclic alkyl having 3, 4, 5, 6, or 7 ring atoms, wherein one or two $CH_2$ groups may be replaced by a —NH— group, or
$R^5$, $R^1$ together form a monocyclic alkyl ring having 3, 4, 5, 6, or 7 ring atoms, wherein one or two $CH_2$ groups may be replaced by an O atom and/or an —NH—, —NA-, —N($L^1$-$R^6$)—, —CHA-, —$CA_2$-, CH($L^1$-$R^6$)— or —CO— group, and wherein the monocyclic alkyl ring may be substituted by $NH_2$;
$L^1$, $L^2$ are each independently a single bond, or unbranched or branched alkyl having 1, 2, 3, 4 or 5 C atoms, which may be unsubstituted, or mono- or disubstituted with Hal, OH, $NH_2$, NH(LA), N(LA)$_2$, and wherein one or two $CH_2$ groups may be replaced by an O atom or by a —CO—, —NH—, —N(LA)-, —CONH—, —N(LA)COO— or —NHCO— group;
$R^6$, $R^7$ are each independently Ar or a monocyclic alkyl ring having 3, 4, 5, 6, or 7 ring atoms, wherein one or two $CH_2$ groups may be replaced by an O atom and/or an —NH—, —NA-, —CHA-, —CO— or —CONHA- group;
each Ar is independently a mono- or bicyclic aromatic homo- or heterocycle having 0, 1, 2, 3 or 4 N, O and/or S atoms and 5, 6, 8, 9, or 10 skeleton atoms, which may be unsubstituted or, independently of one another, mono-, di- or trisubstituted by Hal, A, OA, OH, $NH_2$, or NHA;
each A is independently an unbranched or branched linear or cyclic alkyl having 1, 2, 3, 4, 5 or 6 C atoms, wherein one or two $CH_2$ groups may be replaced by an O atom and/or an —NH—, —NHCOAr or —CONHAr group wherein 1-3H atoms may be replaced by Hal, and wherein one or two $CH_3$ groups may be replaced by $NH_2$, OH, NH(LA) or N(LA)$_2$ group;
each LA is independently an unbranched or branched, linear alkyl having 1, 2, 3, or 4 C atoms wherein 1, 2 or 3H atoms may be replaced by Hal; and
each Hal is independently F, Cl, Br or I.

2. The compound according to claim 1, or its stereoisomers or tautomers, or pharmaceutically acceptable salts of each of the foregoing, including mixtures thereof in all ratios, wherein X is N and Y is N—$R^5$.

3. The compound according to claim 1, or its stereoisomers or tautomers, or pharmaceutically acceptable salts of each of the foregoing, including mixtures thereof in all ratios, wherein X is N; Y is N—$R^5$; $R^5$ and $R^1$ together form a monocyclic alkyl ring having 3, 4, 5, 6, or 7 ring atoms, wherein one or two $CH_2$ groups may be replaced by an —NH—, —NA-, —N($L^1$-$R^6$)—, —CHA-, —$CA_2$-, CH($L^1$-$R^6$)— or —CO— group, and wherein the monocyclic alkyl ring is optionally substituted by $NH_2$.

4. The compound according to claim 1, wherein the compound is selected from:
5-((4-(4-(trifluoromethoxy)phenyl)pyrrolidin-3-yl)amino)quinazoline-8-carboxamide (trans_racemic),
5-((4-phenylpiperidin-3-yl)amino)quinazoline-8-carboxamide (trans_racemic),
5-((4-(3-fluoro-4-(trifluoromethyl)phenyl)piperidin-3-yl)amino)quinazoline-8-carboxamide (trans_racemic),
5-((4-(3-(trifluoromethyl)phenyl)pyrrolidin-3-yl)amino)quinazoline-8-carboxamide, 5-((4-(4-chloro-3-fluorophenyl)piperidin-3-yl)amino)quinazoline-8-carboxamide, 5-((4-(3-chloro-4-fluorophenyl)piperidin-3-yl)amino)quinazoline-8-carboxamide, 5-(((3R,4R)-4-(3-chloro-4-fluorophenyl)piperidin-3-yl)amino)quinazoline-8-carboxamide, and 5-((4-(4-fluorophenyl)piperidin-3-yl)amino)quinazoline-8-carboxamide, or its stereoisomers or tautomers, or pharmaceutically acceptable salts of each of the foregoing, including mixtures thereof in all ratios.

5. A pharmaceutical composition comprising a compound of claim 1, and/or its stereoisomers or tautomers, or pharmaceutically acceptable salts of each of the foregoing, including mixtures thereof in all ratios, as active ingredient, together with a pharmaceutically acceptable carrier.

6. A kit consisting of separate packs of an effective amount of a compound of claim 1 and/or its stereoisomers or tautomers, or pharmaceutically acceptable salts of each of the foregoing, including mixtures thereof in all ratios, and an effective amount of a further medicament active ingredient.

7. The compound according to claim 1, or its stereoisomers or tautomers, or pharmaceutically acceptable salts of each of the foregoing, including mixtures thereof in all ratios, wherein, X is N; Y is N—$R^5$; and $R^5$ and $R^1$ together form a monocyclic alkyl ring having 4, 5 or 6 ring atoms, wherein one $CH_2$ group is replaced by an —N($L^1$-$R^6$)— group, and wherein the monocyclic alkyl ring is optionally substituted by $NH_2$.

8. The compound according to claim 1, or its stereoisomers or tautomers, or pharmaceutically acceptable salts of each of the foregoing, including mixtures thereof in all ratios, wherein, X is N; Y is N—$R^5$; $R^5$ and $R^1$ together form a monocyclic alkyl ring having 4, 5 or 6 ring atoms, wherein one $CH_2$ group is replaced by an —N($L^1$-$R^6$)— group, and wherein the monocyclic alkyl ring is optionally substituted by $NH_2$; and $L^1$ is a bond, —CONH—, —NHCO—, —CONHCH$_2$—, or CH$_2$CONH—.

9. The compound according to claim 1, or its stereoisomers or tautomers, or pharmaceutically acceptable salts of each of the foregoing, including mixtures thereof in all ratios, wherein, X is N; Y is N—$R^5$; $R^5$ and $R^1$ together form a monocyclic alkyl ring having 4, 5 or 6 ring atoms, wherein one $CH_2$ group is replaced by an —N($L^1$-$R^6$)— group, and wherein the monocyclic alkyl is optionally substituted by $NH_2$; and $R^6$ is phenyl, which is unsubstituted, or independently mono-, di- or trisubstituted by Hal, C(Hal)$_3$, CH$_3$, or C(Hal)$_3$O.

10. The compound according to claim 1, or its stereoisomers or tautomers, or pharmaceutically acceptable salts of each of the foregoing, including mixtures thereof in all ratios, wherein, X is N; Y is N—$R^5$; $R^5$ and $R^1$ together form a monocyclic alkyl ring having 4, 5 or 6 ring atoms, wherein one $CH_2$ group is replaced by an —N($L^1$-$R^6$)— group, and wherein the monocyclic alkyl ring is optionally substituted by $NH_2$; $L^1$ is a bond, —CONH—, —NHCO—, —CONHCH$_2$—, or CH$_2$CONH—; and $R^6$ is phenyl, which is unsubstituted, or independently mono-, di- or trisubstituted by Hal, C(Hal)$_3$, CH$_3$, CH$_3$O, or C(Hal)$_3$O.

11. The compound according to claim 1, or its stereoisomers or tautomers, or pharmaceutically acceptable salts of each of the foregoing, including mixtures thereof in all ratios, wherein, X is N; Y is NH; $R^1$ is $L^1$-$R^6$-$L^2$-$R^7$; $L^1$ and $L^2$ are a bond; $R^6$ is a monocyclic alkyl ring having 4, 5 or 6 ring atoms, wherein one $CH_2$ group is replaced by an —NH—, group; and $R^7$ is phenyl, which is unsubstituted, or independently mono-, di- or trisubstituted by Hal, C(Hal)$_3$, CH$_3$, CH$_3$O, or C(Hal)$_3$O.

12. The compound according to claim 1, or its stereoisomers or tautomers, or pharmaceutically acceptable salts of each of the foregoing, including mixtures thereof in all ratios, wherein, X is N; Y is NH; $R^1$ is $L^1$-$R^6$-$L^2$-$R^7$; $L^1$ and $L^2$ are a bond; $R^6$ is piperidyl or pyrrolidinyl; and $R^7$ is phenyl, which is mono- or disubstituted by Hal, C(Hal)$_3$, CH$_3$, CH$_3$O, or C(Hal)$_3$O.

13. The compound according to claim 1, or its stereoisomers or tautomers, or pharmaceutically acceptable salts of each of the foregoing, including mixtures thereof in all ratios, wherein, X is N; Y is NH; $R^1$ is $L^1$-$R^6$-$L^2$-$R^7$; $L^1$ and $L^2$ are a bond; $R^6$ is

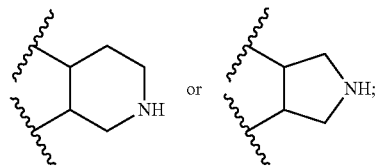 [SMILES: *C1CCNCC1* ; "or" ; *C1CNCC1*]

and $R^7$ is phenyl, which is mono- or disubstituted by Hal, C(Hal)$_3$, CH$_3$, CH$_3$O, or C(Hal)$_3$O.

* * * * *